(12) United States Patent
Nehra et al.

(10) Patent No.: US 8,216,841 B2
(45) Date of Patent: Jul. 10, 2012

(54) SOMATIC EMBRYOGENESIS AND EMBRYO HARVESTING AND METHOD FOR PREPARING PLANT EMBRYOS FOR PLANT PRODUCTION

(75) Inventors: Narender Singh Nehra, Summerville, SC (US); Mark Russell Rutter, Summerville, SC (US); John Joseph Clark, Summerville, SC (US); Jessica S. Sage, Summerville, SC (US); Sydney Keith Seymour, Summerville, SC (US); Timothy Joel Stout, Summerville, SC (US); Ronald W. Winkles, Summerville, SC (US); George W. Surritte, Summerville, SC (US)

(73) Assignee: Arborgen Inc., Ridgeville, SC (US)

( * ) Notice: Subject to any disclaimer, the term of this patent is extended or adjusted under 35 U.S.C. 154(b) by 85 days.

(21) Appl. No.: 12/511,548

(22) Filed: Jul. 29, 2009

(65) Prior Publication Data

US 2010/0024081 A1 Jan. 28, 2010

Related U.S. Application Data

(62) Division of application No. 11/413,105, filed on Apr. 28, 2006, now Pat. No. 7,665,243.

(60) Provisional application No. 60/675,949, filed on Apr. 29, 2005.

(51) Int. Cl.
C12N 5/00 (2006.01)
C12N 5/02 (2006.01)

(52) U.S. Cl. ............. 435/422; 435/431; 435/430.1; 800/319

(58) Field of Classification Search ............ 435/422, 435/420, 430.1, 431; 800/319
See application file for complete search history.

(56) References Cited

U.S. PATENT DOCUMENTS

| | | | |
|---|---|---|---|
| 5,088,231 A | 2/1992 | Kertz | |
| 5,183,757 A | 2/1993 | Roberts | |
| 5,413,930 A | 5/1995 | Becwar et al. | |
| 5,534,433 A | 7/1996 | Coke | |
| 5,558,984 A | 9/1996 | Young | |
| 5,677,185 A | 10/1997 | Handley, III | |
| 6,180,405 B1 | 1/2001 | Aitken-Christie et al. | |
| 6,893,873 B2 * | 5/2005 | Pullman | 435/422 |
| 2002/0155595 A1 | 10/2002 | Adelberg et al. | |
| 2004/0267457 A1 | 12/2004 | Timmis et al. | |
| 2005/0026281 A1 | 2/2005 | Gupta et al. | |

FOREIGN PATENT DOCUMENTS

| | | |
|---|---|---|
| WO | WO 98/57536 | 12/1998 |
| WO | WO 2005/011358 | 2/2005 |

OTHER PUBLICATIONS

Bornman et al. Regeneration of Plants from the Conifer Leaf with special reference to *Picea abies* and *Pinus sylvestris*. Cell and Tissue Culture, 1981, pp. 41-53.*
Dodds et al. Experiments in Plant Tissue Culture, 2nd ed. Cambridge University Press 1988, pp. 210-211.*
Gray et al. Somatic Embryogenesis in Suspension and Suspension-Derived Callus Cultures of *Dactylis glomerata*. Protoplasma 122, pp. 196-202, 1984.*
Gray et al. Influence of dicamba and casein hydrolysate on somatic embryo number and culture quality in cell suspension of *Dactylis glomerata* (Gramineae). Plant Cell Tissue Organ Culture 4 (1985) 123-133.*
Hristoforoglu et al. Development and germination of *Abies alba* somatic embryos. Plant Cell, Tissue and Organ Culture 40:277-284, 1995.*
Pullman et al. Brassinolide improves embryogenic tissue initiation in conifers and rice. Plant Cell Rep (2003) 22:96-104.*
Redway et al. Identification of callus types for long-term maintenance and regeneration from commercial cultivars of wheat (*Triticum aestivum* L.) Theor Appl Genet (1990) 79: 609-617.*
Renfroe. Getting stated in plant tissue culture 2006 [online] [retrieved on Apr. 26, 2011]. Retrived from the Internet at <http://csm.jmu.edu/biology/renfromh/pop/pctc/tcstart.htm> pp. 1-4.*
Von Aderkas et al. Charcoal affects early development and hormonal concentrations of somatic embryos of hybrid larch. Tree Physiology 22, 2002, 431-434.*
International Search Report for PCT International Application PCT/US06/16075, mailed Mar. 14, 2008. (2 pgs.).
Becwar, M.R., et al, "A method for quantification of the level of somatic embryogenesis among Norway spruce callus lines," *Plant Cell Reports*, vol. 6, 1987, pp. 35-38.
The Translation of the Examiner's Report issued on May 3, 2010 in the related Chilean Patent Application No. 1033-2006.

* cited by examiner

*Primary Examiner* — June Hwu
(74) *Attorney, Agent, or Firm* — Foley & Lardner LLP

(57) ABSTRACT

Described herein are methods and media for facilitating somatic embryogenesis and for collecting, conditioning, and transferring the washed embryos onto a substrate and into an environment suitable for conditioning the embryos for a desired period of time so they become germination-competent for plant production. The described plant embryo cleaning apparatus and method are used for preparing multiple plant embryos for plant production. The apparatus and method can use a cleaning fluid source, a fluid-conditioning system, a fluid-delivery structure, a cleaning station, an outlet mechanism, a negative pressure source, and a controller.

21 Claims, 17 Drawing Sheets

SOMATIC EMBRYOGENESIS AND EMBRYO HARVESTING AND METHOD FOR PREPARING PLANT EMBRYOS FOR PLANT PRODUCTION

This application claims priority to U.S. Provisional Application Ser. No. 60/675,949, which was filed on Apr. 29, 2005, and which is incorporated herein in its entirety by reference.

FIELD OF THE INVENTION

Described herein are methods and media for facilitating somatic embryogenesis and for collecting, conditioning, and storing of large numbers of plant embryos prior to germination. Also described herein are a method and apparatus for preparing plant embryos for plant production.

BACKGROUND

Collecting, storing, and conditioning plant embryos, especially somatic embryos, prior to germination are key processes in many aspects of the agriculture industry. The activities necessary for performing these processes, however, are usually performed by hand. For instance, individual embryos are typically transferred to and from various media and vessels and must be plated onto gel media, one by one using forceps and often with the guidance of a dissecting microscope.

Such "hand harvesting" methods are burdensome, time-consuming, costly, and susceptible to contamination. Not only that, but only a limited number of embryos can be collected and treated by a single person during a given period of time. Accordingly, any attempt to increase the number of embryos that can be harvested and subsequently conditioned for germination necessarily requires an increase in manpower, which itself can be costly and often impractical.

An added concern is the inclusion of polyethylene glycol in embryo development media as a osmotic agent. Polyethylene glycol has been incorporated into various media to boost embryogenic development because it is thought to help trigger embryo development. See Fowke et al., Somatic Cell Genetics and Molecular Genetics of Trees, Quebec City, Canada, Aug. 12-16, 1997, which is incorporated herein by reference.

A problem with polyethylene glycol, however, is that it adheres to embryos, possibly interfering with embryo germination. Traditionally, removal of polyethylene glycol is accomplished by storing polyethylene glycol (PEG)-treated embryos on a gel medium without PEG in the cold for a number of weeks. The polyethylene glycol eventually diffuses into the medium away from the embryos. Not surprisingly, this is a time-consuming and burdensome treatment and removal strategy, which imparts an oftentimes unacceptable delay in the overall harvesting and conditioning process.

The agricultural industry and, in particular, the forestry sciences, therefore, are faced with a laborious, expensive, and inefficient method for making, gathering and preparing plant embryos. Such factors prove to be obstacles when operating at commercial levels. And still, hand harvesting is a typically routine practice.

As explained below, however, the present invention provides a robust "Mass Harvesting" method that is rapid and inexpensive. Since Mass Harvesting (MH) minimizes human intervention, it is less susceptible to contamination. Furthermore, the present invention also provides a new way for removing polyethylene glycol. Moreover, the Mass Harvesting method is highly efficient, allowing the simultaneous collection of thousands and hundreds of thousands of plant embryos during a period of time, and can be readily scaled-up for commercial purposes.

In this respect, the present invention also provides a combinatorial approach to exploiting and optimizing genotype-by-treatment interactions of multiple steps in the somatic embryogenesis process.

SUMMARY

In one aspect of the invention, a method for preparing embryos for plant production is provided, which comprises (i) washing multiple plant embryos simultaneously, and (ii) transferring the washed embryos onto a substrate and into an environment suitable for conditioning the embryos for a desired period of time so they become germination-competent for plant production. The method may further comprise retrieving one or more of the embryos at any time point during the desired period of time.

In one embodiment, the plant embryos are somatic embryos. In another embodiment, the embryos are washed on a porous surface. In yet another embodiment, no single embryo has been individually placed by hand onto the porous surface.

In one embodiment, the substrate that is suitable for storing the embryos is a gel, which comprises maltose, glutamine, and abscisic acid. The gel also may contain other ingredients, such as inorganic nutrients. The person of skill in the art of embryo storage and development knows what other ingredients are useful for maintaining and manipulating plant embryos. In another embodiment, the substrate is a filter paper saturated with a volume of liquid media, which comprises maltose, glutamine, and abscisic acid. The gel also may contain other ingredients, such as inorganic nutrients. In another embodiment, the volume of the liquid media that is added to the substrate is 1 ml or 2 ml.

Other conditioning embodiments include, but are not limited to, the following: embryos stored on a gelled medium in cold (1° C. to 12° C., optimally 3 to 6° C.) for varying time (1 day to 24 weeks, optimally from 3 to 12 weeks). During this cold storage the embryos can be placed on a polyester or paper membrane to facilitate subsequent transfer. Embryos on the polyester or paper membrane are then transferred as an entire unit to a vessel and sealed with Nescofilm™, or optionally are placed on top of a dry filter paper within the vessel and sealed with Nescofilm™. Embryos in the sealed vessel are held at room temperature (15 to 30° C., ideally 20 to 28° C.) for varying time (1 to 12 weeks, optimally from 2 to 5 weeks depending on the temperature to which the embryos were exposed during either of the above steps of this conditioning method. That is during: a. cold on a gelled medium and, b. warm in sealed vessel).

In one embodiment, the embryos are stored for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, or more than about 24 weeks.

Another aspect of the present invention is a liquid medium for growing embryonic tissue that comprises a high concentration of casein. A high concentration of casein may be about 900 mg/l, about 1000 mg/l, about 1100 mg/l, about 1200 mg/l, about 1300 mg/l, about 1400 mg/l, about 1500 mg/l, about 1600 mg/l, about 1700 mg/l, about 1800 mg/l, about 1900 mg/l, about 2000 mg/l, about 2100 mg/l, about 2200 mg/l, about 2300 mg/l, about 2400 mg/l, about 2500 mg/l, about 2600 mg/l, about 2700 mg/l, about 2800 mg/l, about 2900 mg/l, about 3000 mg/l, or more than 3000 mg/l. In one embodiment the concentration of casein is between 1100 mg/l and 3000 mg/l.

In one embodiment, the embryonic tissue is from a conifer. In a preferred embodiment, the conifer is pine. In a more preferred embodiment, the pine is Loblolly pine.

In another embodiment, the coniferous tree is selected from the group consisting of Eastern white pine, Western white, Sugar pine, Red pine, Pitch pine, Jack pine, Longleaf pine, Shortleaf pine, Loblolly pine, Slash pine, Virginia pine, Ponderosa pine, Jeffrey pine, Pond pine, and Lodgepole pine, Radiata pine and hybrid crosses thereof. In another preferred embodiment, the coniferous tree is selected from the group consisting of, but not limited to, *Abies alba, Abies amabilis, Abies balsamea, Abies bornmuelleriana, Abies concolor, Abies fraseri, Abies grandis, Abies koreana, Abies lasiocarpa, Abies nordmanniana, Abies procera, Araucaria angustifolia, Araucaria araucana, Araucaria bidwillii, Araucaria cunninghamii, Cedrus atlantica, Cedrus deodara, Chamaecyparis lawsoniana, Chamaecyparis pisifera, Cryptomeria japonica, Cuppressocyparis leylandii, Larix decidua, Larix occidentalis, Metasequoia glyptostroboides, Picea abies, Picea engelmannii, Picea glauca, Picea mariana, Picea pungens, Picea rubens, Picea sitchensis, Pinus banksiana, Pinus caribaea, Pinus contorta, Pinus echinata, Pinus edulis, Pinus elliotii, Pinus jeffreyi, Pinus korariensis, Pinus lambertiana, Pinus merkusii, Pinus monticola, Pinus nigra, Pinus palustris, Pinus pinaster, Pinus ponderosa, Pinus rigida, Pinus radiata, Pinus resinosa, Pinus serotina, Pinus strobus, Pinus sylvestris, Pinus taeda, Pinus virginiana, Pseudotsuga menziesii, Sequoia sempervirens, Sequoiadendron giganteum, Taxodium ascends, Taxodium distichum, Taxus baccata, Taxus brevifolia, Taxus cuspidata, Thuja occidentalis, Thuja plicata, Tsuga canadensis, Tsuga heterophylla,* and hybrid crosses thereof.

Specific examples of each of such coniferous tree includes: *Abies alba*, European silver fir; *Abies amabilis*, Pacific silver fir; *Abies balsamea*, Balsam fir; *Abies bornmuelleriana*, Turkish fir; *Abies concolor*, White fir; *Abies fraseri*, Fraser fir; *Abies grandis*, Grand fir; *Abies koreana*, Korean fir; *Abies lasiocarpa*, Alpine fir; *Abies nordmanniana*, Nordman fir; *Abies procera*, Noble fir; *Araucaria angustifolia*, Parana pine; *Araucaria araucana*, Monkeypuzzle tree; *Araucaria bidwillii*, Bunya pine; *Araucaria cunninghamii*, Hoop pine; *Cedrus atlantica*, Atlas cedar; *Cedrus deodara*, Deodar cedar; *Chamaecyparis lawsoniana*, Port-Orford-cedar; *Chamaecyparis pisifera*, Sawara cypress; *Cryptomeria japonica*, Japanese cedar (Japanese cryptomeria); *Cuppressocyparis leylandii*, Leyland Cypress; *Larix decidua*, European larch; *Larix occidentalis*, Western larch; *Metasequoia glyptostroboides*, Dawn redwood; *Picea abies*, Norway spruce; *Picea engelmannii*, Englemann spruce; *Picea glauca*, White spruce; *Picea mariana*, Black spruce; *Picea pungens*, Colorado blue spruce; *Picea rubens*, Red spruce; *Picea sitchensis*, Sitka spruce; *Pinus banksiana*, Jack pine; *Pinus caribaea*, Caribbean pine; *Pinus contorta*, lodgepole pine; *Pinus echinata*, Shortleaf pine; *Pinus edulis*, Pinyon pine; *Pinus elliotii*, Slash pine; *Pinus jeffreyi*, Jeffrey Pine; *Pinus korariensis*, Korean pine; *Pinus lambertiana*, Sugar pine; *Pinus merkusii*, Sumatran pine; *Pinus monticola*, Western white pine; *Pinus nigra*, Austrian pine; *Pinus palustris*, Longleaf pine; *Pinus pinaster*, Maritime pine; *Pinus ponderosa*, Ponderosa pine; *Pinus rigida*, Pitch pine; *Pinus radiata*, Radiata pine; *Pinus resinosa*, Red pine; *Pinus serotina*, Pond pine; *Pinus strobus*, Eastern white pine; *Pinus sylvestris*, Scots (Scotch) pine; *Pinus taeda*, Loblolly pine; *Pinus virginiana*, Virginia pine; *Pseudotsuga menziesii*, Douglas-fir; *Sequoia sempervirens*, Redwood; *Sequoiadendron giganteum*, Sierra redwood; *Taxodium ascends*, Pond cypress; *Taxodium distichum*, Bald cypress; *Taxus baccata*, European yew; *Taxus brevifolia*, Pacific or Western yew; *Taxus cuspidata*, Japanese yew; *Thuja occidentalis*, Northern white-cedar; *Thuja plicata*, Western red cedar; *Tsuga canadensis*, Eastern hemlock; *Tsuga heterophylla*, Western hemlock.

In another embodiment, the coniferous plant tissue is a Southern Yellow pine. In yet another embodiment, the Southern Yellow pine is selected from the group consisting of *Pinus taeda, Pinus serotina, Pinus palustris,* and *Pinus elliottii.*

The present invention contemplates the Mass Harvesting of somatic embryos from any of these coniferous trees. The present invention is not limited, however, to the Mass Harvesting of only coniferous tree tissues and somatic embryos.

In another embodiment, therefore, the plant tissue, such as embryogenic tissue or a somatic embryo is from a tree selected from the group consisting of chestnut, ash, beech, basswood, birch, black cherry, black walnut/butternut, chinkapin, cottonwood, elm, eucalyptus, hackberry, hickory, holly, locust, magnolia, maple, oak, poplar, red alder, royal paulownia, sassafras, sweetgum, sycamore, tupelo, willow, and yellow-poplar, and intra- and inter-species hybrid crosses thereof. A particularly preferred chestnut for use in the present invention is the American Chestnut.

In one embodiment, the concentration of casein in the liquid medium is about 400, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, or about 3000 mg/l or any integer in between these concentrations.

In one embodiment, the casein is casein hydrolysate.

Another aspect of the present invention is a method for obtaining germinating embryos, comprising (i) placing embryogenic cultures from cryostorage onto cryoretrieval medium for a period of time and thereafter growing the embryogenic tissue in liquid medium, (ii) transferring the embryogenic tissue to embryo development medium to generate embryos, (iii) washing a mass of the generated embryos with water, (iv) placing the washed mass of embryos on a substrate that is saturated with conditioning medium, and (v) germinating embryos therefrom, wherein (a) the cryoretrieval medium comprises at least one of a high concentration of casein or an amount of Brassinolide, (b) the liquid medium has a high concentration of casein, (c) the embryo development medium has a desired amount of polyethylene glycol, and (d) the conditioning medium is liquid.

In this method, the liquid medium comprises a concentration of casein which is about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, or about 3000 mg/l or any integer in between these concentrations.

In another embodiment, the percentage of polyethylene glycol in the embryo development medium is 1%, 2%, 3%, 4%, 5%, 6%, 7%, 8%, 9%, 10%, 11%, 12%, 13%, 14%, 15%, 16%, 17%, 18%, 19%, or 20%. In one embodiment, the percentage of polyethylene glycol in the embryo development medium is 7%. In another embodiment, the percentage of polyethylene glycol in the embryo development medium is 13%.

In one embodiment, the cryoretrieval medium comprises an amount of Brassinolide. In one embodiment, the amount of Brassinolide is 0.01 µM, 0.02 µM, 0.03 µM, 0.04 µM, 0.05 µM, 0.06 µM, 0.07 µM, 0.08 M, 0.09 µM, 0.10 µM, 0.11 µM, 0.12 µM, 0.13 µM, 0.14 µM, 0.15 µM, 0.16 µM, 0.17 µM, 0.18 µM, 0.19 µM, 0.20, or 0.50 µM. In one embodiment, the concentration of Brassinolide is 0.10 µM.

In another aspect, a method for identifying optimal genotype-specific conditions for embryogenic tissue growth is provided, comprising (i) growing embryogenic tissue that has been retrieved from cryostorage on a medium that comprises an amount of Brassinolide and (ii) comparing the growth of the embryogenic tissue to the growth of embryogenic tissue from the same genotype on media that comprises at least one different amount of Brassinolide.

In another aspect, a method for identifying optimal genotype-specific conditions for embryo production is provided, comprising (i) growing embryogenic cultures on an embryo development medium that comprises an amount of polyethylene glycol and (ii) comparing the growth of the embryogenic cultures into embryos to the growth of embryos from the same genotype on embryo development media that comprises at least one different amount of polyethylene glycol.

In another aspect of the methods disclosed herein are combined to produce a method for identifying optimal genotype-specific conditions for embryogenic tissue growth and embryo production for a particular plant genotype.

In one embodiment, after Mass Harvesting according to any one of these methods, embryos are placed onto a substrate that has been saturated with a volume of liquid conditioning medium, which contains nutrients necessary to prepare the embryos for germination. The substrate may be a filter paper.

In one embodiment, the saturated filter paper onto which the embryos are placed is retained within a dish, such as a Petri dish. In another embodiment, the dish is wrapped with tape or porous wrapping material to control the loss of moisture from the dish. In another embodiment, the dish, which contains the filter paper and the embryos thereon is stored in the cold for a period of time.

The length of time a Mass Harvested somatic embryo can be stored in the cold is from 1 to 5 weeks, for at least 5 weeks, for at least 8 weeks, for at least 10 weeks, for at least 12 weeks, for at least 13 weeks, for at least 14 weeks, for at least 15 weeks, for at least 16 weeks, 18 weeks, 20 weeks, 22 weeks, 24 weeks, or for more than 24 weeks.

For instance, a Mass Harvested somatic embryo may be stored in the cold under the conditions described herein for 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks, or beyond 52 weeks.

In one aspect of the present invention is a combinatorial method for optimizing somatic embryogenesis, comprising (i) initiating embryogenesis of a plant embryogenic tissue on an initiation medium that comprises a high concentration of casein, (ii) maintaining the initiated embryogenic tissue on a maintenance medium that comprises a high concentration of casein prior to cryostorage, (iii) recovering the embryogenic tissue from cryostorage on a medium that comprises at least one of (a) high concentration of casein or (b) an amount of Brassinolide, and (iv) developing embryos from the recovered embryogenic tissue on an embryo development medium that comprises a percentage of polyethylene glycol that is optimal for the genotype of the embryogenic tissue from which embryos are to be developed.

In one embodiment of this method, the percentage of polyethylene glycol in the embryo development medium is 1%, 2%, 3%, 4%, 5%, 6%, 7%, 8%, 9%, 10%, 11%, 12%, 13%, 14%, 15%, 16%, 17%, 18%, 19%, or 20%. In one embodiment, the percentage of polyethylene glycol in the embryo development medium is 7%. In another embodiment, the percentage of polyethylene glycol in the embryo development medium is 13%.

In another embodiment, the medium onto which the embryogenic tissue is recovered after cryostorage comprises a high concentration of casein and an amount of Brassinolide.

In one embodiment, the amount of Brassinolide is 0.01 µM, 0.02 µM, 0.03 µM, 0.04 µM, 0.05 µM, 0.06 µM, 0.07 µM, 0.08 µM, 0.09 µM, 0.10 µM, 0.11 µM, 0.12 µM, 0.13 µM, 0.14 µM, 0.15 µM, 0.16 µM, 0.17 µM, 0.18 µM, 0.19 µM, or 0.20 µM. In one embodiment, the concentration of Brassinolide is about 0.10 µM.

In another embodiment, the initiation medium further comprises a low concentration of maltose. In one embodiment, the concentration of maltose is about 1 g/l, 2 g/l, 3 g/l, 4 g/l, 5 g/l, 6 g/l, 7 g/l, 8 g/l, 9 g/l, 10 g/l, 11 g/l, 12 g/l, 13 g/l, 14 g/l, 15 g/l, 16 g/l, 17 g/l, 18 g/l, 19 g/l, or 20 g/l. In one embodiment, the concentration of maltose is about 15 g/l.

In another aspect of the present invention is a method for preparing embryos for storage, comprising (i) simultaneously washing multiple plant embryos, and (ii) transferring the washed embryos onto a substrate suitable for conditioning the embryos for storage in a vessel for a desired period of time. In one embodiment, wherein the plant embryos are somatic embryos. In one embodiment, the plant embryos are washed onto a mesh that permits passage of cellular debris and liquid but not the passage of the embryos. Hence, in one embodiment, the embryos are washed on a porous surface and wherein no embryo is placed by hand onto the porous surface. In one embodiment, the step of transferring the washed embryos comprises inverting the mesh on which the embryos were washed directly onto the substrate, wherein the substrate is either already in the vessel or is subsequently moved to a vessel or environment for suitable conditioning and storage. Hence, the embryos may be inverted from the washing mesh and onto a conditioning substrate.

In another embodiment, the conditioning substrate is a gel comprising maltose, glutamine, and abscisic acid. In another embodiment, the conditioning substrate is a filter paper saturated with a volume of liquid media, which comprises maltose, glutamine, and abscisic acid. In one embodiment, the volume of the liquid media is 1 ml or 2 ml.

In one embodiment, conditioning takes place in a high relative humidity environment without cold storage. In another embodiment, conditioning comprises storing the embryos on a gelled medium in the cold for a period of time. In another embodiment, the method further comprises placing the embryos onto a polyester or paper membrane, transferring the membrane to a vessel, which is then sealed, maintaining the vessel at a warm temperature for a period of time.

An aspect of the present invention relates to an apparatus for preparing multiple plant embryos for plant production. The apparatus includes a fluid-delivery structure for delivering input liquid to the multiple plant embryos, a cleaning station in fluid communication with the fluid-delivery structure and configured to hold the multiple plant embryos to receive input liquid from the fluid-delivery structure to clean cellular debris from the multiple plant embryos, an outlet mechanism in fluid communication with the cleaning station and configured to receive output liquid from the cleaning station, and a controller configured to control at least one of the fluid-delivery structure, the cleaning station, and the outlet mechanism.

In an embodiment, the fluid-delivery structure can include a spray mechanism for spraying the multiple plant embryos.

In another embodiment, the cleaning station can include a wash unit for washing the multiple plant embryos, and a rinse unit for rinsing the multiple plant embryos.

In yet another embodiment, the rinse unit can include a porous material configured to hold the multiple plant embryos and having a pore size within a range of 15 microns to 65 microns. The porous material can be configured to hold the multiple plant embryos, the porous material being removable to remove the multiple plant embryos from the rinse unit.

In yet another embodiment, the cleaning station can include a holding unit that transports the multiple plant embryos from the wash unit to the rinse unit. The holding unit can include a porous material in which the pore size can be within the range of 400 microns to 900 microns. The holding unit can include a first porous material configured to hold the multiple plant embryos and having a first pore size. The rinse unit can include a second porous material configured to hold the multiple plant embryos and having a second pore size. Preferably, the second pore size is smaller than the first pore size.

In yet another embodiment, at least one of the fluid delivery structure, wash unit, rinse unit, and holding unit includes a substantially transparent housing to permit monitoring of at least one of washing and rinsing through the substantially transparent housing.

In yet another embodiment, the apparatus includes structure controlled by the controller to move the holding unit from the wash unit to the rinse unit.

In yet another embodiment, the outlet mechanism can include a first outlet in fluid communication with the wash unit and configured to receive output liquid from the wash unit, and a second outlet in fluid communication with the rinse unit and configured to receive output liquid from the rinse unit.

In yet another embodiment, the apparatus can include a negative pressure source in fluid communication with the outlet mechanism to provide a negative pressure. The negative pressure source can include a vacuum system comprising an electronic valve connected to a vacuum pump. The negative pressure source can include a check valve in fluid communication with the cleaning station and configured to operate as a function of output liquid weight and a force of the negative pressure.

In another embodiment, preferably, the controller is configured to control the flow of input liquid through the fluid-delivery structure. The controller can be configured to control the pressure of input liquid delivered by the fluid-delivery structure. The controller can be configured to maintain the impingement of the input liquid within a range of 0.00506 to 0.027 pounds per square inch at a normalized standard distance of twelve inches.

In yet another embodiment, the apparatus can include a negative pressure source in fluid communication with the outlet mechanism, wherein the controller is configured to control a pressure of input liquid delivered by the fluid-delivery structure and to control a pressure supplied by the negative pressure source to the outlet mechanism.

In yet another embodiment, the cleaning station can include a wash unit, and a rinse unit configured to hold the multiple plant embryos. The outlet mechanism can include a first outlet in fluid communication with the wash unit and configured to receive first output liquid from the wash unit, and a second outlet in fluid communication with the rinse unit and configured to receive second output liquid from the rinse unit. The apparatus can further include a negative pressure source in fluid communication with the first and second outlets to supply negative pressure to the first and second outlets, wherein the controller is configured to control the fluid-delivery structure and the negative pressure source.

In yet another embodiment, the apparatus can include a fluid-conditioning system in fluid communication with the fluid-delivery structure and configured to at least one of filter the input liquid and sterilize the input liquid. The fluid-conditioning system can include a membrane filter and a UV sterilizer.

In yet another embodiment, the cleaning station can be configured to remove polyethylene glycol from the multiple plant embryos.

Another aspect of the present invention relates to a method of preparing multiple plant embryos for plant production. The method includes supplying multiple plant embryos in a cleaning station, washing the multiple plant embryos by delivering an input liquid to the plant embryos, and controlling with a controller a flow of input liquid delivered to the plant embryos.

In an embodiment, the impingement of the input liquid can be maintained within a range of 0.00506 to 0.027 pounds per square inch at a normalized standard distance of twelve inches.

In another embodiment, the method can further include supplying a negative pressure to the cleaning station for controlling flow of output liquid, and controlling with the controller the negative pressure supplied to the cleaning station.

In yet another embodiment, the method can further include at least one of filtering the input liquid and sterilizing the input liquid.

In yet another embodiment, the method can include removing polyethylene glycol from the multiple plant embryos in the washing step.

Yet another aspect of the present invention relates to a method of preparing multiple plant embryos for plant production. The method includes supplying multiple plant embryos in a wash unit, washing the multiple plant embryos by delivering a first input liquid into the wash unit, transporting the multiple plant embryos to a rinse unit, rinsing the multiple plant embryos by delivering a second input liquid into the rinse unit, and controlling with a controller at least one of the steps of washing, transporting, and rinsing.

In an embodiment, the method can further include applying a first negative pressure to the wash unit for controlling flow of first output liquid from the wash unit, and applying a second negative pressure to the rinse unit for controlling flow of second output liquid from the rinse unit.

In another embodiment, the method can further include at least one of filtering the first and second input liquids and sterilizing the first and second input liquids.

In yet another embodiment of the method, the first input liquid and the second input liquid can have the same composition. Alternatively, the first input liquid and second input liquid can have different compositions.

Yet another aspect of the present invention relates to a method of preparing multiple conifer somatic embryos for plant production. The method includes positioning the multiple conifer somatic embryos on a porous material having a pore size within a range of 400 microns to 900 microns, and delivering fluid to the multiple conifer somatic embryos on the porous material to clean the conifer somatic embryos. In a further refinement, the pore size of the porous material can be within a range of 560 microns to 710 microns or within a range of 600 microns to 670 microns.

In one embodiment of the present invention at least one of the steps of washing and transferring are automated. Indeed, any one of the methods disclosed herein may comprises steps that are fully or partly automated and/or are computer-operated by software programs that may or may not require human input, intervention, or interaction. In this respect, the present invention also contemplates a fully-automated and semi-automated apparatuses or machines for harvesting embryos. Such an apparatus according to the present invention performs various automated functions pertinent to embryo harvesting techniques of the present invention. Hence, a fully- or semi-automated apparatus of the present invention may perform functions comprising (1) loading of embryos onto a surface, (2) washing of the embryos, (3) rinsing of the embryos, and (4) unloading or transferring of the embryos from the surface to another surface or vessel or container for further manipulation. The apparatus may transfer the treated embryos, by means of a robotic arm or a movable surface, for instance, to a conditioning environment without human intervention. Hence, human intervention may only ever be required at the step of bringing embryos to the apparatus and placing them into or onto the appropriate apparatus surface. From that point onwards, no further human intervention may be necessary until the embryos have been conditioned for a desired period of time. At that point, a human may remove one or more embryos from that conditioning environment to assess whether it is germination competent and then move onwards to plant that germination-ready embryo for plant propagation. Even then, that step, the step of removing the germination-competent embryos can be automated. That is, the apparatus may be designed such that the embryos are automatically removed from the conditioning environment after a period of time that is known to produce germination-competent embryos, and placed onto an appropriate seeding and rooting surface so as to promote germination and shoot growth.

A semi-automated apparatus that performs such functions may be semi-automated in the sense that it may require human intervention at certain points in the process, such as bringing embryos to the apparatus, permitting human intervention to increase or decrease a wash or rinse step, or simply to initiate the computer software that controls the operation of the components of the apparatus. Hence, the present invention contemplates the apparatus that is described herein and which performs the functions outlined above. See also Example 23 below.

The present invention also recognizes and appreciates that certain features of this apparatus can be modified or altered in due course and in response to the embryo harvesting task desired. Hence, the apparatus may be modified so as to increase the total numbers of embryos that can be treated according to the harvesting and washing protocols disclosed herein. For instance, the apparatus disclosed in Example 23, may include more than three units within which to wash embryos. That is, the apparatus may be adapted to include more units or units of larger capacity. Furthermore, the present invention contemplates the manipulation of the computer software that drives and operates the apparatus. In this respect, the present invention contemplates that an automated apparatus of the present invention is controlled by computer software that follows and implements, in computer terms, the process flow diagram depicted in FIG. 11. For instance, the apparatus described herein may be operated by and under the control of computer software that implements the process of FIG. 11. The skilled person appreciates that any of these parameters are open to manipulation. Hence, the present invention contemplates software that controls sensors, which determine the approximate load of embryos that are placed onto a loading surface. Depending on that determination, the software may make and send appropriate computer commands to increase or decrease the length of time of the wash and rinse steps, for example. Hence, if a subsequent batch of embryos is twice that of what was previously loaded, the sensors will direct the duration of the ensuing wash step to be longer or more powerful, or may require the steps of washing and rinsing to be repeated any number of times. Accordingly, the automated apparatus of the present invention for implementing the disclosed and novel harvesting techniques is adaptable, convenient, and useful for simultaneously processing multiple embryos. By multiple embryos, the present invention contemplates that 5,000, 10,000, 20,000, 30,000, 40,000, 50,000, 60,000, 70,000, 80,000, 90,000, 100,000, 110,000, 120,000, 130,000, 140,000, 150,000, 160,000, 170,000, 180,000, 190,000, 200,000, 210,000, 220,000, 230,000, 240,000, 250,000, 260,000, 270,000, 280,000, 290,000, 300,000 or more, or any integer in between, of embryos can be processed, e.g., washed and rinsed, per day by use of the methods and apparatuses disclosed herein.

The present invention also contemplates embryos that are prepared by any of the methods disclosed herein. In another aspect, the present invention encompasses a plant that is grown from any of the treated embryos disclosed herein.

It is to be understood that both the foregoing general description and the following detailed descriptions are exemplary and explanatory only, and are not restrictive of the invention as claimed.

BRIEF DESCRIPTION OF THE DRAWINGS

The accompanying drawings, which are incorporated in and constitute part of this specification, illustrate embodiments of the invention and together with the description, serve to explain the principles of the invention.

DETAILED DESCRIPTION

Figure 1:
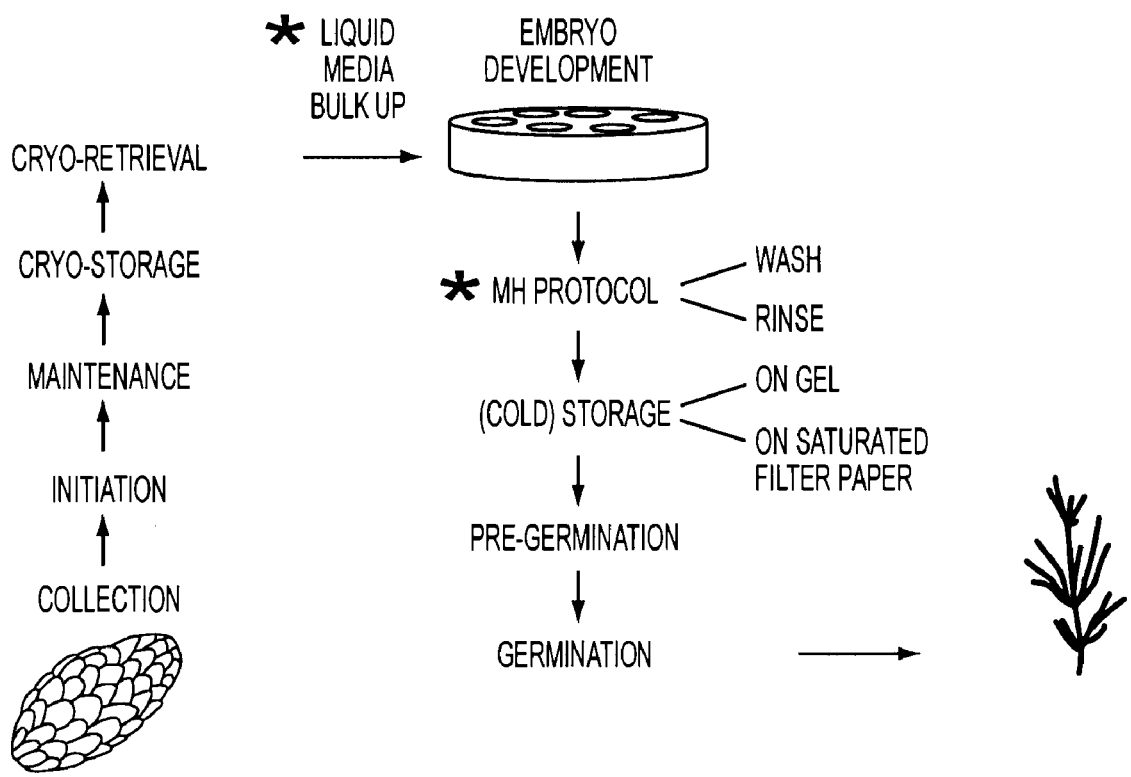
FIG. 1 is a schematic showing the steps from embryogenic initiation, liquid bulk-up, embryo development, Mass Harvesting, cold storage, pre-germination, and germination steps.

The present "Mass Harvesting" method is rapid, inexpensive, and highly efficient. The method entails washing and rinsing large numbers of plant embryos en masse, rather than individually.

After washing, the embryos are transferred to media, which has been formulated herein to increase the integrity and viability of the washed embryos over prolonged periods of time. Furthermore, as described herein, many of the Mass Harvesting and conditioning steps can be performed with liquid media, thereby eliminating certain gel-plating steps and certain storage requirements.

An apparatus is also provided herein to implement the Mass Harvesting method. It is adaptable and can be modified to run automatically, as will be described in further detail below. Briefly, however, the Mass Harvesting apparatus can increase embryo harvesting production rate to a minimum of many tens of thousands of embryos per person/day from about 2000 per day via hand harvesting. This equates to a significant increase in efficiency and an increase the number of germinants and plantable seedlings per gram of starting embryogenic cell cultures. Described below are methods for mass harvesting over 100,000, and even over a million embryos per person per day.

Any collection of embryos can be treated according to the Mass Harvesting method and apparatus. Hence, the present methods do not require a pre-treatment of embryos prior to washing, rinsing, and storing steps. It is useful, however, to appreciate certain pertinent steps and substances that aid the development of embryos. The entire process from cone collection, in the case of conifer treatment, to embryo production, storage, and germination can also be summarized as follows:

1. Cone collection and storage, usually in the cold.
2. Somatic embryogenic initiation on initiation medium.
3. Maintenance of embryogenic tissue on maintenance medium.
4. Cryogenic storage of embryogenic tissue and subsequent cryoretrieval.
5. Growth of embryogenic tissue.
6. Development of somatic embryos on embryo development medium.
7. Harvesting, e.g., via hand or via Mass Harvesting.
8. Conditioning of harvested embryos, may include pre-germination steps.
9. Germination.

Many factors in these culture conditions affect embryo production such as starting material (genotype, source, physiological stage of explant), media (minerals, plant growth regulators, supporting agents), environment (temperature, illumination properties, vessels), timing and finally interaction between all these factors.

In this regard, plant hormones play an important role in embryogenesis. Certain important substances in this respect are auxin and cytokinin.

Abscisic acid (ABA) has long been proposed to play an important role in seed maturation and the suppression of precocious germination. In developing seeds, it stimulates accumulation of reserve substances and prepares embryos for a dormancy. It also increases cold and desiccation tolerance of embryos. In maturing seeds of *P. glauca*, ABA content is the highest in megagametophytes preceding reserve deposition. Zygotic embryos develop in an environment with high ABA levels, and this hormone might be transported from megagametophytes to embryos. The ABA content varies between 7-30 µM in the embryo and in seed coat cells during seed development.

A decline in sensitivity to exogenous ABA as well as an increase in sensitivity to GAs was observed late in embryo development. Exogenously added ABA inhibits germination, however, during seed development embryos are able to germinate despite the high ABA levels. Partial drying will increase germination and decrease the ABA level. Additional drying continues to accelerate germination, but does not decrease ABA concentration further. Water availability may affect sensitivity. These changes in hormone sensitivity may play a role in germination.

ABA also has an important role during somatic embryogenesis. In somatic embryos of *Picea glauca*, for instance, ABA stimulates embryo growth and inhibit precocious germination, and in somatic embryos of *P. glauca×P. engelmannii*, ABA treatment enhances storage protein accumulation. Exogenous ABA is also capable of inducing the expression of genes coding some LEA proteins in somatic embryos of *Picea glauca* and *Pinus edulis*. Sometimes, without ABA treatment, abnormal fast-growing somatic embryos may develop. This type of somatic embryo is usually ungerminable because of inadequate preparation for germination.

Some spontaneous development of somatic conifer embryos may exist in a hormone-free medium or with PEG treatment, but in an ABA-containing medium, midway in embryo development the embryos begin to accumulate triglycerides and storage proteins and develop to mature cotyledonary somatic embryos. The first non-spontaneous maturation of coniferous somatic embryos in of *P. abies* using a low level of exogenous ABA (0.1-1 µM) was reported by Becwar M. R., et al., "A method for quantification of the level of somatic embryogenesis among Norway spruce callus lines," *Plant Cell Reports*, 6: 35-38, 1987, which is incorporated herein by reference. See also U.S. Pat. No. 5,183,757, which is incorporated herein by reference.

Higher levels of ABA were later used in embryo maturation of *P. abies* and *P. sitchensis* and up to 100 µM ABA levels are used in conifer embryo cultures. See, for instance, von Arnold S. & Hakman I., "Regulation of somatic embryo development in Picea abies by abscisic acid (ABA)," *J. Plant Physiol.*, 132: 164-169, 1988, Boulay et al., "Development of somatic embryos from cell suspension cultures of Norway spruce (Picea abies Karst.)," *Plant Cell Rep.*, 7: 134-137, 1988, and Attree S. M. & Fowke L. C., "Embryogeny of gymnosperms: advances in synthetic seed technology of conifers," *Plant Cell Tiss. Org. Cult.*, 35: 1-35, 1993.

ABA can be used in standard initiation medium. A concentration of 10 mg/l of ABA is not atypical. See, for instance, U.S. Pat. No. 5,677,185, which is incorporated herein by reference.

Gibberellins also have an important role in embryogenesis. More than 12 GAs have been identified in conifers (Wang et al. 1996). Exogenously added GAs do not have any apparent influence on development of somatic embryos probably due to sufficient synthesis of endogenous GAs.

According to the present invention, a high concentration of casein, which is a well known source of nitrogen, also is beneficial in initiation media, maintenance media, and liquid "bulk-up" media. Other sources of nitrogen may also be beneficial in such media such as glutamine.

In somatic or asexual embryogenesis, somatic cells may develop into plantlets following the same morphological steps as zygotes. In vitro somatic embryos are induced either directly from the explant or indirectly through the subculturable callus or suspension culture stage.

The first success in somatic embryogenesis among conifers was reported in 1985 for *Picea abies* (Norway spruce). See Hakman I. & von Arnold S., "Plantlet regeneration through somatic embryogenesis in Picea abies (Norway spruce)," *J. Plant Physiol.*, 121: 149-158., 1985, and Chalupa V., "Somatic embryogenesis and plantlet regeneration from cultured immature and mature embryos of *Picea abies* (L.) Karst.," *Comm. Inst. Forest Chech.*, 14: 57-63, 1985.

Somatic embryogenesis for *Pinus* is described in Gupta P. K. & Durzan D. J., "Somatic polyembryogenesis from callus of mature sugar pine embryos," *Bio/Technol.*, 4: 643-645, 1986.

Similar treatments have enabled somatic embryogenesis in several other conifer species. See Minocha S. C. & Minocha R., "Historical aspects of somatic embryogenesis in woody plants," in SOMATIC EMBRYOGENESIS IN WOODY PLANTS, Vol 1: 9-22, Kluwer Academic Publishers, The Netherlands. ISBN 0-7923-3035-8, 1995.

In vitro proliferation of conifer embryogenic cultures usually takes place on auxin and cytokinin containing culture media. Organic nitrogen, sometimes in the form of casein, is also often needed to maintain embryogenic capacity of cultures. Events in early development of a conifer somatic embryo are currently being heatedly debated. Observations range from initiation of embryo development from long, vacuolated or small, dense cytoplasmic cells via unequal division to embryonic and suspensor initials.

For effective embryo production, embryogenic tissue cultures of conifers are usually maintained on an auxin and cytokinin-containing medium, unlike many dicotyledonous embryogenic cultures, where only the auxin (usually 2,4-D) is often needed to induce embryogenesis.

For further discussion on embryogenesis, see Chapter 2 of Santanen, A., "*Polyamine Metabolism During Development of Somatic and Zygotic Embryos of Picea Abies* (*Norway Spruce*)," Academic Dissertation, University of Helsinki, Faculty of Science, Department of Biosciences, Division of Plant Physiology, November 2000.

Accordingly, it is well know how to appropriately stimulate embryogenic cultures and embryo production from a variety of plant species, and the substances that are useful for enhancing or facilitating these biological developments.

In this regard, it has been discovered herein that Mass Harvest washing and rinsing substantially removes polyethylene glycol molecules that adhere to embryo surfaces during their exposure to embryogenic development media. This is a significant discovery because the removal of polyethylene glycol via washing and rinsing eliminates several time-consuming and burdensome steps in the traditional harvesting protocol. For example, it is not necessary to store Mass Harvested embryos on gelled medium in the cold for 3-4 weeks to allow diffusion of polyethylene glycol away from the embryos.

In certain situations prior to Mass Harvesting, it is desirable to "bulk-up" embryogenic tissue before transferring onto an embryo development media. Traditionally, embryogenic tissue cultures that have been cryogenically-stored, for instance, are plated onto gelled medium and incubated for a period of time until there is sufficient growth to justify their transfer to a development medium. For instance, embryogenic tissue can be grown on polyester rafts placed on the surface of gelled medium. The tissue, plus the raft, can be frequently transferred to fresh medium, e.g., every two weeks, until a suitable tissue mass has been achieved. Cultures can typically be incubated in the dark at 25° C. The methods can be used from growing tissue derived from immature seed explants, or from tissue retrieved from cryopreservation. Suitable media are described in Table 1 and 2.

Cryostorage of cultures can use media of the standard method (using DCR liquid medium) or the alternative method formulated herein using Mi3 liquid medium with high casein and, optionally, high glutamine. The use of the Mi3 medium with increased casein and high glutamine results in significant increased growth on cultures over the standard methods. The cryostorage media also may contain two supplements sorbitol 0.4 M, and DMSO (Dimethyl Sulfoxide) 10% by volume. See, for instance, U.S. Pat. No. 5,413,930.

One may also include ABA (10 mg/liter) in the cryorecovery medium. See U.S. Pat. No. 6,682,931.

According to the present invention, however, the embryogenic tissue may be "bulked-up" or grown in a liquid version of the traditional gel medium. Consequently, eliminating the plating step helps to streamline the embryo development process and reduce costs associated with making the gel plates, for instance. In this alternative method, liquid suspension cultures are established by initially dispersing embryogenic tissue in liquid media in an appropriately sized flask or culture vessel.

Suspension cultures are incubated in the dark at 25° C. on a shaker table. Additional liquid suspension medium can be routinely added during the incubation period. Cultures can be monitored weekly until they have grown to a mass that is suitable for plating for embryo development. In this regard, the "settled cell volume" (SCV) is an indicator of liquid-suspended cell mass. In this case, when the SCV reaches at least 50% of the total suspension volume, the embryogenic tissue is at a suitable mass for plating. If additional tissue is needed, suspension cultures from single flasks can be used to establish additional flasks. Suitable media are described in Tables 1 and 2.

Embryogenic tissues that have been bulked up from either the traditional gel or the alternative liquid suspension media can be used to develop somatic embryos. An amount of the bulked up tissue can be transferred to a polyester raft and placed onto the surface of embryo development medium. The tissue and rafts can be transferred to fresh medium after a period of time. Typically, the bulked-up tissue can be stored on embryo development media for 4-6 weeks in the cold. After that time, the embryos can be Mass Harvested according to the protocols described herein.

Embryo production for individual cell lines can vary depending on the particular embryo development used. Therefore, it is possible to appropriately optimize the embryo development media for developing embryos from certain species and/or to increase the proportion of cell lines that produce embryos. In this regard, described herein are different percentages of polyethylene glycol that have been found to enhance the development of embryos from different conifer genotypes.

While these particular bulk-up and embryo development steps exemplify how embryogenic tissue can be treated prior to Mass Harvesting, the present Mass Harvesting method can be used to process any collection of embryos regardless of their prior condition of development and storage.

The Mass Harvesting procedure and apparatus may entail placing embryos onto a sieve, filter, or some other kind of mesh. The species and condition of the embryos can be taken into consideration when choosing which mesh size to use in order to capture appropriately-staged embryos. Pine somatic embryo dimensions are generally of length about 1.0 mm to about 5.0 mm and the diameter ranged from about 0.5 mm to about 2.0 mm. Accordingly, the person of skill in the art would know what would be suitable mesh sizes to use in order to manipulate embryos but prevent losing an unsuitable number of embryos by virtue of their falling through too-large openings in the mesh. Typical commercial mesh sizes have a grid with openings ranging from 500 to 1000 microns. Smaller sizes also can be used, such as those with pore sizes of 100, 150, 200, 250, 300, 350, 400, 450, 500, 550, 600, 650, 670, 700, 710, 750, and 800 microns or any integer in between. In certain cases, 800 microns is too large for certain conifer cell lines. Since high polyethylene glycol concentrations yield smaller embryos, it may therefore be desirable to use sieve size(s) that have pores smaller than 670 microns.

Sterile water is sprayed onto or poured onto the embryos on sieve to wash away embryo development media and embryogenic cellular debris. This wash step may be repeated any number of times. The washed embryos can then be transferred to media suitable for storage or germination.

Contrast this method with the traditional hand harvesting method, which entails manually picking individual embryos and placing them onto a gel medium plate, which is then stored in the cold for 3-4 weeks. In this regard, the "standard" method typically used to store and germinate harvested embryos can be described as follows:

Standard method: The standard method comprised two main steps, A and B, they are:

Step A (i) somatic embryos are harvested from embryo development plates and placed onto gelled medium for a period of time of cold storage, where the plates housing the embryos are sealed to prevent or reduce moisture loss from the plates, (ii) the embryo plates are then placed in a high relative humidity environment for a period of time, and; Step B subsequently transferred to gel embryo germination medium and singulation of somatic embryo onto fresh germination plates. Germinated embryos are then transferred to a vessel for conversion.

As evidenced from the data related in the following Examples, the present Mass Harvesting method makes certain steps of this standard method, such as the placement in a high relative humidity environment, unnecessary.

Washing and rinsing a mass of embryos can be facilitated by connecting various vessels to a water source and to a vacuum pump, which can draw a continuous and even flow of sterile water over the embryos. The Vacuum Manifold, Nalgene Product no. DS0345-0001 is an example of one type of vacuum system useful for the present invention.

Accordingly, one may devise an "embryo-washing unit," which comprises holes or at least one porous membrane or side or surface onto which embryos can be placed and into which water can flow through. For instance, the embryo-washing unit can be a cylinder within which is located a sieve or mesh or some kind of filter onto which the embryogenic tissue is placed. See the "Harvesting unit" in described in connection with Example 23.

The unit may be connected to a vacuum pump. In this regard, the unit may be connected to another device, such as a funnel, which in turn is appropriately connected to a manifold port typically used to draw a vacuum and/or fluid from a water source.

In this case, with the vacuum on, one may direct a spray nozzle at the embryos housed in the embryo-washing unit and begin washing the embryos. Debris and other materials will be drawn through the sieve or filter and the porous surface or hole of the unit and directed into a drain or container along with the waste water. The cellular debris may be sent directly to a drain instead of collecting it on a polyester trap placed within the vacuum manifold.

Once it is apparent that washing has removed most of the debris associated with the mass of embryos and the embryos have been thoroughly washed, the embryos can be removed to a clean filter paper and rinsed with sterile water.

Mass Harvesting resulted in a 12-fold increase in embryo harvesting efficiency over Hand Harvesting. One person can now readily harvest 30-embryo development plates per hour or 240-plates per day. Assuming that each plate contains 100 somatic embryos, it will amount to 24,000 embryos harvested by one person per day using Mass Harvesting procedure compared to 2000 embryos handled by one person per day with Hand Harvesting procedure.

Further, any number of wash and rinse units can be operationally linked together or connected to a vacuum manifold and water supply. In one example, the Mass Harvesting apparatus has 3 wash units and 3 collection units that operate simultaneously (see Example 23). The wash water is provided by the cold tap water system passing through an electric solenoid valve and a UV sterilizer. The solenoid valve is controlled by an adjustable timer which is activated with a foot pedal by the operator. Waste water is handled by a vacuum assisted drain line connected to house vacuum though a water/air separator (Vac-Stack). Vac-Stack collects water and drains to the building drain system without user intervention. Vacuum is used in both the wash step and the collection step.

Such an arrangement is useful for efficient Mass Harvesting of embryos for small scale clonal work and mid scale production 100K-500K plants. It follows that different magnitudes of embryo and plant production can be achieved depending on the number of discreet arrangements and apparatuses and numbers of shifts per 24-hour day are employed in any given period of time. The system is compatible with current development and conditioning methods. Efficiency of this system is over 100,000 embryos per person per day with a line that produces about 100 embryos per plate.

The apparatus also can be readily adapted for automation. Hence, one or more systems can Mass Harvest millions of embryos per day per person and automatically prepare these embryos for conditioning. The system consists of a conveyer belt on which the tissue and embryo slurry is delivered gradually using a pump. The embryos are then separated from the tissue using the sterile water spray. The washed embryos are air dried using a vacuum and dislodged into a conditioning unit.

In any of these arrangements, the embryo-washing unit can be inverted and the embryos transferred to a pre-existing polyester raft on another unit that is connected to the same vacuum manifold. This can be accomplished manually or via single-function (e.g., hard) or multi-function (e.g., programmable or flexible) automation. The embryos on the polyester raft can then be rinsed with the sterile water.

Once satisfactorily rinsed, the embryo-loaded polyester raft can then be transferred to a labeled plate of storage or conditioning media. One particularly useful conditioning medium is 2M21. See Tables 1 and 2 for the composition of 2M21.

Typically, conditioning medium is a gel encased within a dish, such as a Petri dish. The present inventive method however employs a new liquid-based version of the medium, whereby embryos are placed onto a filter paper that has been saturated with liquid medium. The embryos may be placed directly onto the saturated filter paper. Alternatively, the embryos can be placed onto a membrane, for instance, which is then placed onto the saturated filter paper, where the membrane is permeable in some respect to the liquid or to the moisture in the filter paper. In distinction to those typical conditioning procedures, therefore, the present inventive nutrient-rich, liquid-based approach neither desiccates nor starves the embryos.

To prevent loss of moisture from the Petri dish-plated form of embryos, the dish may be sealed with any one of a number of tapes or wrappings. For instance, dishes may be sealed with Nescofilm™ when harvesting is done. These plates then can be stored for a desired period of time in the cold, i.e., at 4° C., although storage under these conditions is not always necessary. For instance, it may be desirable to bypass an entire cold storage step and proceed straight to germination. It is not necessary to "starve" the embryos during cold storage or at any other point in this process.

This generic procedure of mass washing, rinsing, and transferring the embryos to storage or conditioning media can be repeated for each collection of embryos, although care should be exercised to ensure that new embryo-washing units and vacuum connections are replaced with each new cell line.

Returning to the nine-step general process for taking a conifer cone through somatic embryogenesis and germination described above, Table 1 provides the pertinent media that can be used at each particular step.

In the standard method for initiation and maintenance of embryogenic tissue, "WV5" and gelled and liquid "DCR" media are used. Embryo development medium is denoted by "MSG." The conditioning, pre-germination, and germination steps are conducted on media designated as "2M21" and "MODMS." Accordingly, the generic process can be rewritten thus:

1. Cone collection and storage, usually in the cold.
2. Somatic embryogenic initiation on initiation medium (WV5 gel).
3. Maintenance of embryogenic tissue on maintenance medium (DCR gel).
4. Cryogenic storage of embryogenic tissue (in DCR liquid) and retrieval thereof.
5. Growth of embryogenic tissue (on DCR gel).
6. Development of somatic embryos on embryo development medium (on MSG).
7. Harvesting, e.g., via hand or via Mass Harvesting.
8. Conditioning of harvested embryos (on 2M21 gel).
9. Germination (on MODMS gel).

An improved method, which is disclosed herein, includes a "liquid bulk-up" medium and other casein-rich media, "Mi3," which enhance embryogenesis. Accordingly, the new nine-step method can be rewritten thus:

1. Cone collection and storage, usually in the cold.
2. Somatic embryogenic initiation on initiation medium (WV5 gel with high casein concentration).
3. Maintenance of embryogenic tissue on maintenance medium (Mi3 gel with high casein concentration).
4. Cryogenic storage of embryogenic tissue (in Mi3 liquid with high casein concentration optionally with a genotype-specific amount of Brassinolide).
5. Growth of embryogenic tissue on cryoretrieval medium (on Mi3 gel with high casein concentration).
6. Liquid bulk-up to enhance growth of embryogenic tissue (in liquid Mi3).
7. Development of somatic embryos on embryo development medium (on MSG gel optionally with genotype-specific polyethylene glycol concentrations).
8. Harvesting, e.g., via hand or via Mass Harvesting.
9. Conditioning of harvested embryos (on a substrate saturated with 2M21 liquid).
10. Germination (on MODMS gel).

The Mi3 medium contains a base level of 500 mg/l of casein, but the total amount of casein in the Mi3 medium may be 0.5, 1.0, 1.5, 2.0, 2.5, 2.6, 2.7, 2.8, 2.9, or up to 3.0 grams per liter.

Secondly, the MSG medium, which is used for embryo development may contain varying levels of polyethylene glycol. It has been found herein that different levels of polyethylene glycol affect different Pine genotypes differently. Accordingly, it may be necessary to optimize the level of polyethylene glycol in the MSG medium to match the growth development characteristics of the genotype in question.

In this regard, the Mi3 medium also may contain an optimal amount of Brassinolide. Brassinolide, which was first isolated from rapeseed plant pollen (*Brassica napus* L.), is a naturally occurring plant steroid that promotes growth, increases yields for grain and fruit crops, and makes plants more resistant to drought and cold weather. Related compounds, called brassinosteroids, are found in a wide variety of plants, and also can be used to augment the embryo development medium.

Thirdly, the conditioning of harvested embryos is useful for preparing the embryos for germination and prolonged storage is conducted on a substrate, such as a filter paper, that is saturated with 2M21 liquid. One such method involves cold conditioning and slow moisture loss from a moist filter paper substrate during the exposure to cold. It was effective from 8 to 16 weeks. The highest germination and conversion rates were obtained when embryos were conditioned in cold for 8 weeks on moist filter paper with 1 ml of liquid 2M21 medium.

According to the present invention, all pre-germination steps and embryo germination steps can be conducted via such a medium in a single dish without touching the embryos. Thus the embryos will be touched only once when they are transferred to a sterile or non-sterile vessel in order to induce photoautotrophic conversion into planting stocks. Conversion is not limited to a particular type of vessel. Indeed, the embryos may be placed into any environment that induces their photoautotrophic conversion into suitable planting stocks. Reducing the extent of manual interaction with embryos in such fashion will significantly reduce media and labor costs for embryo germination process.

Steps 8 and 9 of the preceding modified process can also be elaborated upon as follows:

Mass Harvesting conditioning: (A) mass harvested mature somatic embryos are placed onto filter paper that has been saturated with an appropriate volume of 2M21 liquid media to facilitate saturation and placed in cold storage for a desired number of weeks, with a mechanism in place for controlling moisture loss from the filter paper over time, and (B) transferring the embryos to gel embryo germination medium and singulation of somatic embryo onto fresh germination plates. Germinated embryos are then transferred to a vessel for conversion.

Other embodiments include (1) high casein concentration in initiation, maintenance, bulk-up, and cryoretrieval media; (2) Brassinolide in cryoretrieval medium; (3) storing Mass Harvested embryos in high relative humidity without a cold storage step; (4) storing Mass Harvested embryos on filter paper saturated with liquid media in the cold, with various methods for altering the rate of moisture removal from petri dish/moistened filter paper; (5) the development of genotype-specific embryo development medium with optimal percentages of polyethylene glycol and/or Brassinolide.

Examples of the media that can be used according to the present invention are described in detail in Table 1, but their more pertinent ingredients can be summarized as follows. All of the media described herein contain inorganic salts and vitamins as detailed in Table 2. Where "casein hydrolysate" is used it is at a desired high concentration. That is, the concentration of casein hydrolysate that is detailed in Table 1 is 500 mg/l, but this is the base amount. More casein hydrolysate is typically added, e.g., an additional 0.5 to 2.5 mg/l, to the base media to provide the high concentration. The choice of how much extra casein to add is dependent on the condition of the embryos and the genotype being treated, which can be deduced empirically.

Initiation medium (gel): myo-inositol, casein hydrolysate, maltose, 2,4-D, BAP, ABA.

Maintenance medium (gel): myo-inositol, casein hydrolysate, sucrose, 2,4-D, BAP, glutamine, glycine.

Maintenance medium (liquid): myo-inositol, casein hydrolysate, sucrose, 2,4-D, BAP, glycine, activated carbon.

Bulk-up medium (gel and liquid): myo-inositol, casein hydrolysate, sucrose, 2,4-D, BAP, ABA, glutamine, glycine, activated carbon.

Embryo development medium (gel): maltose, ABA, glutamine, polyethylene glycol, activated carbon.

Conditioning medium (gel and liquid): maltose, ABA, glutamine.

Germination medium (gel): sucrose, activated carbon.

Of course, any suitable media and method for conditioning and germinating Mass Harvested embryos can be used, not only those media and methods described herein. Similarly, and as previously noted, any method of obtaining embryos, particularly somatic embryos, can be used to provide embryos for treatment according to the Mass Harvesting methodology and with the apparatus described herein.

In the southern U.S. approximately 1 billion seedlings of southern pine are produced per year. These seedlings are currently derived from seed orchard seedlings utilizing 50 years of tree improvement. Even with the increased genetic gain from this traditional tree improvement approach, the Forest Products and Paper Industry need higher yielding trees with improved wood properties. To meet industry needs requires clonal loblolly pine be implemented on large scale. Somatic Embryogenesis (SE) is the one large-scale propagation technology capable of both capturing the genetic gain from traditional tree improvement, and meeting large-scale clonal production needs of Forest Products and Paper Industry.

Although improvements have been made in conifer Somatic Embryogenesis (SE), no comprehensive approach has been formulated or developed to an operational scale that ensures the efficient capture of genotypes from conifer species. In particular, this limitation or lack of efficient genotype capture impacts implementation of SE with the Pinus species that have proven recalcitrant to efficient clonal propagation by SE.

The present invention therefore provides a combinatorial approach that enables one to take advantage of large genotype by treatment interactions in a sequential step-wise manner. The result of this approach is an optimized protocol for large-scale production that is customized for each genotype.

The conifer somatic embryogenesis is a multi-step process as described above and as illustrated in FIG. 1. The steps may be classified according to the following sequential order: culture initiation, culture maintenance or establishment, cryogenic storage, cryo-retrieval, multiplication or tissue bulk up, embryo production, embryo harvesting and conditioning, embryo germination and conversion to planting stock.

Optimization of particular parameters of any given step can improve the efficiency of that particular step in the regeneration process. And it is known that genotype by treatment interactions exist for specific steps in the somatic embryogenesis process noted above.

The present invention provides the sequential application of a combinatorial approach to exploiting the genotype by treatment interactions of multiple steps in the somatic embryogenesis process. The results reported here show that one can make very significant increases in capture and efficiency by using a combinatorial approach screening genotypes to improving the SE process in conifers.

EXAMPLES

Following is a summary of experiments described in the Examples.

1. It was demonstrated that for mass harvested somatic embryos the gelled 2M21 medium used for cold treatment and PEG block removal can be replaced with 2 ml of liquid 2M21 medium.

2. Pre germination conditioning of somatic embryos in the presence of liquid 2 M21 medium at room temperature or in cold could serve as a substitute for current high relative humidity treatment 3. The use of 3M-filter tape allowed pre-germination conditioning of somatic embryos by avoiding moisture condensation in Petri plates at both room temperature and in cold.

4. Cold treated somatic embryos conditioned in the presence of liquid 2M21 medium can be effectively induced to begin the germination process by addition of 2 ml liquid MODMS1 germination medium 5. Cold storage of embryos on a new liquid 2M21 medium showed potential to extend embryo storage to at least 24 weeks while retaining good embryo quality, whereas storage of embryos on gelled 2M21 medium per the standard method decreased embryo quality after 16 weeks or longer 6. The properly conditioned germination ready somatic embryos are amenable to extended cold storage by double wrapping with 3M-filter tape and Saran wrap.

7. An experiment comparing different embryo conditioning methods showed that a "new" cold conditioning method provides a reasonable alternative to the standard cold plus high relative humidity conditioning protocol.

8 Storing harvested embryos on gelled medium during the cold conditioning phase followed by holding embryos in sealed vessel at warmer temperatures worked as effectively as a standard method that necessitates holding embryos over water in vessels during the warm phase. The new alternative method is simpler and more amenable to large-scale conditioning for commercial production.

9. Germination and conversion were similar or slightly higher for several new cold conditioning treatments compared to the standard method.

10. Addition of 1 ml liquid 2M21 medium added to filter paper may be better than 2 ml for the 8 week duration of cold conditioning.

11. The cold conditioning method noted here results in slow moisture loss during the extended (8 to 16 weeks) depending on the volume of water added to the filter paper. This allows for flexibility in scheduling when to go to germination.

12. A liquid medium for growing embryogenic tissue that comprises a high concentration of casein.

13. An improved method for retrieving embryogenic tissue from cryostrorage by including either or both high casein and brassinolide in the tissue recovery medium and tissue bulk up medium.

14. Using a battery of media at several sequential steps, results in a combinatorial approach to increase the likelihood of maximizing the number of commercial candidate cell lines for scale-up, and also increasing efficiency and reducing cost for implementing the somatic embryogenesis process.

All of the media that are referenced below, e.g., "WV5," "DCR," "Mi3," "MSG," "2M21," and "modMS" are detailed in Tables 1 and 2.

Example 1

Mass Harvesting of Somatic Embryos

Procedure

Following is one strategy for collating, washing, and rinsing embryos according to the "mass harvesting" concept presently described.

Place the embryo-washing unit on top funnel on washing side (washing and rinsing sides are determined by preference) of the manifold port.

Working with a single line at a time, load embryos into the washing unit using a spatula.

Turn on vacuum port to washing side of manifold.

Position spray nozzle over embryo-washing unit and depress foot pedal control to begin washing.

Wash embryos until all suspensor tissue is separated from the embryos (embryos will remain on mesh surface of the embryo-washing unit while the tissue is washed into drain bottle. Release foot pedal and turn off vacuum.

Place a polyester raft in the funnel on the rinsing side of the manifold port.

Once washing is complete and excess water has drained, invert embryo-washing unit and transfer to the rinsing side of the manifold.

Position spray nozzle over embryo-washing unit and depress foot pedal control to begin rinsing embryos onto polyester raft.

Remove polyester raft from washing side of manifold and replace.

Transfer the embryo-washing unit back to washing side of the vacuum manifold.

Lift the embryo loaded polyester raft and transfer to a labeled plate of 2M21 media.

Wrap the plates with Nescofilm™ when harvesting is done.

Repeat this procedure for the remaining plates.

Change funnel tops and embryo-washing unit with each new cell line.

Media

See Tables 1 and 2 for detailed recipes for various media used in the present invention.

Materials 2.95 inch circular polyester raft supports with 35 micron pores (SEFAR 07-33/10)

Steri 350™ heat sterilization device

Dumont SS non-magnetic pointed forceps, 5.5" long, 6 inch dissecting forceps and spatula Nescofilm™ strips or 6"×5" perforated Saran plastic wrap Polypropylene Buchner funnels—90 mm I.D. tops (cut down to ½ inch height) with 71 mm long stems (fitted with #8 black rubber stoppers)

Nalgene 3 port stainless steel manifold that holds 3 Buchner funnel stems simultaneously (center port is not used) and has individual stopcock controls for applying a vacuum (equipped with the appropriate tubing for connecting to waste Carboy and the vacuum supply)

Manostat 'Kate' Varistaltic Dispenser with appropriate tubing connected RO water source Carboy Pall 22 um in-line re-autoclaveable filter and appropriate tubing Embryo Washing Unit Modified SprayDoc spray nozzle and fan spray tip 1 liter Corning bottle for spray nozzle storage Disposable petri plate for used polyester raft storage Other typical supplies required for tissue culture work may also be necessary, such as 3"×3" gauze sponges saturated with 95% ETOH, 70% ETOH, masks, gloves, etc.

Example 2

Embryo Germination: Comparison of Mass Harvesting and Hand Harvesting Methods for Loblolly Pine To test the utility and efficiency of mass harvesting procedure, we established an experiment to do a side-by-side comparison of Hand Harvesting and Mass Harvesting methods on embryo germination and conversion. Since the washing procedure used for Mass Harvesting of embryos helps in removal of PEG, in this experiment we are also looking at the possibility of eliminating PEG block removal treatment for further simplification of procedure and cost reduction.

Standard method: (A) (i) mature somatic embryos are harvested from embryo development plates and placed onto gelled 2M21 medium for 4 weeks of cold storage, where the plates housing the embryos are sealed to prevent or reduce moisture loss from the plates, (ii) the embryo plates are then placed in a high relative humidity environment for 3 weeks, and (B) then transferred to gelled embryo germination medium and singulation of somatic embryo onto fresh germination plates. Germinated embryos are then transferred to a vessel for conversion.

The experiment consists of four treatments.

Treatment 1 Hand Harvesting embryos on polyester raft placed on 2M21 medium

Treatment 2. Hand Harvesting embryos on moist filter paper placed in sterile petriplates Treatment 3. Mass Harvesting embryos polyester raft placed on 2M21 medium Treatment 4. Mass Harvesting embryos on moist filter paper in sterile petriplates The embryos used in this experiment were harvested from 10-12 week-old development plates from 20 different cell lines. Each treatment consists of four replicated plates for every cell lines. After four weeks of cold treatment at 4° C., the embryos from each treatment will be carried through to conversion according to the standard method. Observations were recorded on embryo germination and conversion efficiency.

For this experiment, the embryo germination data is presented in Table 3. The actual number of germinants transferred to magenta boxes was counted for each replicate. This number was then multiplied by an appropriate factor to get the total number of germinants per gram of tissue used for embryo development plates.

Comparison of Hand Harvesting (Treatment 1) and Mass Harvesting procedures (Treatment 3) clearly show a significant increase in number of germinants transferred to magenta boxes when Mass Harvesting procedure was used. It is also apparent from the data that use of moist filter paper in place of 2M21 medium resulted in a sharp decline in number of germinants transferred to magenta boxes with both Hand Harvesting and Mass Harvesting procedures. However, it is worth noting that a combination of Mass Harvesting and moist filter paper produced as many germinants as in control (Treatment 1 vs. 4).

Table 3 shows the breakdown of number of germinants transferred to magenta boxes for all 20 cell lines used in this experiment. Overall, Mass Harvesting produced higher number of germinants per gram of tissue in 16 out of 20 cell lines tested.

Example 3

Embryo Conversion: Comparison of Mass Harvesting and Hand Harvesting Methods for Loblolly Pine This experiment was designed to compare the efficiency of mass harvesting procedure with hand harvesting of loblolly pine somatic embryos from 20 different cell lines. Each treatment consisted of four replicated plates for each cell line. Somatic embryos were harvested from each plate using both procedures and treated as in the standard method as exemplified in steps A and B described above.

Observations were recorded on actual number of rooted germinants transferred to magenta boxes for each replication. The germinants were than allowed to grow in magenta boxes in culture room under ambient temperature and light conditions for 12-14 weeks to obtain the plantable somatic seedlings. After 14 weeks, all seedlings were pulled out of magenta boxes for each replication and divided into two categories, i.e. plantable and non-plantable somatic seedlings.

The plantable seedlings had a well developed root system and a visible distinct stem growth. The non-plantable seedlings were those that either did not grow or had no visible stem and root growth. The somatic seedlings that had a curved or coiled stem were classified as non plantable seedlings irrespective of their shoot and root growth.

The observations were recorded on total number of seedlings for each replication (representing the number of germinants transferred to magenta boxes) and the number plantable seedlings. Root and shoot length for each plantable somatic seedling was also measured.

The embryo germination data presented in Table 4 shows that on an average the Mass Harvesting procedure resulted in a 1.7 fold increase in total number of germinants transferred to magenta boxes per gram of embryogenic tissue compared to Hand Harvesting. 16 of 20 cell lines tested produced higher number of germinants when Mass Harvesting procedure was used.

The results for plantable somatic seedlings for each treatment are presented in Table 5. It is evident from the data that on an average Mass Harvesting resulted in a 1.3 fold increase in number of plantable somatic seedlings per gram of embryogenic tissue. Based on the embryo germination and conversion of germinants into plantable somatic seedlings we conclude that Mass Harvesting procedure can be used in place of Hand Harvesting of somatic embryos for scale up production of somatic seedlings.

The Mass Harvesting procedure is suitable for harvesting embryos from multiple plates of single cell line.

Shoot and root length of each harvested seedling was also measured. There was no difference in average shoot length for mass harvested somatic seedlings compared to their hand harvested counterparts. The shoot length varied among cell lines and ranged between 3-6 centimeters. For the hand-harvested seedlings the average shoot length was 4.27 centimeters and for the mass harvested seedlings the average shoot length was 4.26 centimeters.

On an average the roots of Hand Harvested plantable somatic seedlings was slightly longer compared to Mass Harvested seedlings but the difference does not appear to be significant. That is, the average root length for Hand Harvested seedlings was 4.93 centimeters versus 4.45 centimeters for the Mass Harvested seedlings. There is a positive correlation between shoot and root length of the somatic seedlings for each cell line. In general, if a cell line had better shoot growth, it also had well developed roots. These results demonstrate that Mass Harvesting yields plantable somatic seedlings comparable in vigor and growth to those obtained with Hand Harvesting.

Example 4

Effect of Mass Harvesting on Peg Block Removal from Somatic Embryos of Loblolly Pine Polyethylene glycol (PEG) is a high molecular weight osmoticum agent, which adheres to the surface of mature embryos. The use of PEG in embryogenic-related media, therefore, interferes with embryo germination. To address this concern and to overcome the PEG-induced embryo germination interference, here, embryos are transferred to a non-PEG medium and stored in cold for four weeks.

Mass Harvesting involves washing embryos with sterile water, which should wash away any PEG that is adhered to the outer surface of the somatic embryo. Consequently, Mass Harvesting results in better embryo germination and conversion:

Hand Harvesting: somatic embryos were hand harvested onto polyester rafts placed on two filter papers saturated with 2 ml of water. Petri plates containing embryos were sealed with Nescofilm™ and stored at 4° C. for 4 weeks. The embryos were then subject to high relative humidity for 3 weeks prior to germination. See U.S. Pat. No. 5,183,757.

Mass Harvesting: somatic embryos were mass harvested onto polyesters rafts. The good embryos (approximately same number as in Hand Harvesting) were then hand picked and placed onto two filter papers saturated with 2 ml of sterile water. Petri plates containing embryos were sealed with Nescofilm™ and stored at 4° C. for 4 weeks. The embryos were then subject to high relative humidity for 3 weeks prior to germination.

The experiment was setup with four different cell lines. Each treatment consisted of three replicated plates for every cell line. Data was collected on percent embryo germination.

The results presented in Table 6 show that average percent germination for Hand Harvesting and Mass Harvesting was comparable.

The results also indicate that cold storage of embryos on moist filter paper could serve as a PEG removal treatment.

Example 5

Effect of Mass Harvesting on Peg Removal from Somatic Embryos of Loblolly Pine

A follow up experiment to that described in Example 4 was performed without the cold treatment step:

Hand Harvesting, no cold storage with high relative humidity: somatic embryos were hand harvested onto polyester rafts placed on two moist filter papers. The polyester rafts were blotted dry and subjected to high relative humidity for 3 weeks prior to germination.

Mass Harvesting, no cold storage with high relative humidity: somatic embryos were mass harvested onto polyesters rafts. The good embryos (approximately same number as in Hand Harvesting) were then hand picked and transferred onto fresh raft placed on moist filter papers. The rafts were blotted dry and subjected to high relative humidity for 3 weeks prior to germination.

The experiment was setup with four different cell lines. Each treatment consisted of four replicated plates for every cell line. Data was collected on percent embryo germination.

The results presented in Table 7 show average percent germination for Hand Harvesting and Mass Harvesting embryos. In the absence of a washing step and without the cold storage phase, none of Hand Harvested embryos, from any cell line, germinated. On the other hand, the Mass Harvested embryos germinated at fairly high frequency even though the embryos were not stored in the cold.

Example 6

Effect of Casein Level on Growth Pine Somatic Embryogenic Cultures

This experiment optimized the rate of embryogenic culture growth as a function of casein concentration. It is important to rapidly bulk up the SE cultures in order to have sufficient tissue for cryogenic storage. It is commonly known that plant tissue cultures, in particular conifer embryogenic cultures, frequently lose regeneration capacity during prolonged time in culture. Therefore, rapid tissue bulk up is exceedingly advantageous. A treatment that improves bulk up: 1) provides more tissue for cryopreservation, where multiple samples are needed for banking, and/or 2) provides a required amount of tissue in less time. Here we quantified the effect of casein level on tissue growth after the initiation and maintenance phase of culture growth. Five casein levels were tested ranging form 0.5 g/l (a level used by those skilled in conifer somatic embryogenesis) to as high as 2.5 g/l.

It was found herein that higher levels of casein (an enzymatic hydrolyzed casein, one of which is Sigma #C4523 "N-Z-Case TT") had a positive effect on tissue growth. The recorded criteria for judging the effects of casein concentration were the culture weight and frequency of cultures that reached 1 gram after 12 weeks in culture.

The effect of high casein, however, varied with family. With family H, optimum casein levels were 1.0 and 1.5 g/l. With family H the optimum casein levels were 1.5 and 2.0 g/l. In family H high casein during 8 weeks on initiation medium and 4 weeks on maintenance medium nearly doubled the average tissue mass and increase the frequency of culture reaching at least 1 gram from 46% (for 0.5 g/l low casein control) to 78% for the 2.0 g/l high casein treatment (a 70% improvement).

One report tested higher casein levels in SE of a conifer fir species and found increased growth on 1.0 to 1.5 g/l casein. See K. Szczygiel, Abstract, International Conference on: wood, breeding, biotechnology and industrial expectations, 9th Conifer Biotechnology Working Group and IUFRO, Jun. 11-14, 2001.

Cultures were initiated from immature seed of families I and H as described in U.S. Pat. No. 5,677,185, which is incorporated herein by reference. The formulation of the initiation medium was WV5 is detailed in Tables 1 and 2. WV5 medium is also described in U.S. Pat. No. 5,534,433, which is incorporated herein by reference. In this experiment, the WV5 has a total concentration of casein hydrolysate (Sigma #C4523 "N-Z-Case TT") as follows: Trt 1=0.5 g/l (control), Trt 2=1.0 g/l, Trt 3=1.5 g/l, Trt 4=2.0 g/l, Trt 5=2.5 g/l.

After 8 weeks embryogenic tissue from responsive explants was transferred to maintenance medium for bulking up. The culture weight data was measured after two passages of 2 weeks per passage on maintenance medium treatments.

The formulation of the Mi3 maintenance medium is listed in Tables 1 and 2 with one of the five total casein hydrolysate levels as used in the initiation phase of this experiment noted above.

In this experiment embryogenic cultures from each initiation treatment were divided (split) into two equal parts, with one part going to the control level of casein (0.5 g/l) and the other part going to the same level of casein from which it came (or one higher level if it came from the control). For example, cultures from initiation Trt 4 (2.0 g/l casein) were split with half going to the maintenance control level of casein (0.5 g/l, Trt 1) and half going to the same maintenance level as initiation (2.0 g/l). The procedures for splitting were that the tissue was dispersed in 1 ml diluent (Mi3 medium with out gelling agent or casein) and divided into two 0.5 ml aliquots for transfer to polyester rafts on the appropriate gelled maintenance medium. After 4 weeks on maintenance medium cultures the weight of each culture was measured.

Higher levels of casein during the pre-cryo maintenance phase generally had a positive effect on the average culture weight and the frequency cultures reached 1 gram fresh weight in both families tested (Table 8). Notice how culture transferred to a higher level of casein always had higher weights and higher frequency of reaching at least 1 gram. The effect of casein depended on the genetic family.

With family I the highest average culture weights were obtained from treatment combinations that had either 1.0 or 1.5 g/l casein in both the initiation and maintenance medium.

With family H higher levels of casein had an even more pronounced effect on both culture weight and frequency of cultures reaching 1 gram compared to family I.

With family H the highest average culture weights were obtained from treatment combinations that had either 1.5 or 2.0 g/l casein in both the initiation and maintenance phase. The same two treatment combinations also had the highest frequency of lines that reached 1 gram with family H.

One of the more effective treatment combinations with family H, which had 2.0 g/l casein in both the initiation and maintenance phase, significantly increased (p<0.001) the frequency of cultures reaching 1 gram from 46 to 78% and approximately doubled the average culture weight in comparison to the control.

Accordingly, high levels of casein can improve both initiation and maintenance in loblolly pine. The results suggest that having high casein is important in the post initiation, i.e., the maintenance, phase of embryogenesis.

Example 7

Effect of High Relative Humidity

The experiment consists of following five treatments:

Mass Harvesting (Treatment 1): Mass Harvesting embryos on polyester raft as in steps A and B of the standard method.

Mass Harvesting with L2M21 and high relative humidity (Treatment 2): Mass Harvesting embryos on polyester raft, placed on two sheets of filter paper saturated with 1.5 ml of liquid 2M21 medium, apply high relative humidity and treated according to step B of the standard method.

Mass Harvesting with L2M21, no high relative humidity (Treatment 3): Mass Harvesting embryos on polyester raft, placed on two sheets of filter paper saturated with 1.5 ml of liquid 2M21 medium, skip high relative humidity and treated according to step B of the standard method.

Mass Harvesting no L2M21 but with high relative humidity (Treatment 4): Mass Harvesting embryos on polyester raft, placed on two sheets of filter paper saturated with 1.5 ml of sterile water, apply high relative humidity and treated according to step B of the standard method.

Mass Harvesting no L2M21, no high relative humidity (Treatment 5): Mass Harvesting embryos on polyester raft, placed on two sheets of filter paper saturated with 1.5 ml of sterile water, skip high relative humidity and treated according to step B of the standard method.

A total of 10 different cell lines were used in this experiment. Only 9 cell lines were carried through to germination. Each treatment consisted of four replicated plates for every cell line used. The actual number of germinants transferred to magenta boxes was counted for each replicate. This number was then multiplied by an appropriate factor to get the total number of germinants per gram of tissue used for embryo development plates.

On average, a higher number of germinants were produced per gram of embryogenic tissue when gelled 2M21 medium was used during the cold treatment phase compared to liquid 2M21 medium for Mass Harvested embryos. See Table 9. See Tables 1 and 2 for the ingredient for 2M21 medium (also referred to as the "conditioning medium").

The use of sterile water in place of 2M21 liquid medium further reduced the average number of germinants per gram of tissue. This suggests that the underdeveloped embryos collected via mass harvesting benefits from the nutrient medium provided during the cold treatment. There is a line by treatment interaction but, in general, these differences are consistent when we compare individual cell lines for these treatments (Table 9).

It may be possible to replace the gelled 2M21 medium with liquid medium for Mass Harvesting. Furthermore, since the liquid medium in the Petri-plate simulates the high relative humidity environment, it also is possible to eliminate the high relative humidity treatment. The support for this observation comes from the comparison of the high relative humidity treatments in this experiment. The high relative humidity treatment seems to have a slight advantage over no high relative humidity for embryo germination.

Example 8

Embryo Germination and Conversion: Effect of Alternative Pre-Germination Treatments on the Germination of Loblolly Pine Somatic Embryos The results of Example 7 led to further experiments to determine whether the high relative humidity could be eliminated from the Mass Harvesting protocol. Since only 1.5 ml of liquid medium per plate was used, a hypothesis was that the difference between gelled and liquid medium treatments on germination may be due to lower amount of nutrients and hormones available to embryos on liquid medium during the cold treatment.

2.5 ml of liquid 2M21 medium was used to supplement for nutrient deficiency. However, this amount of liquid, without any humidity treatment, left the embryos too wet and they failed to germinate upon transfer to germination medium. Accordingly, if higher volume of liquid medium is used, the embryos need additional conditioning for eliminating the extra moisture from the Petri plates.

This extra conditioning step can be achieved by transferring the cold treated embryos to room temperature for two weeks prior to germination. The results of this preliminary experiment are shown in Table 10.

These results suggested that conditioning of somatic embryos at room temperature for 2 weeks after cold treatment on liquid 2M21 medium was more effective for embryo germination than conditioning at room temperature prior to cold treatment. The following conditions tested the effect of embryo conditioning at room temperature and in cold as an alternative to high relative humidity:

Trt 1: control, 4 weeks in cold on gelled 2M21 medium with 3 weeks high relative humidity in Microtip boxes followed by germination.

Trt 2: 4 weeks in cold on 2 ml of liquid 2M21 medium with 2 weeks at room temperature followed by germination.

Trt 3: 4 weeks in cold on 2 ml of liquid 2M21 medium followed by germination.

The embryos for this experiment were harvested from 6 different cell lines. Each treatment consisted of 4 replicated plates for each cell line. The embryos were mass harvested for all treatments. For treatments 2 and 3 the polyesters containing embryos were placed on 2 sheets of filter papers saturated with 2 ml of liquid 2M21 medium. All plates were wrapped with Nescofilm™.

The results presented in Table 11 shows that embryo germination for all three treatments was comparable. This confirmed our earlier observation that conditioning of cold treated embryos (in the presence of 2 ml liquid 2M21 medium) at room temperature for two weeks can serve as a substitute for high relative humidity treatment. It was rather surprising to see that conditioning of embryos in cold in the presence of 2 ml of liquid 2M21 medium was equally effective for germination. It was also noticed that conditioning of embryos in cold or at room temperature results in synchronized embryo germination. Preliminary results from our more recent probe experiment suggests that somatic embryos preconditioned in cold or room temperature can be effectively re-hydrated in the same dish by adding 2 ml of liquid modMS1 germination medium. See Tables 1 and 2 for details of the modMS media (also referred to as the "germination medium").

In all of the above described experiments the somatic embryos were Mass Harvested. The Petri plates containing somatic embryos were wrapped with Nescofilm™ and stored at 4° C. in the refrigerator for cold treatment. Even though we were able to achieve conditioning of somatic embryos in cold with 2 ml of liquid 2M21 medium that resulted in germination frequency comparable to control, most of the liquid in the Petri plate condensed on lid or sides. The rate of condensation also varied from plate to plate creating different micro environment in each plate.

Additionally, if the Petri plates were shaken during handling the condensed liquid was reabsorbed in the filter paper creating unfavorable condition for embryo germination. To overcome the condensation problem, we first tried placing a slightly larger dry filter paper in the Petri plate lid. This helped in reducing the condensation on the lid to some extent but more moisture condensed on the side of the Petri plates.

As a second option, the effect of three different wrapping tapes on moisture condensation in Petri plates was tested. Two different temperature settings also were investigated. The Petri plates containing two sheets of filter paper and a polyester saturated with 2 ml of liquid were wrapped with 3M filter tape, Nescofilm™ and Saran wrap and placed at 4° C. and 7° C. The Nescofilm™ and Saran wrap were also tested with 2 and 4 holes made on the side of Petri plates with a sterile spatula. The moisture loss from each Petri plate after 4 weeks was used as a measure for reduced condensation.

3M filter tape was more effective in preventing condensation at both temperature settings compared to Nescofilm™ and Saran wrap. The holes in the Nescofilm™ and Saran wrap helped with the escape of moisture but were not as effective as 3M filter tape. The moisture loss at 4° C. was more rapid than 7° C. This could be due to the difference in relative humidity in both chambers.

These results suggest that the use of 3M filter tape may help with pre germination conditioning of the embryos by regulating the moisture loss and avoiding moisture condensation in Petri plates at both room temperature and in cold. Since Saran wrap did not allow any appreciable moisture loss at both temperature settings, we may be able to store properly conditioned germination ready embryos by double wrapping with 3M filter tape and Saran wrap.

The data presented in these experiments suggests that we can replace gelled 2M21 medium with 2 ml of liquid medium for feeding, cold storage and PEG block removal of mass harvested somatic embryos. The use of 3M filter tape allows the pre-germination conditioning of somatic embryos. The somatic embryos conditioned at room temperature or in cold were able to germinate as well as control embryos. These preliminary results also indicate that conditioned somatic embryos can be effectively induced to begin the germination process by adding 2 ml of liquid MODMS1 germination medium and can possibly be germinated in the same dish.

Based on these observations, therefore, it is likely possible to achieve feeding, cold treatment/PEG block removal, high relative humidity, and possibly embryo germination in the same dish. In addition, the conditioning of somatic embryos in liquid medium may allow the cold storage for extended period by double wrapping with 3M filter tape and Saran wrap. This simplified embryo germination procedure was tested in a large replicated experiment.

Example 9

Embryo Germination and Conversion: Effect of Medium Treatment and Short-Term Storage Time on Germination and In Vitro Conversion of Cold Stored Embryos The purpose of this experiment was to test the effect of two different methods of holding embryos during short term cold (4° C.) storage on subsequent germination and in vitro conversion. Short term refers to 4, 6 and 8 weeks in cold storage. The embryos used in this experiment were Mass Harvested from 8 different cell lines from two families. Each line had 6 plates of cold stored (CS) embryos. The two cold storage treatments were (treatment no. 1 is exemplified by steps A and B of the standard method:

1. 2M21 (gel): Embryos on polyester membrane on surface of gelled 2M21 medium
2. 2M21 (liquid): Embryos on filter paper moistened with 2.5 ml of liquid 2M21 medium After cold-storage for 4, 6 or 8 weeks, according to either Treatment 1 or 2, embryos were exposed to high relative humidity treatment using microtip boxes wrapped with Nescofilm™ held at 24° C.±2° C. for 3 to 4 weeks. The embryos were induced to begin germination on ModMS germination medium (Table 1) for 5 days and then singulated. Germinating embryos were counted (those with visible root development) and transferred individually to magenta boxes. Plantable germinants were counted (those with both root and shoot epicotyl growth) to obtain in vitro conversion data. The results are summarized in Table 12.

Embryos stored in the standard method on gelled (2M21) medium had similar germination levels at 4, 6 and 8 weeks (352, 342 and 372 germinants per gram tissue, respectively). Embryos stored on filter paper moistened with liquid (2M21) medium had reduce germination after 4 and 6 weeks (202 and 253 germinants per gram tissue, respectively), but germination levels were similar to the standard method at 8 weeks (365 germinants per gram tissue). Thus, there appeared to be an interaction between the length of time in storage and the method of storage (gelled versus liquid medium) as to the effect on germination.

Embryos stored in the standard method on gelled medium had only slightly reduced in vitro conversion (average plantables per gram tissue) at 6 and 8 weeks CS compared to the control 4 week treatment. By contrast, embryos stored on filter paper moistened with liquid medium had higher in vitro conversion at 8 weeks CS (170 plantables per gram tissue) compared to the shorter CS times of 4 and 6 weeks (102 and 101 plantables per gram tissue, respectively). Thus, there also appeared to be an interaction between the length of time in storage and the method of storage as to the effect on in vitro conversion.

These results point to a potential advantage of using liquid media for longer term cold storage of embryos. That is, after 8 weeks similar germination, increased conversion is obtained using the liquid medium method for cold storage of embryos compared to the same cold storage time using the standard gelled medium method.

Shorter-term cold storage of embryos using liquid media resulted in the highest conversion rates (average of 170 plantables per gram tissue) after 8 weeks cold storage. By comparison, this was a slight improvement in conversion over the 4 week standard cold storage method on gelled medium (average of 158 plantables per gram tissue) (Table 12).

The results obtained in this short term storage experiment reported here generally agree with the results obtained in long-term storage of embryo experiments. That is, the use of filter papers moistened with liquid appears to have a positive effect on germination and in vitro conversion that is manifested under longer-term storage times.

Example 10

Embryo Germination and Conversion: Study of Embryo Storage Capabilities on Gelled 2M21 Media in the Dark at 4° C.

Embryos were Mass Harvested, placed on gelled 2M21 medium and kept in the cold storage (CS) at 4° C. for 4, 16 & 24 weeks. After their respective treatments they continued on with the standard operating procedures for germination. The setup required 5 cell lines and each treatment consisted of 4 replicates per cell line, each of which was exposed to steps A and B) of the standard method, although the length of time of cold storage under step A was varied as described below:

Control: Mass Harvesting embryos on S2M21, 4-weeks cold storage 16 wk CS: Mass Harvesting embryos on S2M21, 16-weeks cold storage 24 wk CS: Mass Harvesting embryos on S2M21, 24-weeks cold storage The data in Table 13 show that germination of somatic embryos stored for 16 weeks on gelled 2M21 medium (16 wk CS) was comparable to control (4 wk CS). The percent germination in this experiment are lower than usual because all mass harvested embryos were counted for each replicated plate rather than harvestable embryos counted in the standard germination test. This confirms the previous observation that somatic embryos can be stored for 16 weeks on gelled 2M21 medium without much adverse effect on germination. However, it was noticed that 16 week embryos looked abnormally swollen and were a pale yellow with brown suspensor ends. Following high relative humidity, these embryos geminated and transferred to magenta boxes for conversion. The 24 week CS treatment resulted in further deterioration in embryo quality and poor germination compared to 16 week CS treatment.

Example 11

Embryo Germination and Conversion: Study of Embryo Storage Capabilities on Liquid 2M21 Media in the Dark at 4° C.

Embryos were Mass Harvested onto polyesters rafts that were placed on two filter papers saturated with liquid 2M21 medium (2.5 ml) and stored for 4, 16 and 24 weeks. Except for the control, a 90 mm filter paper was added to the lid at 4 weeks; plates were rewrapped and then returned to CS for their respective treatments. The 90 mm filter paper served a dual purpose. It absorbed moisture vapor within the plate and in doing so it created a high relative humidity environment without allowing the embryos to come in direct contact with water (condensation allows moisture to move from the feeding surface to the upper section of the plate, i.e., modified high relative humidity). All plates were wrapped with Nesco-film™ to prevent any moisture loss. The setup required 5 cell lines representing 3 families and each treatment consisted of 4 replicates per cell line, each of which was exposed to steps A and B of the standard method, although the length of time of cold storage under step A was varied as described below and the state of the medium is liquid and not gelled:

Control: Mass Harvesting embryos on liquid 2M21

16 wk CS: Mass Harvesting embryos on liquid 2M21, 16-weeks cold storage 24 wk CS: Mass Harvesting embryos on liquid 2M21, 24-weeks cold storage Table 14 shows that embryos cold stored for 16 weeks on liquid 2M21 medium were comparable to control embryos and did not require high relative humidity treatment for germination. As opposed to 16-week-old embryos stored on gel 2M21 medium, the embryos stored on liquid 2M21 looked normal and produced good quality germinants. These germinants have been transferred to magenta boxes for conversion. The embryos from 24 wk CS treatment on liquid 2M21 medium look as good as 16 wk CS treatment. These observations suggest that for storage of embryos beyond 16 weeks the modified procedure (L2M21 medium+filter paper) may be desirable.

Example 12

Embryo Conditioning: Test of Different Embryo Conditioning Methods and Times

The purpose of this experiment was to test cold conditioning beyond 12 weeks using a cold conditioning method that allows for slow moisture loss from the moist filter paper substrate. A second parameter tested was the volume of liquid on the filter paper in an attempt to keep the duration of the conditioning more in line with an 8 week time frame typically used in the standard method.

Table 15 has a detailed description of the components of each of the 10 conditioning treatments tested in this experiment.

Briefly, somatic embryos from five J cell lines were Mass Harvested, pooled and distributed to ten conditioning treatments as described in Table 15. Treatments 1-4 represent the standard method including steps (A) and (B), but with varying lengths of time of cold storage under step (A). Treatments 5 to 10 represent modifications to step (A) of the standard method. Specifically, under Treatments 5-10, the cold storage procedure in (A) has been modified to control moisture loss and uses saturated filter paper as the conditioning substrate instead of the gel medium of the standard method. In this regard, the following is a generic description of the alternative treatment protocol ("Mass Harvesting conditioning") as deduced by the Treatment 5-10 experiments:

Mass Harvesting conditioning: (step A) mass harvested mature somatic embryos are placed onto filter paper that has been saturated with the desired volume (1 or 2 ml in this experiment) of 2M21 liquid media and placed in cold storage for the desired time (8 to 16 weeks in this experiment), with a mechanism in place for controlling moisture loss from the filter paper over time, and (step B) transferring the embryos to gelled embryo germination medium and singulation of somatic embryo onto fresh germination plates. Germinated embryos are then transferred to a vessel for conversion.

The specific conditions for Treatments 1-10 are as follows:

Treatment 1 was the standard method used for plant production, having both a cold conditioning and a high relative humidity treatment totaling 7 weeks.

Treatments 2, 3 and 4 were similar to Treatment 1 but varied in time of cold storage of 11, 15 and 19 weeks, respectively.

Treatments 5 to 10 were cold conditioning methods that varied in total duration from 8 to 16 weeks in the cold to induce gradual moisture loss from the moist filter paper substrate saturated with either 2 ml (Treatments 5, 6 and 7) or 1 ml (Treatments 8, 9 and 10) of liquid medium.

Table 16 summarizes the in vitro germination and conversion results for the embryos conditioned in the 10 different treatments.

Table 17 summarizes the moisture contents of the conditioning plates containing embryos and the moisture content of the embryos after each conditioning treatment. The complete data set for germination and conversion is in Table 18.

The desired target moisture loss from each plate during the cold conditioning is about 1.5 grams, or about 75% of the 2 ml liquid added to the filter papers in treatments 5, 6 and 7. The percentage water loss from treatments 5, 6 and 7 ranged from 40% (Trt 5), 68% (Trt 6) to 81% (Trt 7) (Table 17). Thus, treatments 6 and 7 which cold stored the embryos for 12 and 16 weeks respectively were near the targeted 75% water loss per plate.

Plates in treatments 8, 9 and 10 had only 1 ml liquid added to the filter paper substrates prior to cold conditioning. Water loss during the cold conditioning ranged from 81% (8 weeks, Trt 8), 107% (12 weeks, Trt 9) and 117% (16 weeks, Trt 10) (Table 17). Thus, treatment 8 that had 1 ml liquid per filter paper had about the targeted moisture loss (target 75%), whereas the longer conditioning treatments, for 12 and 16 weeks, lost more liquid than was added to the filter paper.

The embryos in treatments 1 to 8 had similar post-conditioning moisture contents, ranging from 63% to 87% (Table 17). Whereas the moisture content of embryos after conditioning on treatments 9 and 10 was much lower (44% and 21%). This reflects that for treatments 9 and 10, which received the extended periods of time (12 and 16 weeks), moisture is lost from both the liquid added to the filter paper and the embryos on the raft.

Treatments 1 and 2, which had relatively short duration of cold storage, 4 and 8 weeks respectively, gave high germination rates, 38% and 33%, respectively. Treatments 3 and 4 with 12 and 16 weeks cold storage, respectively gave low germination rates of 14% and 18%, respectively. Hence, extended cold conditioning beyond 8 weeks is not desirable when embryos are held on the gelled 2M21 medium.

Several of the liquid conditioning treatments that used wet filter papers had both relatively high germination and conversion (Table 16). For example, Treatments 7, 8, 9 and 10 all had germination and conversion rates similar or higher than the control. The percentage of embryos that were plantable (% germination×% plantable germinants) was therefore highest for these treatments.

These results can be summarized as follows:

Moisture content of embryos after conditioning using the gelled medium substrate averaged 77% (Table 17).

Embryos from the gelled method had germination rates of 38% and of these germinants 34% were plantable. Thus, 12% of the embryos (38%×34%) were plantable (Table 16).

Extending the gelled conditioning method to as long as 19 weeks had little affect on embryo moisture content (Table 17) but reduced the number of embryos that were plantable (Table 16).

Moisture content of embryos after conditioning using the liquid cold conditioning method on filter paper moistened with 2 ml liquid medium ranged from 82% to 87% (Table 17), only slightly higher than the standard, gelled-stored embryos. This results verifies that moisture is not lost from the embryos during this version of the liquid-based cold conditioning treatment, but rather than the embryos may slightly increase their moisture content.

Water loss during the liquid cold conditioning method with 2 ml liquid medium was near the 75% targeted loss when the storage duration was 12 and 16 weeks, but lower when the storage duration was 8 weeks (Table 17).

Water loss during the liquid cold conditioning method with 1 ml liquid medium was near the 75% target when the storage duration was 8 weeks. When the storage duration was longer, 12 or 16 weeks the water loss exceeded the amount of liquid added to the filter papers (Table 17).

This suggests that using 1 ml rather than 2 ml liquid medium may be better when the duration of the cold conditioning treatment is to be 8 weeks. Conversely, using 2 ml may be best when the duration of cold conditioning is to be in the 12 to 16 week duration.

The highest % germination and % plantables was obtained in several cold conditioning treatments (treatment 7, 8 and 9). The percentage of plantable embryos ranged from 16 to 22% (Table 16), slightly higher to nearly double the 12% plantables in the standard (treatment 1) method.

Moisture contents of the embryos in the longer duration cold treatments (trts 9 and 10) reached 44% and 21% (Table 17) and still had high levels of germination and conversion (Table 16). Thus using the liquid-based cold conditioning method with 1 ml liquid for extended duration (12 or 16 weeks) results in moisture loss from the embryos beyond the targeted amount.

These results support the uses of the liquid-based cold conditioning method for a duration of 8 to 16 weeks by placing mass harvested embryos on rafts on top of filter papers moistened with 2M21 medium. The volume of liquid medium added to the filter paper varies (1 or 2 ml) depending on the desired duration. The results here suggest that 2 ml is best for longer (i.e., 16 week) duration of conditioning, whereas 1 ml is best for shorter (i.e., 8 week) durations.

This method results in germination and conversion similar to or slightly better than the standard, gelled-stored method of cold conditioning followed by high relative humidity. In addition, this liquid-based cold conditioning method does not require transfer of embryos to cumbersome high relative humidity boxes. That is, the new method is a single phase conditioning treatment that occurs in one container.

These results are important for large-scale production for several reasons. First, it would be advantageous to avoid the high relative humidity box method, which is cumbersome to handle and time consuming, and therefore costly. Secondly, the liquid-based cold conditioning method provides an alternative that may be more cost effective that does not require use of high relative humidity boxes. The conditioning takes place in one container with no transfer until embryos are finally removed for germination.

Example 13

Optimization of Liquid Maintenance Media for Rapid Bulk-Up of Embryogenic Tissues of Loblolly Pine This experiment was designed to test the effect of different liquid media for rapid tissue bulk up with the goal of identifying a liquid maintenance medium for producing a large volume of embryogenic tissue cost-effectively for embryo production.

This is a long-term experiment where five cell lines were maintained as liquid cultures for up to 24 weeks. At the beginning of this experiment, these post-cryo tissues were already six month old. Embryo production capacity of these cultures was tested at four-week intervals. Embryo conversion data from first plating of two cell lines (J1 and J2) where we had enough embryos from all four media treatments listed below.

The composition of the DCR medium can be found in Tables 1 and 2.

1. DCR with total 0.5 g/l casein
2. DCR with total 1.0 g/l casein
3. Mi3 with total 0.5 g/l activated charcoal and total 1.0 g/l casein
4. Mi3 with total 0.5 g/l activated charcoal and total 2.0 g/l casein The liquid-dispersed tissues were placed in flasks containing 20 ml of the respective treatment media. The flasks were sealed and placed in the dark growth room. After one week, the suspension cultures were scored for their SCV and an additional 10 ml of the respective treatment media was added to the flasks. After one more week of culture incubation, the cultures were scored again for their SCV. SCV data was recorded at weekly intervals at time of subculture. At this point, (that is two weeks after initiation of liquid culture), two flasks were maintained from each treatment combination (a total of 40 flasks). All cultures with SCV's at 60 or above were plated to development at 4 weeks of liquid culture age. All SCV's were adjusted to 60 at the time of plating. One ml of SCV suspension was plated to embryo development medium (MSG embryo production medium, see Table 1) and four plates were prepared from each flask (4 replications). The plates were sealed with saran wrap and incubated in the dark growth room. Standard methods were used for embryo development process and harvestable somatic embryos were counted. At the time of liquid culture initiation, tissue maintained from each cell line on gelled Mi3 medium was also plated using embryo development standard medium to obtain base line somatic embryo production data.

Weekly SCV data, amount of new medium added in each subculture and harvestable embryo count data were recorded. Tissue bulk up rate (in fold) for each flask at each subculture was calculated by dividing 30 (total volume of suspension in ml in each flask) with the value (volume in ml) retained in each flask before adding fresh medium. Total potential volume of SCV (in ml) available for plating at 4 weeks of liquid culture age for each flask=30 ml×tissue bulk up rate (in fold) at 3rd subculture×tissue bulk up rate (in fold) at 4th subculture×dilution ratio for 60 SCV. Total number of potential harvestable somatic embryos for each flask=total potential volume (in ml) of tissue at 60 SCV×number of somatic embryos per ml of SCV. Data was analyzed using PROCGLM procedure of a commercially-available software package SAS. SAS is statistical software used for data analysis (SAS Institute Inc., Cary, N.C. USA).

Settled cell volumes (SCV) were measured from each cell line every week for each treatment media. SCV is a well known estimation of cell growth. Highly significant variations were observed among cell lines ($p<0.0001$) and among treatments ($p<0.0001$) for SCV. Similarly, cell line×media treatment interaction was also highly significant ($p<0.0001$).

To make the vast amount of data easily understandable, the ratios of treatments #2, #3 and #4 relative to the treatment #1 were calculated both for tissue production and embryo production. First, pooled mean over five cell lines×6 data points was calculated for each treatment for tissue production. The values are 19.3, 33, 67 and 90 for the treatments 1, 2, 3 and 4 respectively. The ratios of treatment #2 (33/19.3)=1.7, treatment #3 (67/19.3)=3.5 and treatment #4 (90/19.3)=4.7 were calculated. The ratios of treatment #3, treatment #4 for embryo production (Table 26) were also calculated using the same method. Potential tissue production value for each treatment was calculated by multiplying the tissue production value with the embryo production value. For example, for treatment #4 (4.7×5.4)=25.

The average for five cell lines pooled by treatment is shown in Table 25. Table 25 shows faster growth (more rapid bulk-up) in Mi3 liquid media (both casein treatments) during the entire period when compared to the DCR control. Increased casein in DCR (1 g/l casein) also shows slight increased growth up to four months in culture over the control but significantly lower than the Mi3 treatments. However, in the $5^{th}$ and $6^{th}$ months treatment #2 (DCR with 1 g/l casein) produced significantly larger volume of tissue and was approaching close to Mi3 treatments.

Since cell line by media treatment interaction was highly significant, data from each line was analyzed separately for each treatment. Comparison of tissue production (increase in fold) at different time points in liquid culture is shown in Table 19. Values in each box represent multiplication of tissue bulk up rates of four weeks. For example, the value for tissue of cell line J5 maintained in treatment #4 medium at week-12 is 78. This value was calculated by multiplying tissue bulk up rates at week 9, 10, 11 and 12=2.8×2.9×3.0×3.2, respectively. According to our current method after subculture, SCV of the diluted suspension should be approximately 40.

Typically, a suspension is not subcultured if it does not reach SCV 60 after 7 days that means a minimum of 1.5-fold increase per week. Therefore, in four weeks a minimum expected increase in fold should be 1.5×1.5×1.5×1.5=5 for a cell line to be considered growing in liquid culture. Based on this criterion, only two cell lines (J1 and J2) could be maintained in all four treatment media for the whole 24 week. The starting material at week-0 was one gram of tissue, which is equivalent to 5 ml of 60% SCV suspension. Value in the week-4 column was calculated based on how much 60% SCV suspension was available in ml divided by 5.

The effect of medium treatments on tissue bulk up potential from five cell lines at different time points in culture after liquid culture initiation is shown in Table 19. Line-to-line variation for tissue volume was observed.

Treatment #1 failed to sustain tissue growth in three of the five cell lines. On the other hand, treatment #4 (improved medium) sustained tissue growth in all the five cell lines. When the performances of Treatment #2 (DCR-1 casein) and Treatment #3 (Mi3-1 casein) media were compared, the Mi3-1 casein medium was similar for the cell line J3 and significantly superior for the other four cell lines. On the other hand, Treatment #4 (Mi3-2 casein) medium was significantly superior to DCR media for all cell lines. Treatment #4 was not only best in tissue bulk up capacity, its performance was also consistent with an average of 98-fold increase at four week interval.

Embryo production data of the five cell lines was compared from tissues bulked up in four liquid media at four-week intervals. Highly significant variations were observed among cell lines ($p<0.0001$) and among treatments ($p<0.0001$) for embryo production. Similarly, cell line×media treatment interaction was also highly significant ($p<0.0001$). The results are shown in Table 20.

Both flasks were maintained from each line by treatment combinations up to fourth plating and tissues from all 40 sources (5 lines×4 treatments×2 flasks) were plated for embryo development. After fourth plating, the line by treatment combination that failed to grow was discarded. The embryo production data in Table 20 clearly shows the superiority of treatment #4 (Mi3 medium with 2 casein) over treatment #1 (control) medium. Although significant flask to flask variation was not observed in our first plating, that was evident in the subsequent plating (*=significant and **=highly significant difference). Embryo production capacity declined with culture age for majority of the cell lines. It may be noted here that these cell lines were already six months old when liquid culture was initiated.

Table 26 shows the effect of four treatment on tissue production, embryo production and potential embryo production of five cell lines (pooled). Data represents increase in fold compared to the control (Liquid DCR with 0.5 g/l casein) which is 1.

Embryos from first plating of two cell lines (J1 and J2) where there was sufficient embryos from all four media treatments were hand harvested, conditioned, germinated and converted using the standard method. The results are shown in Table 21. Although a line-by-treatment interaction was evident, pooled conversion data suggest that the quality of embryos produced by the four media treatments was comparable.

Example 14

Comparison of DCR and MI3/0.5 Casein Media

Immature seed explants from 17 loblolly pine families were plated onto standard WV5 initiation media. See Tables 1 and 2. Newly initiated embryogenic tissues extruded from the immature seed explants (cell lines) were transferred to Medium 1 (DCR), or Medium 2 (Mi3 with 0.5 g/l casein), two alternative maintenance media treatments. The sucrose concentration was 30 g/l in both media. Tissue was transferred to fresh media every 2 weeks.

Data were collected on the number of newly initiated cell lines that successfully grew to a mass of 1 gram. See Table 22.

Approximately 1320 newly initiated cell lines from 17 loblolly pine families were transferred to the two alternative media. 51% of those cell lines grew successfully to a mass of 1 gram on the Mi3 medium, whereas 40% of the cell lines grew successfully to a mass of 1 gram on the DCR medium.

Example 15

Comparison of MI3 Maintenance Media with Two Levels of Casein

Immature seed explants from 4 loblolly pine families were plated onto one of two WV5 initiation media. See Tables 1 and 2. One WV5 medium has the "standard" amount of casein, e.g., 0.5 g/l, while the other plate had 2.0 g/l of casein.

The experiment was designed so that the embryos on the 0.5 g/l casein/WV5 media were subsequently transferred to a 0.5 g/l casein/Mi3 media as described below. Similarly, the embryos on the 2.0 g/l casein/WV5 media were subsequently transferred to a 2.0 g/l casein/Mi3 media as also described below.

Newly initiated embryogenic tissues extruded from the immature seed explants (cell lines) were transferred to Medium 2 (Mi3 with a total of 0.5 g/l casein), or Medium 3 (Mi3 with a total of 2 g/l casein) as two alternative maintenance media treatments. The sucrose concentration was 15 g/l in both media. Tissue was transferred to fresh media every 2 weeks.

Data were collected on the number of newly initiated cell lines that successfully grew to a mass of 3 gram. See Table 23.

The use of the maintenance medium with higher casein hydrolysate improved the percentage of newly initiated cell lines that successfully grew to a mass of 3 grams. Success was 40% when cell lines were grown on medium with 0.5 g/l casein, and 48% when grown on medium with 2 g/l casein.

Example 16

Effect of Embryo Development Medium on Embryo Production

Twenty-six embryogenic cell lines were grown on maintenance medium 3 (Mi-3 with 2 g/l casein) and plated to two embryo development media, i.e., on to MSG base medium. This medium is MSG-based with 2 g/l maltose and 21 mg/l ABA. One medium had 70 g/l PEG and one had 130 g/l PEG (PEG=polyethylene glycol). Tissue with development embryos was transferred to fresh medium after 6 weeks and embryos harvested after an additional 3 weeks.

Cell lines were scored for embryo production. Table 24 scores the lines for embryo production. Yes=at least 10 embryos per gram of tissue; No=less than 10 embryos per gram of tissue.

Seven of the 26 lines plated showed differential embryo production between the two development media tested. Note that several lines (for example, cell lines 6, 10, and 17) responded much better on 13% polyethylene glycol medium, where as other lines (e.g., cell lines 2, 24 and 25) responded much better on 7% polyethylene glycol medium.

Additional tests on other cell lines revealed that germination of certain genotypes also is influenced by PEG concentration. Therefore, one may be able to optimize both embryo production and germination in a genotype-specific manner.

Example 17

Effect of Casein Level on Recovery and Growth of Conifer Embryogenic Cultures Retrieved from Cryostorage It is known by those skilled in conifer somatic embryogenesis that cultures generally lose regeneration capacity with increase time in culture. Therefore it is important for successful application of SE to clonal propagation of conifers to be able to retrieve and rapidly multiply or bulk up cultures from cryogenic storage and to be able to do so with many different genotypes to increase the likelihood of capturing select genotypes.

This example tested the effect of an improved tissue bulk up medium (Mi3 with high casein) on both the growth rate and the recovery frequency of loblolly pine embryogenic cultures from cryostorage.

Soon after culture initiation each 10 family H and 12 family I loblolly pine embryogenic cell lines were each divided equally to the 0.5 and 2.0 g/l casein treatments in Mi3 pre-cryo maintenance medium. The lines were cryopreserved according to standard methods, retrieved from cryogenic storage and placed onto Mi3 medium (Tables 1 and 2) containing either 0.5 g/l (standard level) or 2.0 g/l (high) level of casein hydrolysate—the same level each sample had been on prior to and during cryostorage. Thus, each cell line was tested on both low and high casein. This design helps ensure that observed differences in growth or recovery are more likely due to treatment effects rather than genotype effects.

At 4 weeks post-cryo recovery all tissue was weighed. The 6-week culture weight is a potential weight based on how much a sub-sample increased in weight multiplied by the 4-week weight.

There were significant lines by casein level interactions on both the actual 4-week tissue growth (p<0.0001 for family H and I lines) and the potential 6-week tissue growth (p<0.0001 for family H and p=0.01 for family I lines). his result shows that some lines benefit more from higher casein than other lines in terms of increased tissue growth.

Overall the high casein more than doubled the amount of tissue available at 4 weeks (Table 27). In several lines there was little or no growth on the low casein, but significant growth on the high casein treatment.

In addition to the positive effect increased casein had on growth, it increased the frequency of cell line recovery in both families (Table 28). Whereas, only 6 of 10 cell lines were retrieved from family H on the 0.5 g/l (standard) level of casein, 9 of the 10 lines were retrieved on the higher level on casein. All 12 family I cell lines were retrieved on high casein, whereas only 7 of the 12 were retrieved on low casein.

This is an important result for the successful implementation of clonal test strategies. It shows that more lines can successfully be recovered from cryostorage using the Mi3 medium with high casein. Although there was a line by treatment interaction, overall the lines can be bulked up more rapidly on high casein. This result significantly increases the likelihood that elite lines can be successfully be recovered from cryostorage and bulked up for mass production. Furthermore, the rapid bulk up rate helps ensure that the resulting cultures will have retained their embryogenic capacity for large-scale production.

In conclusion, using high casein in the culture medium increased the number of lines that can be recovered from cryogenic storage and improved tissue growth.

Example 18

Effect of Brassinolide in Post Cryostorage Recovery Medium on Tissue Growth and Subsequent Embryo Production of Loblolly Pine Embryogenic Cell Lines This experiment addresses whether brassinolide in the post-cryogenic storage bulk up medium has a positive effect on tissue recovery and growth enabling faster tissue multiplication and bulk up; and whether there is a cell-line-by-treatment (with or without brassinolide) interaction that can be exploited to enable genotype screening to optimize the best combination for each cell line in terms of both tissue growth and subsequent somatic embryo production.

Two post-cryostrorage recovery (bulk up) media treatments were tested:

Treatment #1: Mi3 medium (Tables 1 and 2) with high (2.0 g/liter) casein (the improved medium)

Treatment #2: The same high casein Mi3 with addition of 0.1 µM Brassinolide

Five J cell lines and five K lines were tested. For each cell line, 4 vials (2 post-cryo recovery media×2 replications) were retrieved from cryostorage. Recovered tissue from each vial was transferred to their respective fresh medium at 2 week intervals using a raft transfer method. Weight data was recorded for tissue derived from each vial at the $6^{th}$ week after cryo-retrieval. At the $6^{th}$ week, tissues from both reps of each treatment were pooled and maintained on their respective maintenance medium using a tissue dispersion method: 200 mg per sample in 1 ml liquid Mi3 medium dispersed by agitation and poured onto each culture plate. A total of 800 mg of tissue from each cell line×post-cryo media combination were plated on embryo development medium (4 reps of 200 mg/plate) to test embryo production capacity. Total tissue weight at each subculture was recorded to calculate the potential of each treatment for tissue bulk up and embryo production. Harvestable somatic embryos from each plate were recorded at 9 weeks of incubation on MSG embryo development medium (Tables 1 and 2). Embryo production data was analyzed separately for the J and K cell lines using PROCGLM procedure of SAS. Embryo production potential for each treatment was calculated by multiplying embryo production data by the total potential tissue produced in each cell line and treatment.

There were considerable differences in tissue production among cell lines of each source (J and K). For all 10 cell lines, the improved Mi3 medium with addition of brassinolide (treatment 2) produced highest amount of tissue. For slow-recovering cell lines (K10 and K11, and J4), the addition of brassinolide was very effective (a two to three-fold increase in growth).

The effect of brassinolide in the improved Mi3 bulk up medium on subsequent embryo production was tested. Analysis of variance showed highly significant cell line× media treatment interactions (p=<0.0001). Since cell line× media treatment interaction was highly significant, data from each line was analyzed separately for each treatment. The results are shown in Tables 29 and 30.

Overall embryo production potentials of tissues recovered and multiplied on improved Mi3 with brassinolide medium was significantly higher (>35% for both J and K lines compared to the control).

The results clearly show that addition of brassinolide is beneficial for post-cryo tissue growth. The impact of brassinolide on embryo production is highly line dependent. Therefore, a battery approach to screening lines as to their response on Mi3 with or without brassinolide is an effective way to optimize large-scale embryo production.

In summary, the improved Mi3 medium containing brassinolide produced the highest amount of tissue: 127% for J lines and 191% for K lines compared to the improved medium without brassinolide.

Highly significant cell line×media treatment (with or without brassinolide) interactions (p=<0.0001) were observed for embryo production capacity of 6 week-old tissues.

This medium-type by line interaction enables one to screen for and optimize embryo production for particular cell lines for large-scale production.

Embryo production potential of tissues recovered and multiplied on improved Mi3 with brassinolide medium was significantly higher—149% for J cell lines and 136% for the K cell lines—compared to the improved Mi3 without bassinolide.

Example 19

Improving Genotype Capture Among Several Different Genetic Families of Loblolly Pine by Exploiting the Family by Media Treatment Interaction Immature seed explants were cultured from each of seven genetically different families (A, B, C, D, E, F and G) of loblolly pine. The explants were cultured on four different culture media—treatments 1, 2, 3 and 4 as shown in Table 31. The somatic embryogenic tissues from responsive explants were transferred to maintenance media as shown in Table 31 at 8 weeks. After 4 weeks on maintenance medium (tissue transferred to new maintenance medium at week 2, the number of cultures that reached at least 1 gram was determined. Briefly, the four treatments were: the control treatment (no. 1) had WV5 initiation medium with 30 g/l maltose and 0.5 g/l casein, and Mi3 maintenance medium with 30 g/l sucrose and 0.5 g/l casein. Thus, the control treatment had a typical (i.e., low) casein levels in both the initiation and maintenance medium. Treatment 2 differed from the control by having a high level (2 g/l) of casein in both the initiation and maintenance medium. Treatment 3 differed from the control by having reduced level of maltose (15 g/l) in the initiation medium. Treatment 4 differed from the control by having both high casein (2.0 g/l) and low maltose (15 g/l) in the initiation medium, as well as high (2.0 g/l) casein in the maintenance medium.

The statistical (logit) analysis of the data showed that there was a highly significant family by treatment interaction (p=0.02) for the percentage of seed explants that established vigorously growing cultures at 12 weeks. Thus SE culture establishment frequency for most families (5 of 7) varied by treatment. Two of the five families (D and E) had the highest establishment frequency on treatment 2, which had high casein in both the initiation and maintenance medium. Three of the five families (C, F and G) had the highest establishment frequency in treatment 4 that had high casein and low maltose in the initiation medium and high casein in the maintenance medium.

These results show that screening a number of families in a battery of culture initiation/maintenance media results in being able to capture more SE cultures successfully. This approach enables one to identify a particular medium type that is best suited to a particular genetic family. After an initial screening to determine the most responsive medium type, one can culture additional explants on the "preferred" medium type to attain the highest initiation frequencies for each individual family.

The power of this approach becomes apparent by noting the following differences in genotype capture frequency based on being able to choose the optimum medium for a particular family. For example, based on the results in Table 31, it is necessary to culture 10,000 explants of family C on WV5 (control media, trt #1) to capture 100 cell lines. Whereas, it is necessary to culture only 1000 explants of the same family C to get 100 cell lines using the improved WV5 initiation medium (high casein and low maltose) in combination with the improved Mi3 maintenance medium (high casein).

Similarly, whereas, 5000 explants of family E are needed to culture on WV5 control medium and Mi3 control maintenance medium to get 100 cell lines, only 1400 explants of family E need to be cultured on WV5 with high casein followed by Mi3 with high casein to get 100 cell lines The battery approach, therefore, enables much more efficient capture of genotypes for clonal testing and increases the likelihood of being able to capture sufficient genotypes needed to identify those genotypes with significant genetic gain potential desired for large scale deployment.

Example 20

Improving Embryo Production Efficiency by Exploiting the Genotype by Embryo Development Interaction Seven loblolly pine cell lines were tested on two PEG levels (7 and 13%) and two PEG types (Fluka: molecular weight 4000 and Acros: molecular weight 8000), for a total of 4 somatic embryo development treatments. Multiple embryo development plates were tested on each treatment and the data tracked by plate to enable an average number of plants per development plate to be determined. Data collected included: (1) average number of harvestable embryos produced per embryo development plate, (2) frequency that harvested embryos germinated, and (3) the average number of established plants produced per embryo development plate. See Table 32.

There were significant line by treatment interactions for embryo germination and plant establishment. Some cell lines benefited from increased PEG, while others had a significant decrease in the number of plants produced on higher PEG. Thus, a genotype screening approach for optimizing the embryo development medium is an effective way to ensure that during large-scale production with specific genotypes that the optimum embryo development medium is utilized.

For example, based on the results, although cell line A1 produced more embryos on high PEG the germination and conversion was suppressed on high PEG. Since germination and conversion are costly steps, it would be advantageous with this particular cell line to use 7% PEG, preferably the 4000 molecular weight Fluka type. Cell line C1 responded differently, having the best embryo production, germination and conversion (plant establishment on 13% PEG 4000 Fluka type. Therefore, the genotype screening approach enables one to optimize the embryo production for each genotype.

Example 21

A Combinatorial Approach to Optimizing the Somatic Embryogenesis Process for Use in Large-Scale Commercial Production First, in the initiation and maintenance steps, the media combination used in these two steps is optimized at the family level. This approach was outlined in Example 19. This enables the most efficient capture of genotypes from a particular family to be placed in cryogenic storage for subsequent use in the multi-step process.

Second, in the recovery of cell lines from cryostorage the medium components are optimized according both tissue growth and subsequent embryo production. This approach was outlined in examples 17 and 18.

Third, in the embryo development step, multiple embryo development media are tested, to determine the optimum medium for a particular cell line. This approach is outlined in examples 20 and 16.

Therefore, applying a battery of media at several sequential steps, results in a combinatorial approach to increase the likelihood of maximizing the number of commercial candidates for scale-up, and also increasing efficiency and reducing cost for implementing the somatic embryogenesis process. This medium-type by line or family interaction enables one to screen for and optimize several parameters, including the following: genotype capture, tissue recovery from cryogenic storage, large-scale tissue bulk up, embryo production, germination and plant establishment (conversion) efficiency for particular cell lines for large-scale production.

Example 22

Alternative Embryo Conditioning Methodology

Somatic embryos from several different loblolly pine cell lines were tested for germination after exposure to either a standard method described below and in U.S. Pat. No. 5,413,930, which is incorporated herein by reference. The new and improved method described herein is much simpler, cost less, is less time consuming, and results in similar or better germination and plant conversion. Most importantly, this new improved conditioning method is more amenable to scale-up for conditioning large numbers of embryos for large-scale commercial production. Whereas, the standard method as taught in U.S. Pat. No. 5,413,930, although effective for small scale production, is not amenable to large-scale commercial production.

The standard (control in Tables 33 and 34) small scale conditioning used vessels containing 50 ml of sterile water over which was placed a support-grid to keep the embryos from direct contact with water. Rafts containing harvested embryos were blotted with sterile filter paper and placed on the support-grid in the vessel. This standard conditioning method is one of the most cumbersome steps of the SE process, and does not easily lend itself to scale-up for larger production runs. The experiment shows that good embryo germination and conversion can be achieved by simplifying the conditioning process, and avoiding the cumbersome high relative humidity (HRH) step where embryos are held in sealed vessel over water. The standard method requires large amounts of handling, including: preparing the vessels, filling them with water, blotting embryos, and storage of the bulky HRH vessels. The alternate 'no HRH' conditioning method requires only one sterile raft and vessel per raft of embryos. It is possible, if desired, to place more than one sterile raft with embryos per vessel. Embryos on the raft or rafts were brought from cold storage (7° C. in this example) and placed onto a dry filter paper in a sterile vessel. The vessels were sealed with Nescofilm™ and then incubated in the dark at approximately room temperature (24° C. in this example). After three weeks, embryos were removed and placed on modMS1 germination medium. The embryos were then singulated onto the surface of the medium and germination begins.

Germination was essentially the same between the two conditioning methods (Tables 33 and 34). In both tests the germination was similar between method 1—the control or standard method, and method 2—the new improved conditioning method. But, the new conditioning method is much simpler, more cost effective and therefore more useful for large-scale commercial production. Both experiments conducted with different cell lines showed the same result. Namely, that the new conditioning method is a significant improvement over prior art methods because of its simplicity and ease of use and still results in equivalent or better germination of embryos.

Example 23

Semi Automatic Embryo Mass Harvester Machine

Figure 11:
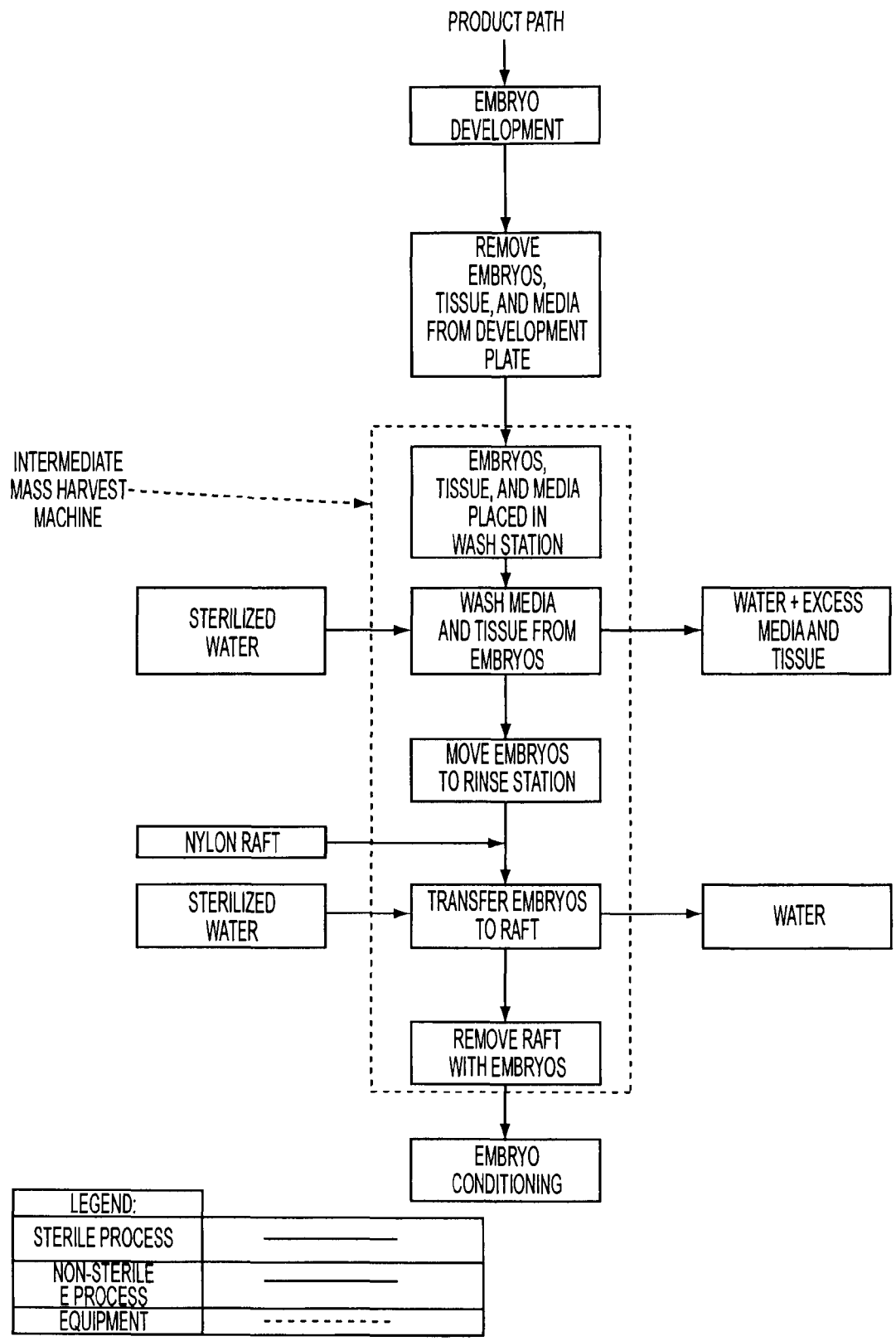
FIG. 11 is a process flow diagram of the intermediate Mass Harvesting machine.

This example relates a batch mode embodiment of a semi automated embryo mass harvesting machine. The functionality of the machine can be converted to a fully automated continuous machine, which can be integrated into a large scale automated production line. The semi automated batch mode embryo mass harvester machine had three basic functional modules: 1) wash units, 2), holding units, and 3) rinse units. Both wash units and rinse units had vacuum assistance for waste water and tissue removal. The machine was automatically controlled by a small Programmable Logic Controller (PLC) (e.g. Direct Logic, model number DL-05) with an operator interface for operator inputs, operational parameters, error messages, and production reports. A PLC with more digital inputs and outputs or a PC-based computer would be required for a fully automated system. The entire machine was located in a sterile environment e.g. a laminar flow hood or HEPA-filtered chamber. The machine also had the additional functionality of Cleaning in Place (CIP) for good Quality Control (QC) by the simple addition of plumbing, a pump and an automatically controlled valve to sterilize the machine during the non production hours without dismantling the machine. This ensures maximum uptime while maintaining sterile conditions. Embryos were harvested as outlined in FIG. 11 (process flow diagram). The following steps describe the operation of the machine.

Step 1

The operator loaded embryos and tissue into the 3 holding units (approx. 500 embryos per holding unit) by tilting the holding unit, such as by 45 degrees, towards the operator for ease of loading.

Step 2

The operator aligned the holding units vertically over the wash units and initiated the washing process with a foot switch. The controller verified that the assemblies were in the correct position and orientation by positional sensors. The controller then activated two pneumatic cylinders to lower the holding units and spray mechanisms into the wash position. In the lowered position, additional sensors verified that the assemblies were registered in the correct positions before the wash cycle began. The preprogrammed wash cycle was then executed. Media, waste water and extraneous plant tissue were pulled away using vacuum by automatically opening an electronically controlled valve.

Step 3

The controller automatically raises the spray mechanisms and holding units using the pneumatic cylinders. The operator was prompted to traverse both assemblies horizontally towards the front of the machine to the rinse unit. If the tissue was not completely washed from the embryos, the operator could intervene and initiate another wash cycle using the foot switch.

Step 4

If proceeding to the rinse cycle, the operator rotated the holding units 180 deg resulting with the tissue being located on the bottom side. Once the heads were aligned with the rinse station, the operator initiated the rinse cycle with the foot switch.

Step 5

The controller and proximity sensors ensure proper alignment before proceeding. The controller then activated two pneumatic cylinders to lower the holding units and spray mechanisms into the rinse position. The preprogrammed rinse cycle was then executed. The rinsed embryos were collected onto rafts located in the rinse units and the rinse water was pulled via vacuum by automatically opening a second electronically controlled valve.

Step 6

At the end of the rinse the controller raised the holding units so that the operator could tilt and slide the holding units away from the rinse units. The rafts with the harvested embryos were then removed for the next stage of the production process.

A more detailed description of a presently preferred embodiment of the invention is provided below and illustrated in the drawings. An effort has been made to use the same or like reference numbers throughout the drawings to refer to the same or like parts.

Figure 2:
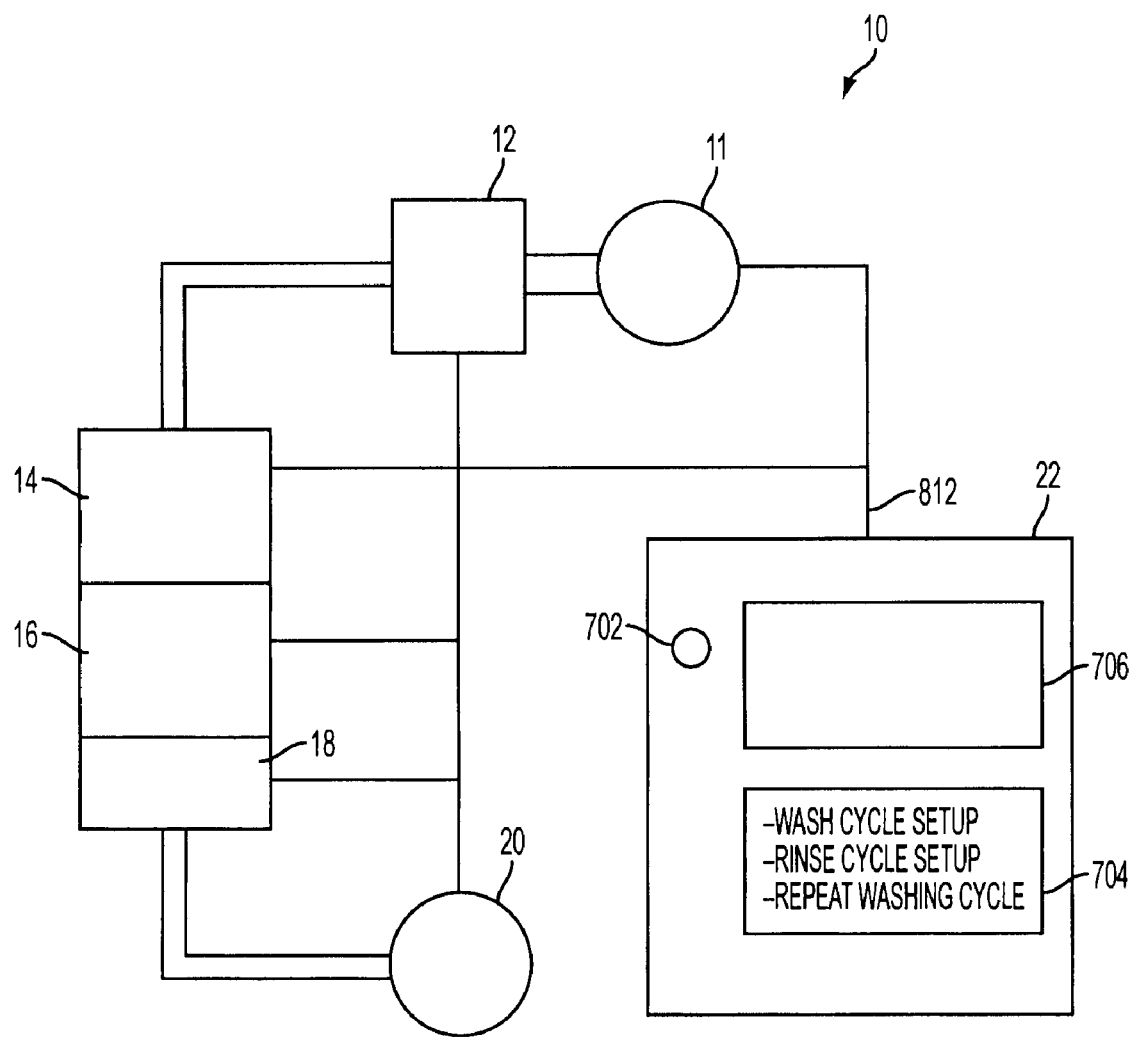
FIG. 2 is a schematic drawing of an embodiment of a plant embryo cleaning apparatus according to the present invention.

Referring to FIG. 2, a schematic drawing is shown of an embodiment of a plant embryo cleaning apparatus 10 according to the present invention. The plant embryo cleaning apparatus 10 can be used for preparing multiple plant embryos for plant production. As shown in FIG. 2, the plant embryo cleaning apparatus 10 preferably includes a cleaning fluid source 11, a fluid-conditioning system 12, a spray mechanism 14, a cleaning station 16, an outlet mechanism 18, a negative pressure source 20, and a controller 22.

The fluid source 11 can be selected from a variety of sources known in the art, because the plant embryo cleaning apparatus 10 can use any type of suitable cleaning fluid for washing and rinsing the plant embryos. Thus, the fluid source 11 could be, for example, a faucet providing mere cold tap water or one or more storage tanks providing water.

Figure 3:
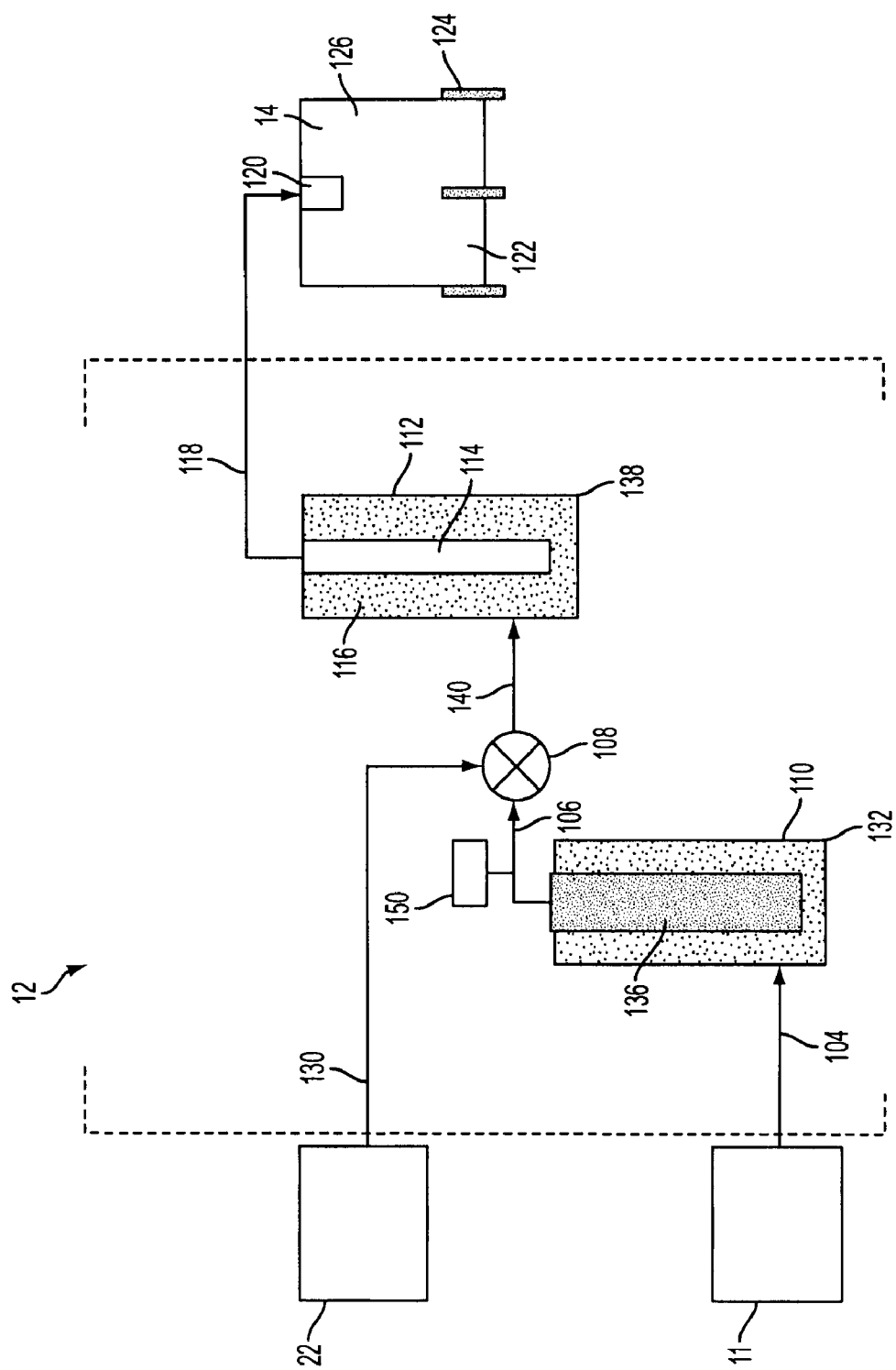
FIG. 3 is a schematic drawing of a cleaning fluid source, a fluid-conditioning system, and a spray mechanism of the plant embryo cleaning apparatus of FIG. 2.

The fluid-conditioning system 12, as shown in FIG. 3, can be positioned between the fluid source 11 and the spray mechanism 14. The cleaning fluid preferably flows out of the fluid source 11, through a fluid line 104 to the fluid-conditioning system 12, and then through a fluid line 118 to the spray mechanism 14. Fluid line 104 can be any suitable piping or tubing, such as one inch diameter poly vinyl chloride (PVC) pipe. The fluid line 118 can be any suitable tubing or piping, such as ⅜" diameter Tygon tubing.

The fluid-conditioning system 12 can remove contaminants from the cleaning fluid and/or sterilize the cleaning fluid before it reaches the spray mechanism 14. The fluid-conditioning system 12 may include a filter unit 110, an electronically controlled valve 108, and/or an ultraviolet sterilizer 112.

The filter unit 110 of the fluid-conditioning system 12 can be any suitable filter unit that removes contaminants, such a membrane filter. In this embodiment, the filter may include a filter housing 132 (such as a Cole Parmer Model Number 01508-35) and a filter cartridge 136 (such as a Cole Parmer Model Number 01509-05). The filter cartridge can have any suitable pore size, for example 1 micron. The cleaning fluid flows into the filter housing 132 from the fluid line 104 and flows through the filter cartridge 136 and flows out into the fluid line 106. Fluid line 106 can be formed, for example, of the same material used for fluid line 104. The fluid line 106 can include a pressure regulator 150 that is used to control the pressure of the input fluid going to the spray mechanism 14 (which will be described later).

The electronically controlled valve 108 can be configured to control flow between the filter unit 110 and the UV sterilizer 112. It can be any control valve known in the art, such as a simple solenoid valve. The electronically controlled valve 108 is controlled by a control signal 130 from the controller 22 to open if it is desired for fluid to flow from fluid line 106 to fluid line 140 and into the ultraviolet sterilizer 112. The electronically controlled valve 108 can be closed by the controller 22 to prevent such flow. The fluid line 140 can be any suitable tubing or piping, such as one inch diameter PVC piping. The state of the electronically controlled valve 108 will be determined by the stage of the cleaning cycle the system is undergoing at a particular time or upon operator selection if the operator chooses to interrupt the cleaning operation.

The UV sterilizer 112 is a device that uses UV radiation to kill micro-organisms in the cleaning fluid. The sterilizer 112 includes a housing 138, one or more UV light bulbs 114, such as a fluorescent lamp, and a flow channel 116. The light from the UV light bulb 114 illuminates the fluid as it flows through the flow channel 116. An example of a suitable UV sterilizer is a Hydrotech Sterilizer Model Number Pura UV20-1, which emits light at a wavelength of 254 nm. As the fluid leaves the UV sterilizer 112, it enters into the fluid line 118, which leads to the spray mechanism 14.

The spray mechanism 14 or fluid-delivery structure can be configured to adequately dispense cleaning fluid onto the embryos. The spray mechanism 14 may comprise a nozzle 120, a spray housing 122, and at least one alignment mechanism 124.

The nozzle 120 can be selected depending upon the desired flow rate and spray pattern of the cleaning fluid. For example, the velocity or pressure of the fluid should be selected so as to not damage the embryos during the washing or rinsing processes. The velocity of the fluid is dependent upon the line pressure, the negative pressure applied to the cleaning stations (as will be discussed later), and the design of the nozzle. The velocity or pressure of the fluid can be changed for different types of embryos by simply changing the nozzle. An example of a suitable nozzle is one made by AllSpray LLC with a Model Number of FCS 65 Deg. This nozzle has a capacity of 1.40 gpm at 40 psi and a range of 0.76 gpm at 10 psi to 2 gpm at 90 psi.

The selection of the nozzle 120 also can be based on the desired spray pattern of the spray mechanism 14. For example, a conical spray pattern may be desired in which the spray impinging on the embryos has an even distribution. Alternatively, the spray pattern may be in a more annular pattern in which more fluid is directed toward the center of the spray while there is less fluid around the spray's periphery. Preferably, the nozzle 120 is configured to provide a spray pattern in which an outer portion of the fluid stream contacts the interior walls of the spray housing 122 and/or the holding unit 202. This type of spray pattern has the effect of keeping the interior walls of the spray housing 122 and/or holding unit 202 free of cellular debris and embryos while still cleaning the embryos with the fluid that has bounced off the walls and back onto the embryos. One with ordinary skill in the art, once made aware of this disclosure, can determine a suitable nozzle based on the desired spray pattern, the line pressure, and the vacuum pressure (which will be described later).

The spray housing 122 can be used to contain the cleaning fluid exiting the nozzle 120 such that the fluid is directed to the cleaning station 16. The spray housing 122 may be substantially transparent, such as a clear polycarbonate, transparent glass, or other type of transparent material so that an operator can see through the spray housing and monitor or observe the results of the washing operation. If the operator is unsatisfied with the results, the operator may order another washing using an input mechanism in the controller 22. Alternatively, a camera (not shown) can be used to monitor the washing operation through the substantially transparent material and to send a signal to the controller 22 (which will be discussed later), which is processed by the controller to determine if another washing operation is necessary. Although the spray housing 122 in FIG. 3 is cylindrical with a circumferential surface 126, it can be any shape, such as pyramidal, conical, or cubical. As a further alternative, a housing of the holding unit 202, wash unit 208, and/or rinse unit 212 can be substantially transparent to permit monitoring of the washing and/or rinsing.

Figure 4:
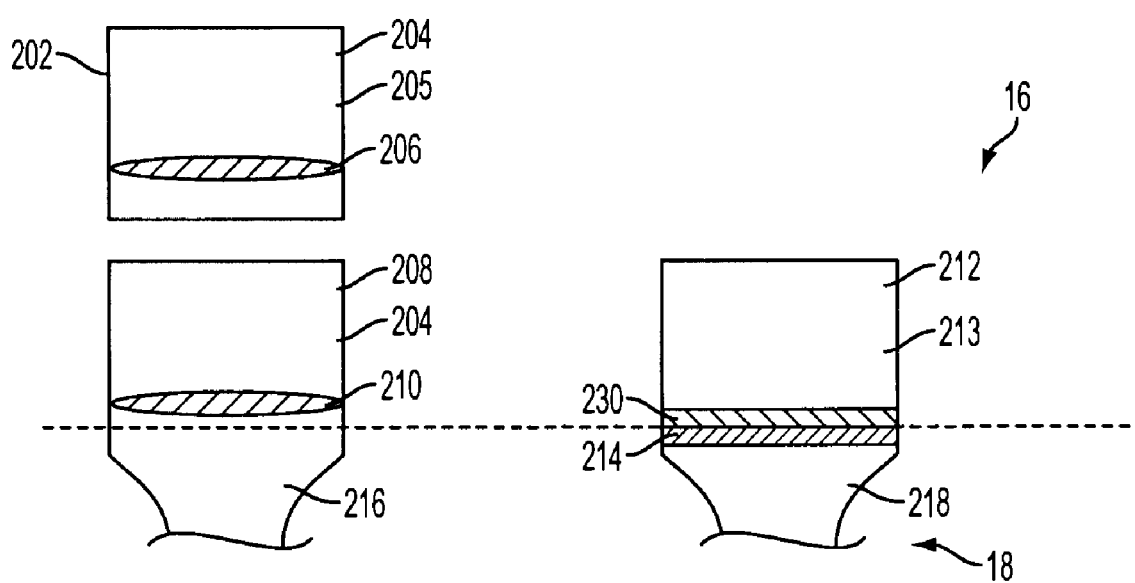
FIG. 4 is a schematic drawing of a cleaning station of the plant embryo cleaning apparatus of FIG. 2.

The alignment mechanism 124 can provide a desired alignment between the spray housing 122 and the cleaning station 16 to achieve an optimal or desired effect of the spray pattern of the nozzle 120. The alignment mechanism 124 can be disposed on the end of the spray housing 122 that is opposite the nozzle 120. The alignment mechanism 124 can be, for example, a series of pins on the circumferential surface 126 of the spray housing 122. The pins can be configured to mate with a holding unit 202 of the cleaning station 16, which is shown in FIG. 4. The circumference of the external surface 204 of the holding unit 202 may simply slide into the inner perimeter formed by the series of pins around the circumferential surface 126 of the spray housing 122 of the spray mechanism 14. Alternatively, the holding unit 202 may have corresponding slots or grooves that accommodate the pins. Instead of pins 124, the alignment mechanism 124 can be, for example, a tubular sleeve (not shown) attached to the circumferential surface 126 of the spray housing 122 and can be configured to mate with the external surface 204 of the holding unit 202. As another alternative, the external surface 204 of the holding unit 202 may fit inside the internal surface of the spray housing 122 or vice versa.

Position sensors (not shown) can be provided to ensure proper alignment between the spray housing 122 and the holding unit 202. The position sensors can be any type of proximity sensor known in the art and they can be placed on the holding unit 202 (or the wash unit and/or rinse unit described below). For example, the proximity sensors can be capacitive, ultrasonic, optical, or electrical-contacting sensors. In the example of an inductive proximity sensor, the sensor generates an electromagnetic field to sense a metal object passing close to its face. When the proximity sensor is within a predetermined distance from a target metal, it sends a signal to the controller 22 indicating a proper alignment. If the sensor does not come within the predetermined distance, no signal will be sent to the controller. In the example of a capacitive proximity sensor, it uses the face or surface of the sensor as one plate of a capacitor and the surface of a conductive or dielectric target object as the other. The capacitance varies inversely with the distance between the capacitor plates in this arrangement, and a certain value can be set to trigger target detection, which is sent to the controller to indicate a proper alignment. If there is an improper alignment, one or more of the following actions can be taken: (1) the cleaning operation can be halted, (2) conventional moving mechanisms (not shown) could try to move the holding unit and/or the spray housing until there is proper alignment, or (3) a warning may be generated via an alarm or display at the controller 22 to warn the operator of the misalignment.

Figure 5:
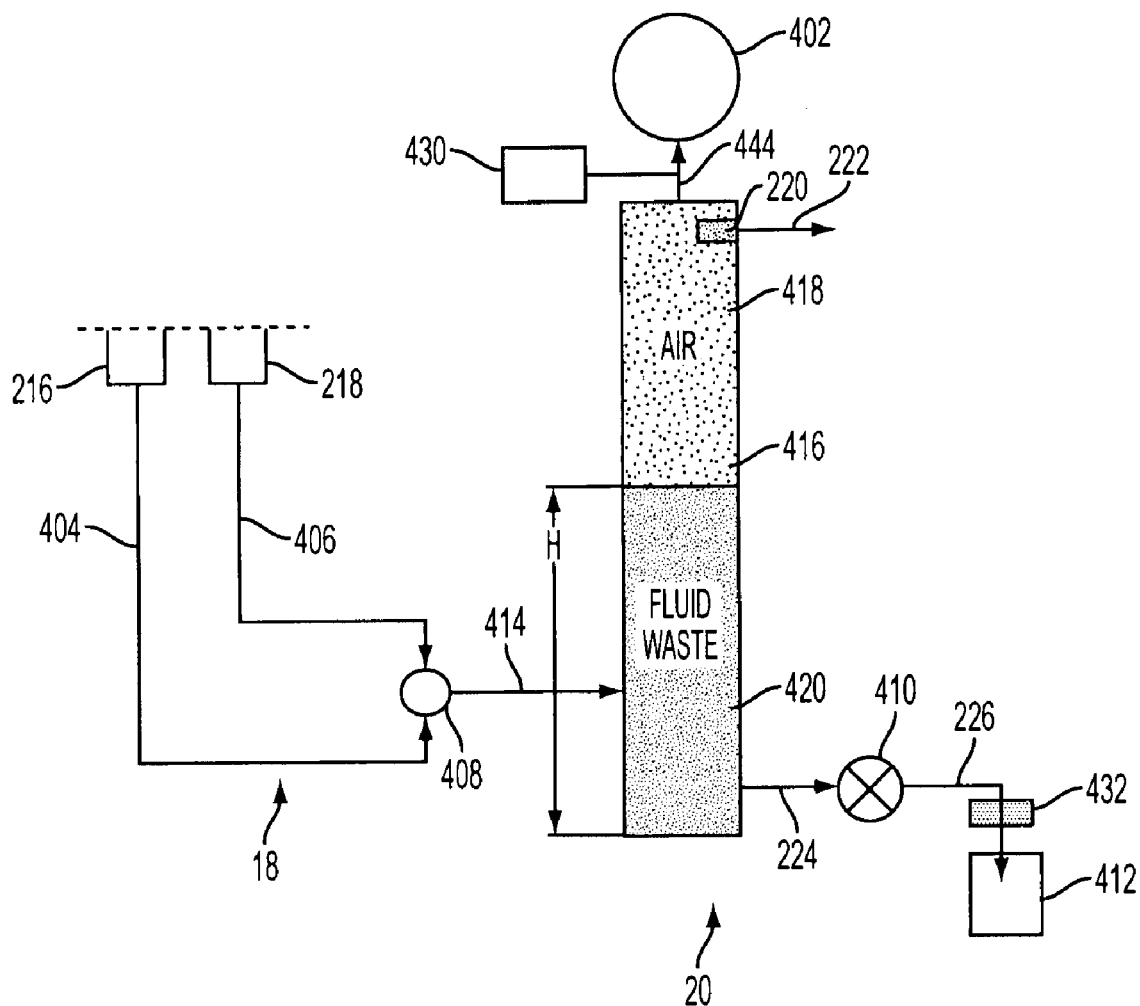
FIG. 5 is a schematic drawing of an outlet mechanism and negative pressure source of the plant embryo cleaning apparatus of FIG. 2.

The cleaning station 16 preferably washes and rinses the embryos. As shown in FIG. 5, the cleaning station 16 may comprise the holding unit 202, a wash unit 208, and/or a rinse unit 212.

The holding unit 202 holds the embryos and transports them between the wash unit 208 and rinse unit 212. The holding unit 202 may comprise a cylindrical member 205 that supports a fixed holding structure 206 for holding the embryos. The cylindrical member 205 can be made from a transparent material, such as glass, polycarbonate or the like to obtain feedback on the washing and/or rinsing operations. For example, the operator may be able to look through the transparent material and see the results of the washing and/or rinsing operations and determine whether additional washing or rinsing operations are necessary. Alternatively, a camera (not shown) can be used to monitor the washing and/or rinsing operations through the transparent material and to send a signal to the controller 22 (which will be discussed later), which is processed by the controller to determine if another washing or rinsing operation is necessary.

The holding structure 206 may be a porous material, such as a mesh material, a sieve, a filter, or the like, configured to hold the embryos. If mesh materials are used, the size and configuration of the pores in the porous material will depend upon the type of embryos being cleaned and the types of cellular debris being removed by the cleaning process, i.e., the species and condition of the embryos can be taken into consideration when choosing which mesh size to use in order to capture appropriately-staged embryos. For example, pine somatic embryo dimensions are generally of length about 1.0 mm to about 5.0 mm and the diameter ranges from about 0.5 mm to about 2.0 mm. Accordingly, a person of skill in the art, once made aware of this disclosure, would be able to choose a suitable mesh size to use in order to manipulate embryos but prevent losing an unsuitable number of embryos by virtue of their falling through too-large openings in the mesh. Various mesh sizes can have a grid with pore sizes of 100, 150, 200, 250, 300, 350, 400, 450, 500, 550, 600, 650, 670, 700, 710, 750, 800, and 900 microns or any integer in between.

For example, the pores may preferably range from 400 microns to 900 microns, and more preferably range from 500 microns to 750 microns. In addition, the pores can have sizes in other suitable ranges, such as from 560 microns to 710 microns or from 600 microns to 670 microns. In certain cases, however, 800 microns may be too large for certain conifer cell lines. Since high polyethylene glycol concentrations yield smaller embryos, it may therefore be desirable to use sieve sizes that have pores smaller than 670 microns. Generally, the percent opening of the porous material can be within any suitable range, such as 48% or greater, 53% or greater, 56% or greater; however, it is preferred to have as great a percent opening as possible.

The wash unit 208 and the rinse unit 212 can be configured to wash and rinse, respectively, the embryos. The wash unit 208 and the rinse unit 212 are structurally similar to each other in certain respects. They can include cylindrical members 209 and 213, respectively, that can be made from the same material, such as a white polypropylene, and are configured to mate with the holding unit 202. The wash unit 208 and the rinse unit 212 can be configured to mate with the holding unit 202 in the same fashion as the holding unit 202 mates with the spray housing 122, through the use of an alignment mechanism 124. A proper alignment between the holding unit 202 and the wash unit 208 or the holding unit 202 and the rinse unit 212 may be desired to achieve an optimal cleaning effect. Position sensors (not shown), as described above, may be used to ensure proper alignment.

The wash unit 208 may or may not have a holding structure 210. The purpose of the holding structure 210 is to provide balance between the flow of the input fluid from the spray mechanism and the flow of the output fluid to the outlet mechanism due to the vacuum system. The holding structure 210 can be, for example, a porous material, such as a mesh material. Any suitable sizes and configuration of holes can be used so as to direct the fluid flow toward the outlet mechanism 18. If a mesh material is used, the overall diameter of the material preferably is 2.75" with 90 holes with a 1/16" diameter and 5 holes with a 3/8" diameter.

The rinse unit 212 also can have a fixed holding structure 214, which is used to support the removable raft 230 and can direct the flow of fluid to the outlet mechanism. The removable raft 230 can be removed from the rinse unit 212 so that the embryos can be removed from the rinse unit 212 by the operator by holding the removable raft 230 and pulling it out of the cylindrical member 213.

The holding structure 214 can be a porous material, such as a mesh material. If the wash unit 208 has a holding structure 210 made of porous material, preferably the porous material of the holding structure 214 of the rinse unit 212 has a smaller pore size. Also, the porous material of the holding structure 214 preferably has a smaller pore size than the porous material of the holding structure 206 of the holding unit 202. The reason for using the smaller pore size in the rinse unit 212 is that there are less cellular debris in the rinsing cycle than in the washing cycle. In addition, the smaller pore size will allow for a more uniform vacuum from the negative pressure source 20, which aids in the drying process of the embryos after the rinsing process, as will be described later. The holding structure 214 can be, for example, a plate with a 2.75" diameter with 132 holes in it. Ninety holes are 1/16" in diameter while 42 holes are 1/32" in diameter. In such an example, the holding structure 214 can have an external ring of 1/16" diameter holes that surround a collection of 1/16" diameter and 1/32" diameter holes. The 1/16" diameter holes within the external ring of /1;16" holes can be in the shape of a cross that has its intersection at the center of the external ring of 1/16" holes. The holding structure 214, however, can be any suitable configuration as long as flooding of the rinse unit with the fluid is avoided.

The removable raft 230 can also be a porous material, such as a mesh material. If a mesh material is used, the pore size can be smaller then the pore size of the mesh material 214 of the holding structure 214. For example, the removable raft can have a diameter of 2.70" and have a pore size in the range of 15 microns to 65 microns. More preferably, the pore size will be 33 microns.

In operation, the unwashed embryos are placed inside the holding unit 202 by an operator or by an automatic loading mechanism (not shown) such that the embryos are resting on the holding structure 206 and are contained within the cylindrical member 205 of the holding unit 202. After the unwashed embryos are loaded into the holding unit 202, the spray housing 122 covers the holding unit 202, and the holding unit 202 is mated with the wash unit 208. One or more washing cycles are performed depending on the level of cellular debris and the state of the embryos. The operator can look through the transparent material of the cylindrical member 205 of the holding unit 202 and see the results of the washing. If the operator is not satisfied with the results, the operator may order another washing operation using an input mechanism in the controller 22.

Figure 6:
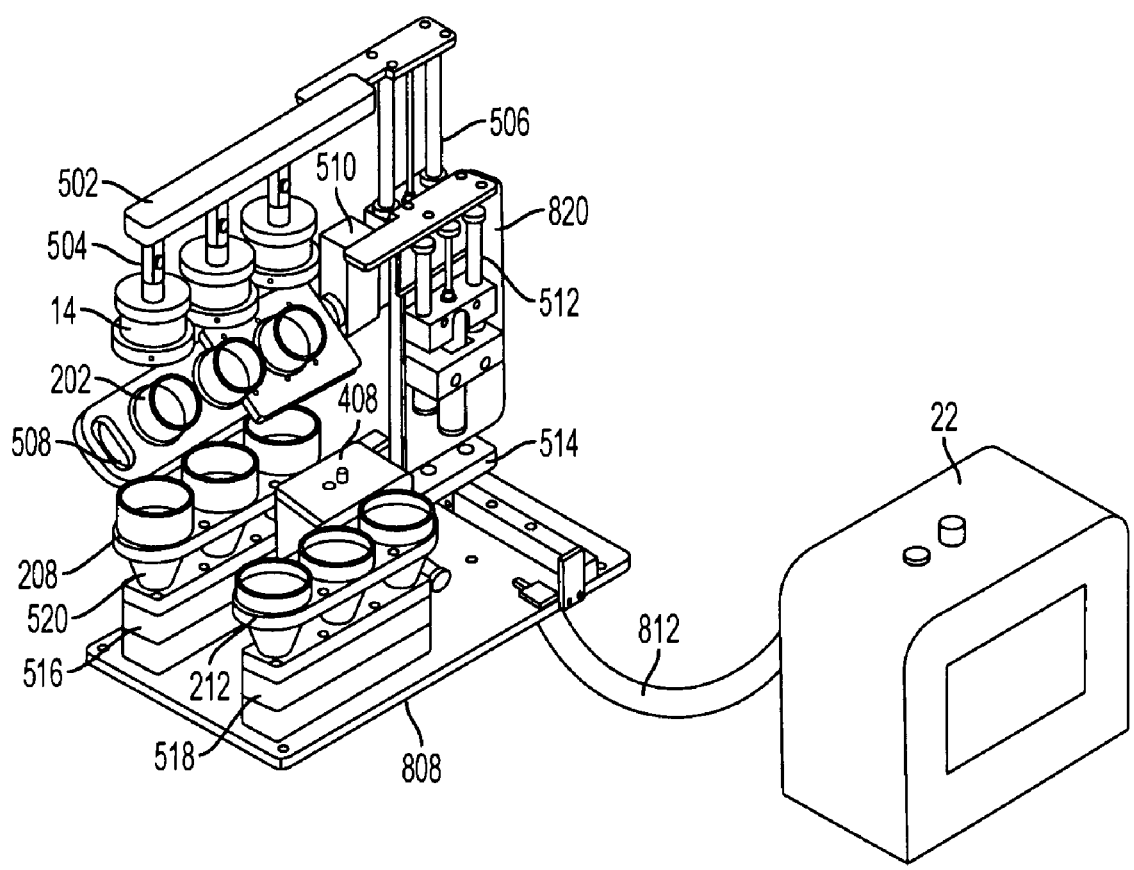
FIG. 6 is a perspective view of the plant embryo cleaning apparatus of FIG. 2.

After the washing cycle is complete, the spray housing 122 is disengaged from the holding unit 202 and is moved horizontally either manually or automatically using a horizontal moving structure (for example, the horizontal moving structure 514 in FIG. 6 as described below) to the rinse unit 212. The holding unit 202 then may be turned over either manually or automatically using a rotational device (for example, the rotational device 510 in FIG. 6 as described below) so that the washed embryos are underneath the holding structure 206. The washed embryos are held in place on the holding structure 206 by the surface tension of the washing fluid that is retained in the holding unit 202 after the washing cycle. The holding unit 202 is mated with the spray housing 122 and the rinse unit 212 (as described below) so that a rinsing cycle is performed. During the rinsing cycle, the embryos will be forced by the rinsing spray off of the holding structure 206 and land on the removable raft 230 of the rinse unit 212. Once the rinsing cycle is complete, the embryos can be removed from the rinse unit 212 by holding the removable raft 230.

The outlet mechanism 18 can be configured to receive the used cleaning fluid and cellular debris from the embryos that fall through the holding structures 210 and 214 during the washing and rinsing cycles. The outlet mechanism 18, as seen in FIGS. 2 and 4, can comprise a first outlet 216 that is in fluid communication with the wash unit 208 and a second outlet 218 that is in fluid communication with the rinse unit 212. The cleaning fluid flows out of the first and second outlets during the washing and rinsing cycles respectively. As shown in FIG. 5, the first outlet 216 is connected to a first fluid line 404 while the second outlet 218 is connected to a second fluid line 406.

FIG. 5 shows a schematic drawing of the negative pressure source 20, which during the washing and rinsing cycles can be configured to draw the cleaning fluid and the cellular debris from the embryos during the washing and rinsing operations. Thus, the vacuum can aid in reducing the residual cellular debris left on the embryos. In addition, the air movement caused by the vacuum also dries the embryos after the rinsing process. In one embodiment of the present invention, the negative pressure can range from −0.5 psi to −1.5 psi, and more preferably is −1.44 psi. However, the negative pressure can be any suitable pressure. The negative pressure source 20 preferably includes and an electric control valve 408, a flow section 416, a vacuum pump 402, a check valve 410, and a draining outlet 412.

The electronically controlled valve 408 is connected to the first and second fluid lines 404, 406. The electronically controlled valve 408 can be any kind of electronically controllable valve, such as a solenoid valve. The electronically controlled valve 408 is controlled by the controller 22 in FIG. 2, which during the washing cycle commands the electronically controlled valve 408 to connect the fluid line 404 to a fluid line 414 while closing the passage to fluid line 406 and the rinse unit 212. The fluid line 414 can be any suitable piping or tubing, such as one inch diameter PVC pipe. Conversely, during the rinsing cycle, the controller 22 commands the electronically controlled valve 408 to connect the fluid line 406 to the fluid line 414 while closing the passage to the fluid line 404 and the wash unit 208. Thus, the electronically controlled valve 408 is controlled by the controller 22 in FIG. 2 to connect the vacuum pump 402 to either the wash unit 208 or the rinse unit 212 depending on the state of the cleaning cycle.

The flow section 416 receives fluid from the fluid line 414. The flow section can be any suitable piping or tubing, such as four inch diameter PVC pipe. The flow section 416 can have an upper section 418 and a lower section 420. The upper section 418 can lead upward to the vacuum pump 402. The lower section 410 leads downward toward the drain outlet 412 via fluid lines 224 and 226, which can be any suitable piping or tubing, such as two inch diameter PVC pipes. The flow section 416 acts as an air-fluid separator in which the air is sucked upwards towards the vacuum pump 402 via the upper section 418 while the cleaning fluid and residue flows downward via the lower section 420 due to the force of gravity. Additionally or alternatively, the residue or cellular debris from the cleaning station 16 may be collected using a conventional polyester trap placed in the outlet mechanism 18.

The flow section 416 is connected to the vacuum pump 402 by a fluid line 444. The fluid line 444 can include a pressure regulator 430, which is used to monitor and control the level of pressure in the vacuum system. This information can be used by the controller to monitor and balance the flow of the inlet fluid with the flow of the outlet fluid (as described below).

The vacuum pump 402 can be any conventional vacuum device. For example, the pump can be a MEDAES MedPlus Vacuum Plant (Model No. 6911-XYS-NAME).

The check valve 410 operates as a function of the weight of the liquid and the force of the vacuum pump 402. When the vacuum pump 402 is initially started, the check valve 410 is pulled shut. The cleaning fluid starts to collect behind the shut check valve 410. The fluid continues to accumulate in the lower section 420 until it reaches a predetermined height H. H is the critical height where the weight of the fluid equals the force of the vacuum pump 402. When this critical height is reached, the check valve 410 opens and allows the fluid to drain out, for example, into the sewer. The column of fluid in the flow section 416 prevents air from being drawn into the system, thus preserving the vacuum while the fluid is draining. Thus, a steady stream of used fluid and cellular debris is discharged from the system.

A vent 432 can be added in the fluid line 226 located between the check valve 410 and the drain outlet 412. This vent is can be used, for example, to minimize air in a sewer-from being pulled into the vacuum system upon initial start up of the vacuum system before the check valve 410 is pulled shut.

As a safety precaution, the apparatus can include a fluid level sensor and alarm 220 located within the flow section 416 that can be used to indicate that the fluid level in the flow section 416 is too high due to some back-up or clogging in the draining system. Such clogging may damage the vacuum pump 402. The fluid level sensor 220 will generate a signal 222 that is transmitted back to the controller 22 either by transmission line or wireless communication. When the controller 22 receives the warning signal, the controller can issue an audio or visual alarm to the operator alerting him or her of the possibility of a clog in the draining system. Alternatively, the controller may automatically shut down the system in response to a warning from the fluid level sensor 220.

An apparatus according to the present invention can be configured to synchronize the input fluid that enters the cleaning station 16 and the output fluid through the outlet mechanism 18. Considering the ratio of input fluid to output fluid could prevent damage to the embryos due to the velocity or pressure of the fluid as it acts on the embryos during the washing and rinsing process. Thus, it may be desirable to select the magnitude of the line pressure, the magnitude of the negative pressure, and the design of the nozzle such that a suitable fluid flow and fluid flow pattern is achieved to achieve optimal cleaning conditions while preventing any damage to the embryos. Thus, the system should be balanced when selecting the components of the system, particularly the nozzle, the negative pressure source, the pores sizes of the supporting structures, and the supply valves.

The controller 22 is configured to control at least one, and preferably all, of the cleaning-fluid source 11, the fluid-conditioning system 12, the spray mechanism 14, the cleaning station 16, the outlet mechanism 18, and the negative pressure source 20, either automatically or by operator control. The controller 22 can be connected to and control these components by conventional means. For example, the controller 22 can be connected by one or more wire transmission lines 812 to the various devices that it operates and to the sensors which send it information.

The controller 22 may comprise a display, one or more microprocessors, memories, input/output lines, a graphical user interface, and/or one or more operation buttons. The controller 22 can include, for example, a small Programmable Logic Controller (PLC) (e.g. Direct Logic, model number DL-05) with an operator interface for operator inputs, operational parameters, error messages, and production reports. A PLC with more digital inputs and outputs or a PC-based computer can be used for a fully automated system. For example, the controller may contain data processing programs in one or more microprocessors for processing data related to the position and fluid level sensors as stated above and programs for performing operational commands for controlling the electronically controlled valve 108, the vacuum pump 402, the electronically controlled valve 408, the pneumatic cylinder 506, a pneumatic cylinder 512, and an automatic horizontal moving structure 514 (which will be described later). Furthermore, the controller can be configured to control the flow of input liquid through the spray mechanism 14 and/or the pressure of input fluid sprayed by the spray mechanism 14 using the pressure regulator 150. If such pressure control is used, the controller can be configured to maintain the pressure of the input fluid within a suitable range so as to provide a suitable pressure on the embryo to remove the cellular debris, for example, a range of about 22 psi to about 45 psi. In one embodiment according to the present invention, the input fluid pressure is about 35 psi.

As mentioned above, the choice of nozzle design, input fluid pressure and vacuum pressure for the system must be chosen carefully so as to effectively clean the embryos without damaging them. These elements should be chosen so that the impact or impingement of the spray on the embryos is within a specified range for effective but safe cleaning. The impingement on the embryos is a function of the nozzle design, input fluid pressure, and vacuum pressure. For example, the nozzle, inlet pressure, and vacuum pressure preferably are designed to deliver an impingement of the input liquid within a range of 0.00506 to 0.027 pounds per square inch at a normalized standard distance of twelve inches, and more preferably about 0.018 pounds per square inch at a normalized standard distance of twelve inches. Impingement is defined by the formula below:

$$\text{Impingement}(\text{impact}/\text{inch}^2) = I_{th} \times (\% \text{ Impact}/\text{inch}^2),$$

where $I_{th} = 0.526 \times C_p \times \sqrt{P}$ and where $I_{th}$ is the theoretical impact (pounds-force), $C_p$ is the nozzle capacity (gallons per min) at pressure P (psi), and % Impact is based on data collected at a 12 inch distance from the nozzle exit orifice.

The controller can be designed to use the pressure regulator 150 and/or the pressure regulator 430 to alter the impacts per square inch without the necessity of changing the nozzle.

The controller can be programmed to make the entire cleaning operation automatic from the time when the unwashed embryos are loaded into the holding unit to the time when they are removed from the rinse unit. Alternatively, the controller can be programmed to make only portions of the cleaning operation automatic. For example, the washing and rinsing operations can be automated while the movement of the holding units in the vertical and/or horizontal directions are operator-controlled either manually (by hand) or via the controller. Another example can be to have the entire cleaning operation automated while provided the operator with the option to halt the cleaning operation and repeat a particular operation if desired. For example, if the operator wishes an additional washing operation, the operation can use the controller to halt the entire cleaning operation and repeat the washing operation for as many washing cycles that he or she desires.

The controller 22 preferably also is programmable so that it can regulate the frequency and duration of the washing and rinsing operations based on input from the operator for a particular operational run. The input from the operation can be based on the type of embryos and cellular debris that are being dealt with in a particular operational run. Thus, the controller can be programmed to set the impingement on the embryos, the frequency of the washing and/or rinsing operations, or the length of time for the washing and/or rinsing operations by the operator that is based upon the type of embryo and the cellular debris. An example of a suitable duty cycle for the wash and rinse cycle can be 30 seconds for the washing operation and 2 seconds for the rinsing operation.

An example of a controller according to the present invention is presented in FIG. 2. In this embodiment, the controller includes an OFF/ON switch 702, a graphical interface 704, and a display 706. The display 706 may be part of the graphical interface 704 or may be a separate component. The display 706 may display operational variables and parameters to the operator. For example, the number of cleaning operations performed, position sensor information, or any failures regarding the position sensors, vacuum system, washing and rinsing cycles, etc. can be shown on the display 706. The display allows an operator to input parameters for the wash cycle, input parameters for the rinse cycle, and the ability to repeat the wash cycle if desired. The wash cycle set-up may be used to set the cycle time or the frequency of washing operations for a particular operational run. Alternatively, instead of a graphical interface, other input devices may be used, such as a keyboard or a foot pedal.

FIGS. 2-5 provide a schematic illustration of an embodiment of the present invention. This schematic illustration shows one spray mechanism and one cleaning station (i.e., one holding unit, one wash unit, and one rinse unit); however, a plurality of spray mechanisms and cleaning stations preferably are employed. FIGS. 6, 8A-8B, 9A-9B, and 10A-10D show a particular implementation of this embodiment of the present invention. It has three spray mechanisms 14 and three cleaning stations (i.e., three holding units 202, three wash units 208, and three rinse units 212). The entire apparatus can be placed on a base 808, which may include leg supports 810 (as seen in FIGS. 10A-10D).

Figure 8A:
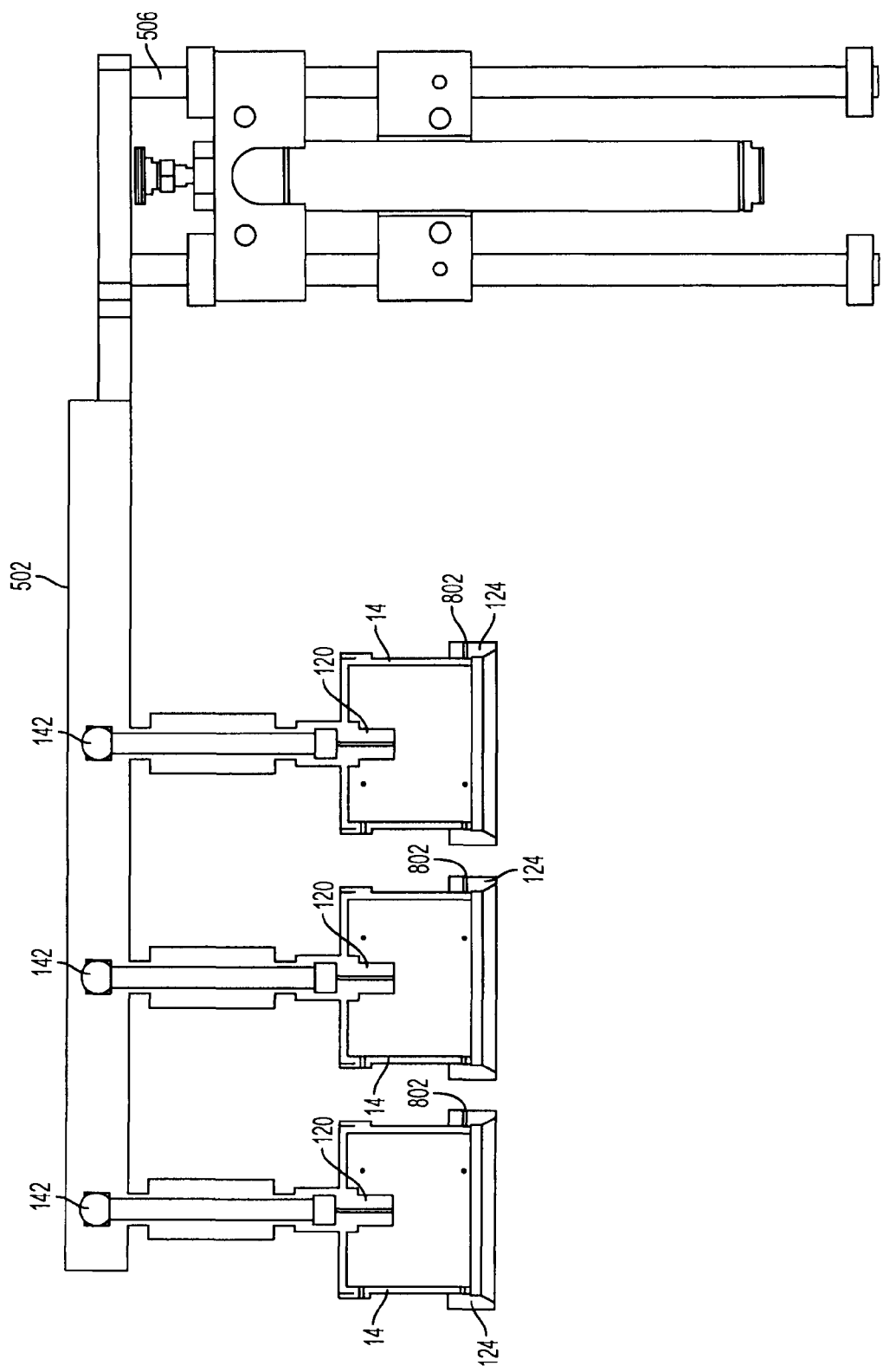
FIGS. 8A and 8B are a cross-sectional view and a side view, respectively, of a spray mechanism, a mounting bracket, and a pneumatic cylinder of the plant embryo cleaning apparatus of FIG. 2.
Figure 8B:
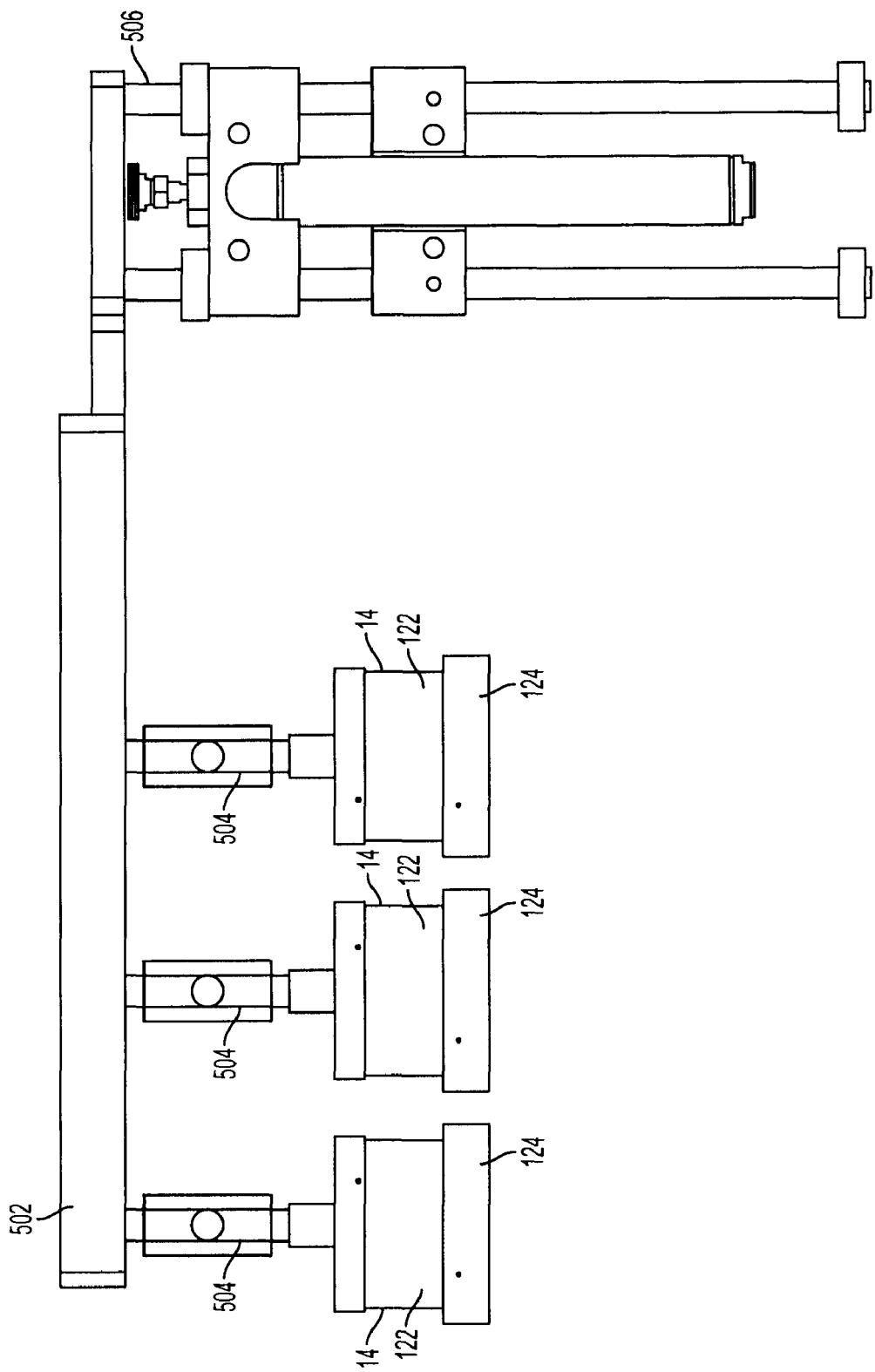

FIGS. 8A and 8B show a cross-sectional view and a side view of the spray mechanisms 14, a mounting bracket 502, and a pneumatic cylinder 506. FIG. 8A shows water inlet ports 142 and nozzles 120. The fluid from the fluid source 11 is fed through the inlet ports 142 to the nozzles 120. For example, the three nozzles 120 can be the type made by AllSpray LLC (Model Number of FCS 65 Deg) and have a capacity of 1.40 gpm at 40 psi. The spray mechanisms 14 include spray housings 122 (made from clear polycarbonate, glass, or other transparent material) with alignment mechanisms 124 in the form of tubular sleeves that will fit around the holding units 202. The alignment mechanisms 124 are attached to their respective housings by set screws that are placed inside threaded apertures 802. The three spray mechanisms 14 are fixed to the mounting bracket 502 via stems 504 so that they all move vertically and horizontally as one unit. The mounting bracket 502 is fixed to the pneumatic cylinder 506, which causes vertical movement of the spray mechanisms 14. The pneumatic cylinder 506 can be controlled by the controller 22.

Figure 9A:
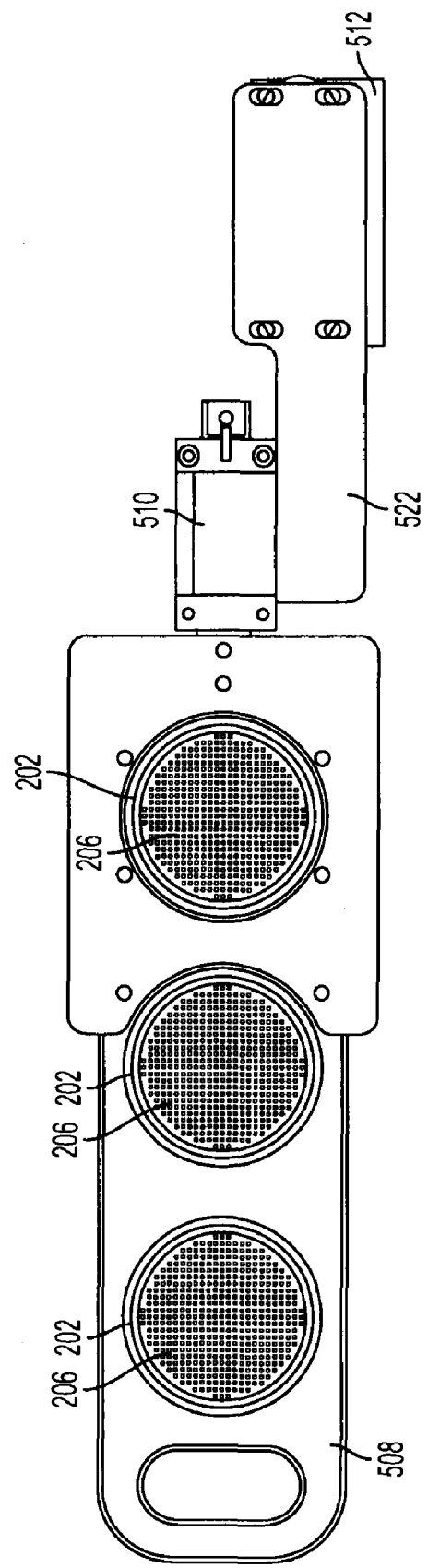
FIGS. 9A and 9B are a plan view and a cross-sectional view, respectively, of holding units, a mounting bracket, a rotational device, and a pneumatic cylinder of the plant embryo cleaning apparatus of FIG. 2.
Figure 9B:
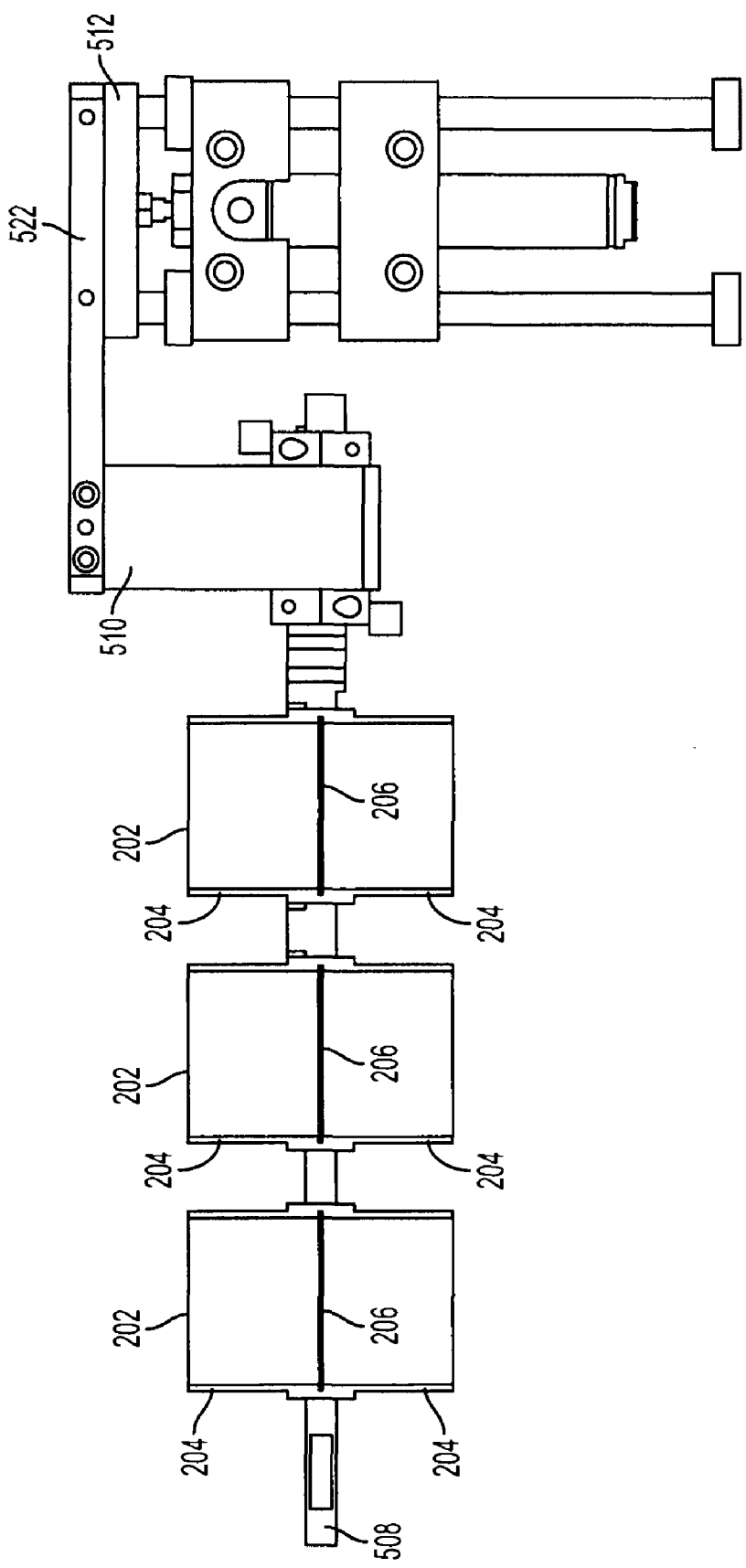

The cleaning stations include three holding units 202, three wash units 208, and three rinse units 212. FIGS. 9A and 9B show a plan view and a cross-sectional view of the holding units 202, a mounting plate 508, a rotational device 510, and a pneumatic cylinder 512. The holding units 202 have uniform external surfaces 204 which fit inside the alignment mechanisms 124 of the spray mechanisms 14 while also being able to fit inside the wash units 208 and the rinse units 212.

The holding units 202 are fixed to the mounting plate 508 such that all the holding units move vertically, horizontally, and rotationally as one unit. The mounting plate 508 is connected to a rotational device 510 which is mounted on another pneumatic cylinder 512 via a cylinder mounting bracket 522. The rotational device 510 causes the holding units 202 to rotate after the washing cycle but before the rinsing cycle such that the embryos will be collected onto the removable raft 230 of the rinse units 212 after the rinsing cycle. As previously mentioned, the embryos will stay in place due to the surface tension of the fluid remaining in the holding unit 202 after the washing cycle. The pneumatic cylinder 512 moves the holding units in a vertical direction so that the holding units 202 can be lowered to mate with the wash units 208, lifted to remove them from the wash units, lowered to mate with the rinse units 212, and lifted to remove them from the rinse units. The rotational device 510 and pneumatic cylinder 512 can be controlled by the controller 22.

Figure 10A:
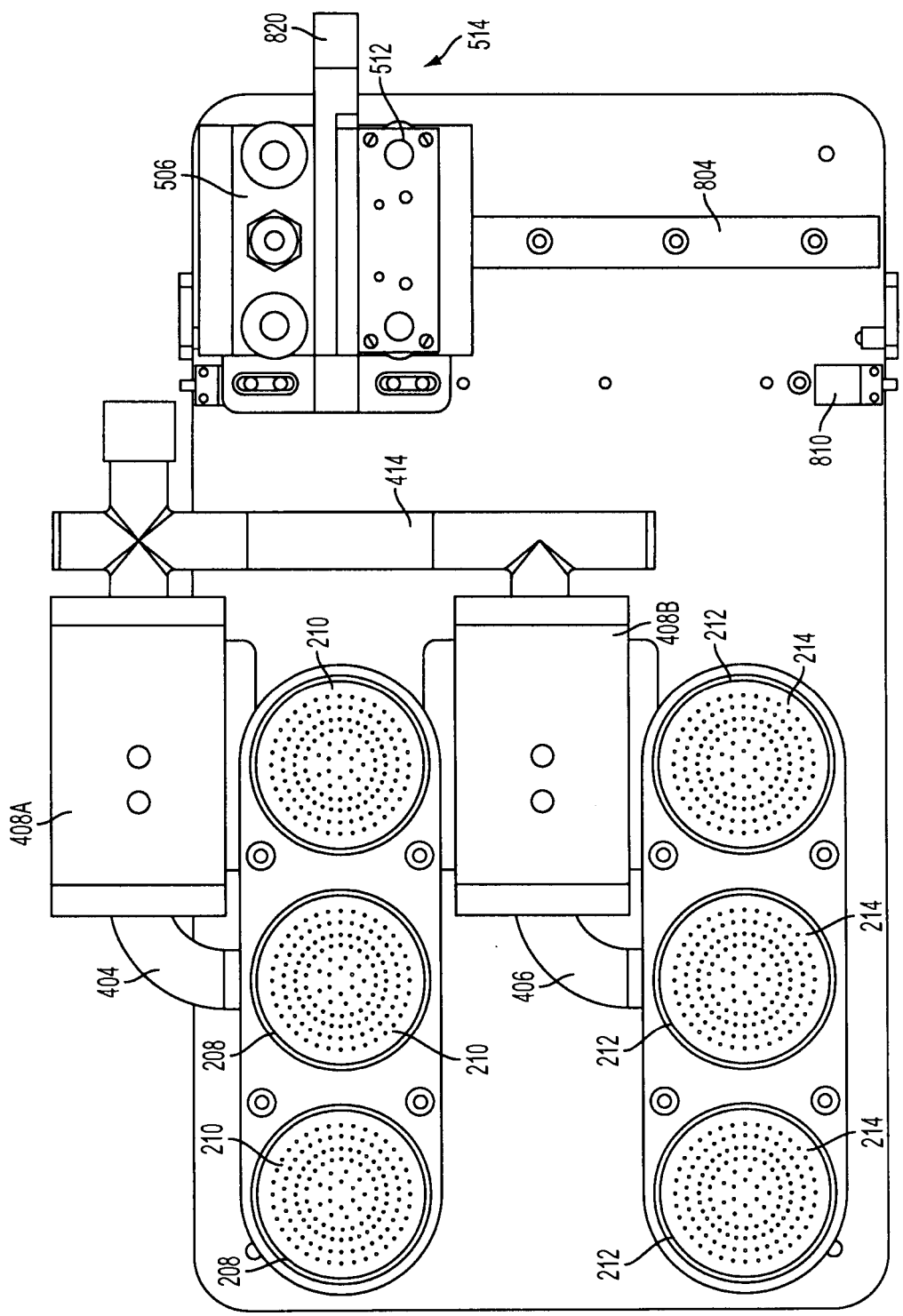
FIG. 10A is a plan view of wash units, rinse units, two electronic vacuum valves, and a horizontal moving structure of the plant embryo cleaning apparatus of FIG. 2.
Figure 10B:
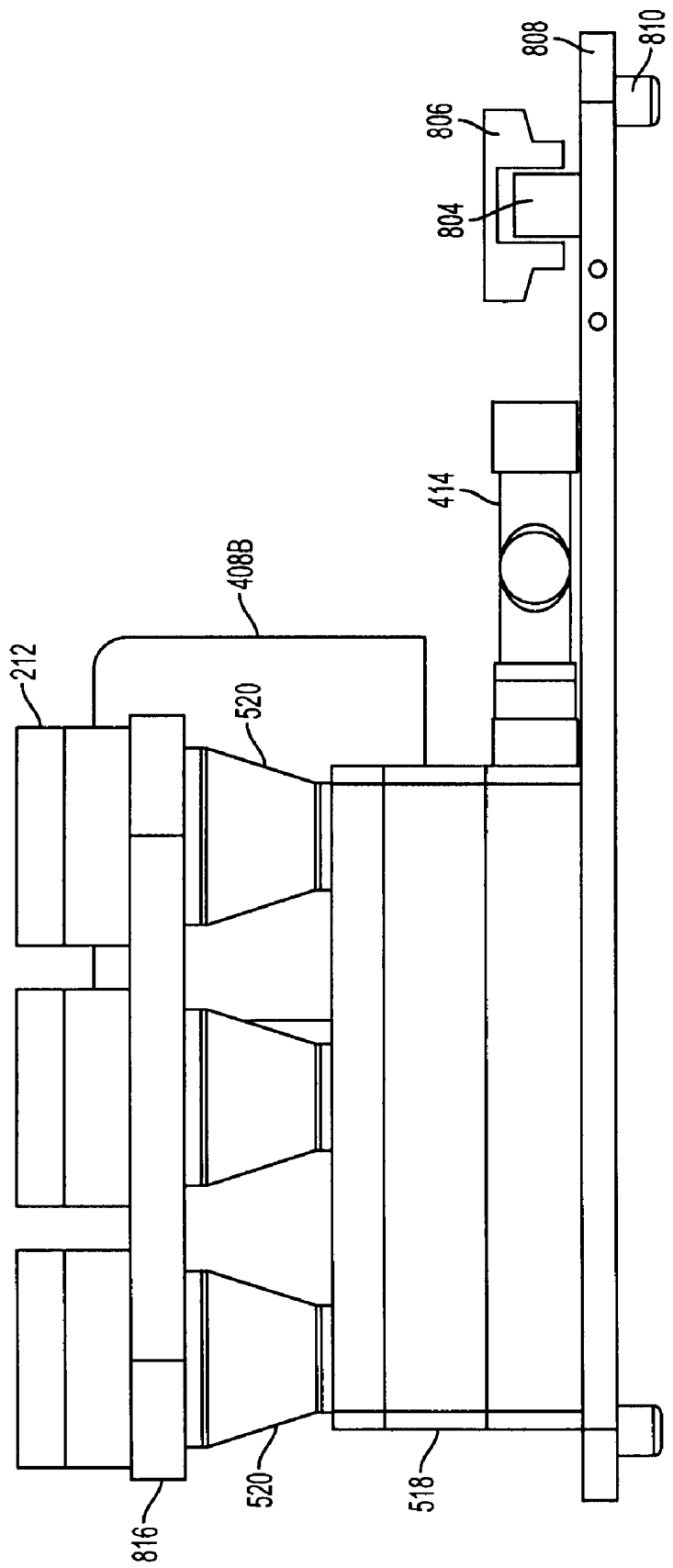
FIG. 10B is a side view of the rinse units, a vacuum manifold, and output funnels of the plant embryo cleaning apparatus of FIG. 2.
Figure 10C:
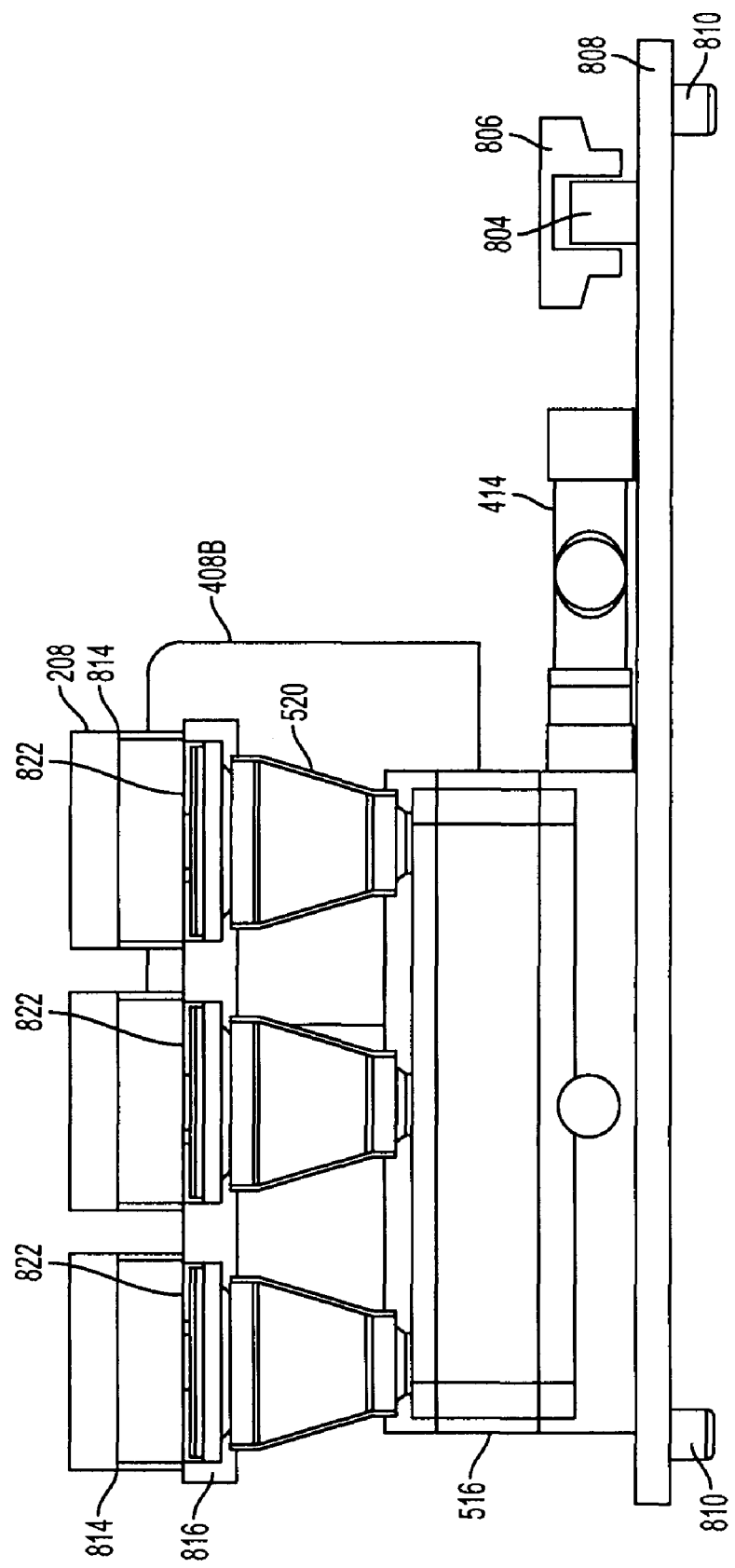
FIG. 10C is a cross-sectional view showing the wash units, the output funnels, the vacuum manifold, and a horizontal rail of the plant embryo cleaning apparatus of FIG. 2.
Figure 10D:
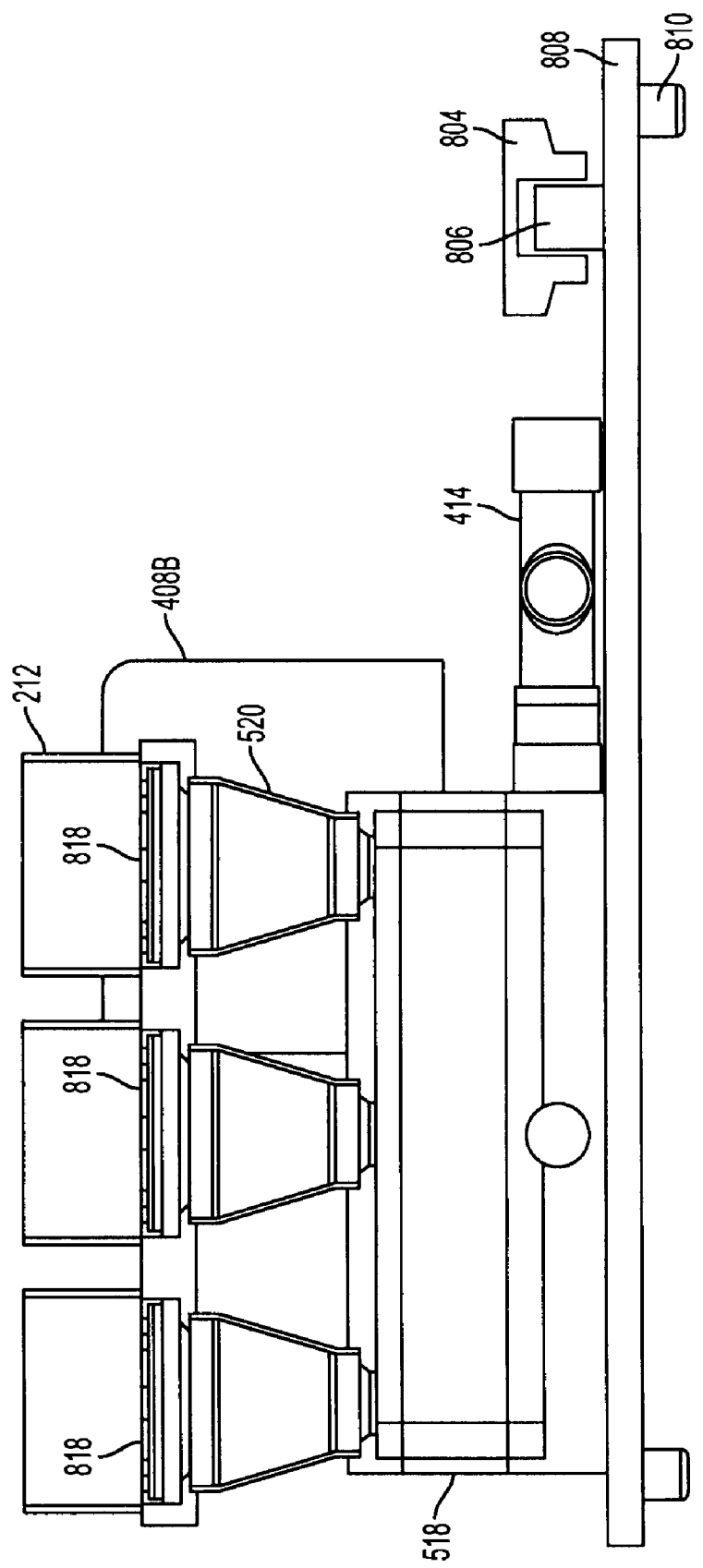
FIG. 10D is a cross-sectional view showing the rinse unit, the output funnels, the vacuum manifold, and the horizontal rail of the plant embryo cleaning apparatus of FIG. 2.

FIG. 10A shows a plan view of the wash units 208, the rinse units 212, and two electronic vacuum valves 408A and 408B. FIG. 10B shows a side view of the rinse units 212, a vacuum manifold 518, and output funnels 520. FIG. 10C shows a cross-sectional view of the wash units 208, the output funnels 520, a vacuum manifold 516, and the horizontal rail 804. FIG. 10D shows a cross-sectional view of the rinse unit 212, the output funnels 520, the vacuum manifold 518, and the horizontal rail 804.

Both of the pneumatic cylinders 506 and 512 are mounted on a horizontal moving structure 514. The horizontal moving structure 514 comprises a horizontal rail 804 mounted on the base 808. The pneumatic cylinders 506 and 512 are mounted on a vertical plate 820, which is mounted on a carrier 806. The carrier can be manually slid along the horizontal rail 804 when the spray mechanism and the holding units are moved from the wash units to the rinse units and vice versa. Alternatively, the pneumatic cylinder 506 with the spray mechanisms 16 and the pneumatic cylinder 512 with the holding units 202 can be moved automatically by the controller 22 through the use of a moving stage that is powered by another pneumatic cylinder, a driven linear stage, or another motion generated apparatus known in the art.

The wash units can include a ledge 814 on the inside of the wash units 208 to provide a location for the holding units to rest during the washing process. The holding structure 210 can be placed at the ledge 814 or on the lower surface 822 of the wash units 208. The rinse units 212 have a lower surface 818 in which a fixed holding structure 214 is placed. A removable raft 230 is then placed on the fixed holding structure 214 so as to collect the rinsed embryos after the cleaning process. The washing and rinse units both connect to an outlet mechanism that may comprise two sets of funnels 520 that are in fluid communication with two manifolds 516 and 518. The funnels can be, for example, Model Number 07-33/10 made by Nalgene Labware, which has a drainage hole diameter of 1/32".

The manifold 516 is in fluid communication with fluid line 404, which is connected to a first electronically controlled valve 408A. The manifold 518 is in fluid communication with fluid line 406, which is connected to a second electronically controlled valve 408B. Both valves are connected to a vacuum and draining system (not shown) via fluid line 414 and both are in communication with the controller so that one of the electronically controlled valves is opened and another is closed depending on the stage of the cleaning process. For example, during the washing cycle, the controller 22 commands the electronically controlled valve 408A to open, which connects the vacuum and draining system to the manifold 516 and the wash units 208 but commands the electronically controlled valve 408B to close, which cuts off the manifold 518 and the rinse units 212 to the vacuum and draining system. Conversely, during the rinsing cycle, the controller 22 commands the electronically controlled valve 408B to open, which connects the vacuum and draining system to the manifold 518 and the rinse units 212 but commands the electronically controlled valve 408A to close, which cuts off the manifold 516 and the wash units 208 to the vacuum and draining system.

Next, the method of preparing multiple plant embryos for plant production will be discussed in reference to FIGS. 7A-7F. The method may comprise the step of supplying multiple plant embryos in a cleaning station. In step 1 in FIG. 7A, the operator may load the embryos into the holding units 202 (for example, approximately 500 embryos can be placed in each holding unit 202) by tilting the holding units, such as by 45 degrees, towards the operator for ease of loading. Alternatively, the holding units may be automatically loaded via conveyor belt, robotic arm, or the like (not shown). Also, the removable raft 230 is placed in the rinse units 212 at this time.

Figure 7A:
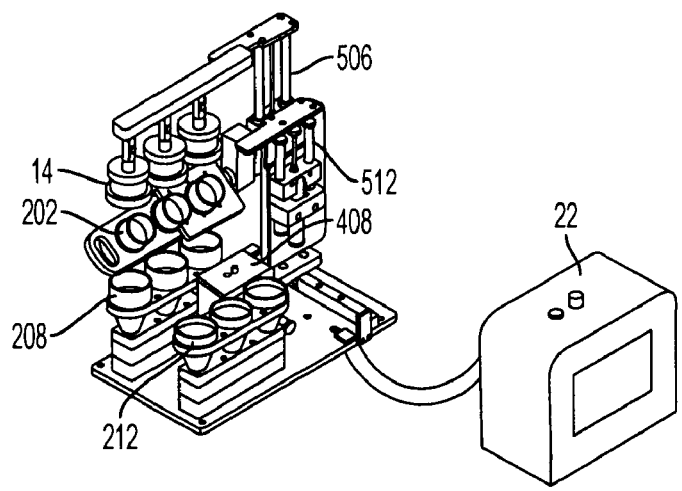
FIGS. 7A to 7F are perspective views of the of the plant embryo cleaning apparatus of FIG. 2 in operation.
Figure 7B:
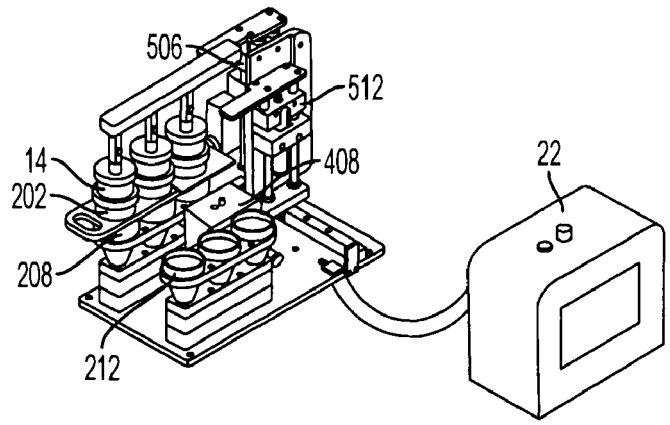

In step 2 in FIG. 7B, the operator or the controller may vertically align the spraying mechanisms 14, the holding units 202, and the wash units 208 vertically and initiate the washing process. The operator could initiate the washing operation with the controller using, for example, a foot switch, a keyboard, or a graphical interface. The controller 22 can verify that the spray mechanisms 14, the holding units 202, and the wash units 208 are in the correct position and orientation by reading in the information by the position sensors (not shown). The controller 22 then activates the two pneumatic cylinders 506 and 512 to lower the spray assembly 14 and the holding units 208 into the wash position. In the lowered position, additional sensors can verify that the assemblies were registered in the correct positions before the wash cycle begins. These additional sensors can be proximity sensors known in the art. As previously discussed, the proximity sensors can be inductive, capacitive, ultrasonic, optical, or electrical contacting sensors.

The preprogrammed wash cycle is then executed. Cleaning fluid is permitted to flow through the electronically controlled valve 108, the filter 110, the UV sterilizer 112, and the nozzle 120 by commands issued by the controller 22 to the electronically controlled valve 108 in FIG. 3. Media, used cleaning fluid, and extraneous plant tissue are pulled away using the negative pressure source by automatically opening the electric control valve 408. A negative pressure is supplied to the wash units 208 for controlling the flow of the output fluid. The negative pressure supplied to the wash units is controlled by the controller 22, which issues the operational command to the electric control valve 408A to open (while keeping the electric control valve 408B closed).

Figure 7C:
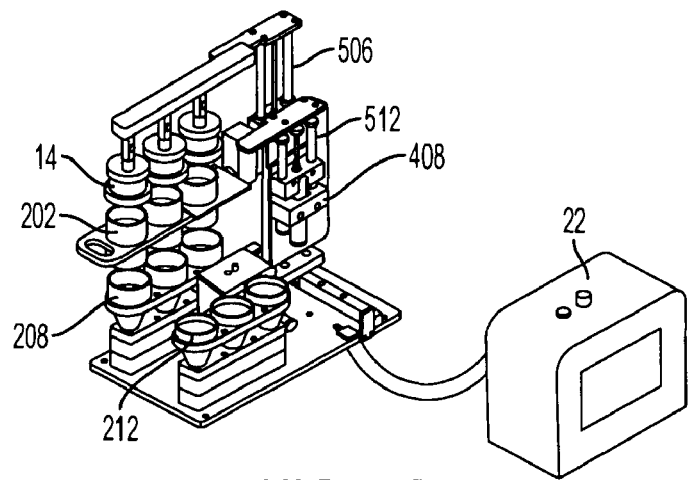

In step 3 in FIG. 7C, after the washing cycle is completed, the electronically controlled valve 108 shuts off the fluid flow and the control valve 408A is closed. The controller can automatically raise the spray mechanisms 14 and holding units 202 using the pneumatic cylinders 506 and 512. However, if the cellular debris is not completely washed from the embryos, the operator could intervene and initiate another wash cycle by inputting a command into the controller by using, for example, a foot switch, a graphical interface, or a keyboard.

Figure 7D:
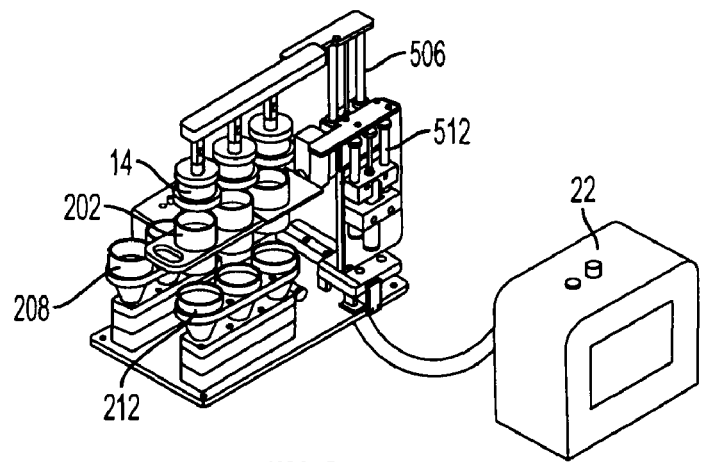

In step 4 in FIG. 7D, after all the washing operations are complete, the operator or the controller moves the pneumatic cylinders 506 and 512 (with the spray mechanisms 14 and the holding units 202) horizontally towards the rinse units 212. When the holding units 202 move toward the rinse units 212, the operator or the controller 22 may rotate the holding units 180 degrees so that the embryos are located on the bottom side of the holding structure 206. The embryos are retained inside the holding units 202 by the surface tension of the remaining fluid inside the holding unit 202 after the washing operation.

Figure 7E:
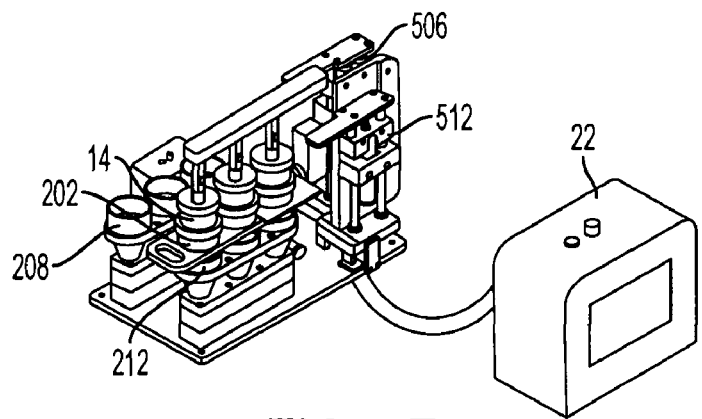

In step 5 in FIG. 7E, the controller 22 and proximity sensors ensure proper alignment before proceeding. The controller 22 then activates the two pneumatic cylinders 506 and 512 to lower the spray mechanism 14 and the holding units 202 into the rinse position. Once the spray mechanisms 14, the holding units 202, and the rinse units 212 are mated with each other, the operator or the controller 22 may initiate the rinse cycle. Cleaning fluid is permitted to flow through the electronically controlled valve 108, the filter 110, the UV sterilizer 112, and the nozzle 120 by commands issued by the controller 22, which controls the electronically controlled valve 108. A negative pressure is supplied to the rinse units 212 for controlling the flow of the output fluid. The negative pressure supplied to the rinse units is controlled by the controller 22, which issues the operational command to the electric control valve 408B to open (while the electric control valve 408A is remained closed).

The time between the starting of the vacuum and the delivery of the fluid is important so as to ensure an even distribution of spray onto the embryos on the holding structure 214. Because the delivery of fluid is balanced with the negative pressure source for a particular spray pattern, the establishment of a suitable vacuum pressure prior to the delivery of fluid is an important consideration. In addition, the operation of the check valve 410 is dependent on the vacuum starting up before the delivery of fluid.

An example of a preferred timing of the fluid flow and vacuum system during the washing and rinsing processes is as follows. For the washing process, the vacuum system initially starts up. After five seconds of vacuum (but it can range from 0-10 seconds), the cleaning fluid flow is initiated. The fluid flow and vacuum are run together for 30 seconds during the washing process (but it can range from 0-80 seconds). The fluid flow is shut off first and the vacuum continues to run for another 7 seconds (but it can range from 0-10 seconds).

For the rinsing process, the fluid flow is initiated first and runs for 3 seconds (but it can range from 0-10 seconds). The vacuum pump is initiated after the fluid flow has run for 1 second (but it can range from 0-10 seconds). The fluid flow is shut off first and the vacuum continues to run for another 10 second (but it can range from 0-80 seconds).

The fluid entering the spray mechanism during the washing operation may be a different type of liquid from the liquid entering the spray mechanism during the rinsing operation. For example, the liquid entering the spray mechanism during the washing operation may simply be sterilized and filtered water while the liquid entering the spray mechanism during the rinsing operation may be sterilized and filtered water with an additive, such as a growth hormone. In such a situation, an electronically controlled valve may be used to choose between two kinds of fluid sources for entry into the spray mechanism. Alternatively, the liquid used in the washing operation may be the same type of liquid used in the rinsing operation, such as filtered and sterilized tap water.

Figure 7F:
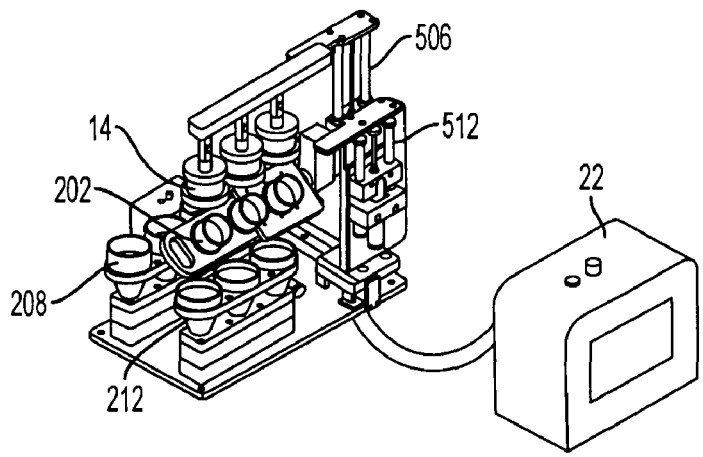

In step 6 in FIG. 7F, at the end of the rinsing operation, the controller 22 raises the holding units 202 and the spray mechanism 14 using the pneumatic cylinders 506 and 512 so that the operator or the controller could tilt and slide the holding units away from the rinse units 212. The rinsed embryos can be collected by removing the removable raft 230 for the next stage of the production process. The apparatus can start the process over again by loading new unwashed embryos into the holding units 202 and moving the holding units 202 back toward the wash units 208.

The entire cleaning apparatus can be located in a sterile environment, e.g., a laminar flow hood or HEPA-filtered chamber. In the case of use in a laminar flow hood, it is important to optimize the design and orientation of the components of the apparatus so as to minimize the redirection of air in the hood.

Some components, such as the holding units, the wash units, and the rinse units can be configured to be placed in an autoclave for cleaning and sterilization procedures for the individual parts. Also, contact surfaces of the components can be placed in an autoclave. Alternatively or additionally, the cleaning apparatus can have the additional functionality of cleaning in place (CIP) for good quality control by the simple addition of plumbing, a pump, and an automatically controlled valve to sterilize the machine during the non-production hours without dismantling the cleaning apparatus. The fluid that can be pumped into the system during the CIP can be, for example, bleach or a diluted concentration thereof or hydrogen peroxide or a diluted concentration thereof. This ensures maximum uptime while maintaining sterile conditions.

An apparatus according to the present invention also can be configured to automatically input nutrients and antifungal materials as pretreatment and for conditioning.

Thus, the washing method and apparatus according to various embodiments of the present invention can be rapid, inexpensive, highly efficient, and increases the consistency in quality since the method and apparatus can entail washing and rinsing large numbers of plant embryos en masse, rather than individually.

In addition, because the apparatus can be partially or fully automated, human involvement in the cleaning operation is minimized. As a result, (1) fewer humans are necessary to clean large number of plant embryos since the apparatus and method is capable of cleaning thousands of embryos; (2) there is less chance of contamination caused by human contact with the embryos; (3) greater consistency can be achieved in the cleaning operation which leads to better quality control; and (4) there is better control of the cleaning process since all operator input variables are handled by the controller.

Furthermore, the apparatus and method is expandable such that there can be several cleaning stations in one apparatus. Thus, the apparatus can have one, two, three, four, five or more cleaning stations at one time such that output can be greatly increased.

There can be many potential benefits derived from using the above described method and apparatus for washing embryos. For example, it has been discovered that the washing and rinsing substantially removes poly ethylene glycol (PEG) molecules that adhere to embryo surfaces during their exposure to embryogenic development media. This is a significant discovery because the removal of PEG via washing and rinsing eliminates several time-consuming and burdensome steps in the traditional harvesting protocol. For example, it is not necessary to store mass harvested embryos on gelled medium in the cold for 3-4 weeks to allow diffusion of PEG away from the embryos. Thus, according to one embodiment of the present invention, it is desired to configure the spray mechanism and cleaning station remove PEG from the plant embryos.

An additional use or advantage for the above cleaning apparatus can be as a sorter for embryos by simply changing the holding structures in the holding unit 202 and the wash unit 208. For example, by selecting a suitable mesh structure for the holding structure 206 in the holding unit 202, it is possible to remove an undesirable size and/or number of embryos in the harvesting process by having the cleaning fluid push the undesired embryos into the outlet mechanism 18 and into the draining system.

Although the aforementioned describes embodiments of the invention, the invention is not so restricted. Given the disclosure of the present invention, one versed in the art would appreciate that there may be other embodiments and modifications within the scope and sprit of the invention. Accordingly, all modifications attainable by one versed in the art from the present disclosure within the scope and spirit of the present invention are to be included as further embodiments of the present invention. The scope of the present invention is to be defined as set forth in the following claims.

Tables

TABLE 1

Table 1. Complete medium formulation. Refer to Table 2 for the inorganic salt and vitamin components. All medium pH to 5.8 prior to autoclave sterilization.

| Component | WV5 INIT gel | DCR MAINT gel | DCR MAINT liquid | Mi3 BULKUP gel | Mi3 BULKUP liquid | MSG EPROD gel | 2M21 COND gel | 2M21 COND liquid | modMS GERM gel |
|---|---|---|---|---|---|---|---|---|---|
| Inorganic salts & vitamins | See Table 2 | See Table 2 | See Table 2 | See Table 2 | See Table 2 | See Table 2 | See Table 2 | See Table 2 | See Table 2 |
| Myo-inositol | 500 | 500 | 500 | 500 | 500 | 100 | 100 | 100 | 100 |
| Casein hydrolysate[a] | 500 | 500 | 500 | 500 | 500 | | | | |
| Sucrose | | 15000 to 30000 | 30000 | 15000 to 30000 | 15000 to 30000 | | | | 3000 |
| Maltose | 30000 | | | | | 2000 | 2000 | 2000 | |
| 2,4-D | 3 | 3 | 3 | 3 | 3 | | | | |
| BAP | 0.5 | 0.5 | 0.5 | 0.5 | 0.5 | | | | |
| ABA | 10 | 10 | 10 | 10 | 10 | 21 | 21 | 21 | |
| Glutamine | | 250 | 250 | 3000 | 3000 | 1450 | 1450 | 1450 | |
| Glycine | | 2 | 2 | 2 | 2 | | | | |
| Phytagel[b] | | | | 3000 | | | | | |
| Gelrite[c] | 1500 | 2000 | | | | 2000 | 2000 | | 2000 |
| Polyethylene glycol (PEG) | | | | | | 70000 to 130000 | | | |
| Activated carbon[d] | | | 500 | 500 | 500 | 1250 | | | 5000 |

[a]Sigma C4523 casein hydrolysate
[b]Phytagel added in gelled Mi3 only.
[c]Gelrite (Gellan Gum, Schweizerhall, no. 89200, Merck, Kelco Div.)
[d]Activated carbon (Nuchar SN, MeadWestvaco)

TABLE 2

Table 2. Medium inorganic salt and vitamin formulation.

| Component | Level (mg/liter) | | | | | |
|---|---|---|---|---|---|---|
| | WV5 INIT | DCR MAINT | Mi3 BULKUP | MSG EPROD | 2M21 COND | modMS GERM |
| $NH_4NO_3$ | 700 | 400 | 200 | | | 800 |
| $KNO_3$ | 259 | 340 | 910 | 100 | 100 | 100 |
| KCL | 1327 | | | 745 | 745 | 745 |
| $CaCl_2 \cdot 2H_2O$ | | 85 | | 440 | 440 | 440 |
| $Ca(NO_3)_2 \cdot 4H_2O$ | 963 | 556 | 236 | | | |
| $MgSO_4 \cdot 7H_2O$ | 1850 | 370 | 247 | 370 | 370 | 370 |
| $Mg(NO_3)_2 \cdot 6H_2O$ | | | 257 | | | |
| $Mg(Cl)_2 \cdot 6H_2O$ | | | 102 | | | |
| $KH_2PO_4$ | 270 | 170 | 136 | 170 | 170 | 170 |
| $MnSO_4 \cdot H_2O$ | 15.16 | 22.3 | 10.5 | 16.9 | 16.9 | 16.9 |
| $ZnSO_4 \cdot 7H_2O$ | 8.6 | 8.6 | 14.7 | 8.6 | 8.6 | 8.6 |
| $CuSO_4 \cdot 5H_2O$ | 0.25 | 0.25 | 0.173 | 0.025 | 0.025 | 0.025 |
| KI | 0.83 | 0.83 | 4.16 | 0.83 | 0.83 | 0.83 |
| $CoCl_2 \cdot 6H_2O$ | 0.025 | 0.025 | 0.125 | 0.025 | 0.025 | 0.025 |
| $H_3BO_3$ | 31 | 6.2 | 15.5 | 6.2 | 6.2 | 6.2 |
| $Na_2MoO_4 \cdot 2H_2O$ | 0.25 | 0.25 | 0.125 | 0.25 | 0.25 | 0.25 |
| $NiCl_2 \cdot 6H_2O$ | | 0.025 | | | | |
| $FeSO_4 \cdot 7H_2O$ | 27.8 | 27.8 | 27.8 | 27.8 | 27.8 | 27.8 |
| $Na_2EDTA \cdot 2H_2O$ | 37.2 | 37.2 | 37.2 | 37.2 | 37.2 | 37.2 |
| Nicotinic acid | 0.5 | 0.5 | 0.5 | 0.5 | 0.5 | 0.5 |
| Pyridoxine HCL | 0.5 | 0.5 | 0.5 | 0.1 | 0.1 | 0.1 |
| Thiamine HCL | 1 | 1 | 1 | 0.1 | 0.1 | 0.1 |

TABLE 3

Embryo Germination data - Comparison of Hand Harvesting vs. Mass Harvesting methods.

| | Number of Germinants per Gram of Embryogenic Tissue | | | |
|---|---|---|---|---|
| Cell line | TRT 1 | TRT 2 | TRT 3 | TRT 4 |
| K12 | 32 | 27 | 328 | 56 |
| K13 | 356 | 80 | 576 | 100 |
| L31 | 368 | 96 | 968 | 304 |
| M34 | 120 | 148 | 640 | 344 |
| K14 | 776 | 340 | 856 | 844 |
| Q38 | 144 | 132 | 800 | 368 |
| K15 | 404 | 396 | 984 | 692 |
| K16 | 640 | 572 | 924 | 764 |
| K17 | 500 | 299 | 584 | 544 |
| K18 | 432 | 340 | 608 | 364 |
| K19 | 432 | 331 | 332 | 120 |
| K20 | 504 | 292 | 572 | 464 |
| N37 | 216 | 68 | 200 | 132 |
| L32 | 352 | 340 | 848 | 344 |
| K21 | 700 | 740 | 1412 | 920 |
| K22 | 636 | 260 | 1068 | 661 |
| K23 | 108 | 144 | 168 | 300 |
| K24 | 404 | 188 | 296 | 260 |
| K25 | 180 | 229 | 16 | 101 |
| K26 | 316 | 256 | 472 | 272 |
| Average | 381 | 264 | 633 | 398 |

Treatment 1 = Control (HH- standard)
Treatment 2 = HH- MFP -standard
Treatment 3 = MH -standard
Treatment 4 = MH - MFP -standard

TABLE 4

Number of germinants for mass harvesting and hand harvesting of somatic embryos from 20 different cell lines of loblolly pine

| | Number of Germinants/ Gram Tissue | |
|---|---|---|
| Cell Line | Hand Harvesting (HH) | Mass Harvesting (MH) |
| K12 | 24 | 284 |
| K13 | 252 | 292 |
| L31 | 368 | 952 |
| M34 | 96 | 508 |
| K14 | 824 | 752 |
| Q38 | 144 | 800 |
| K15 | 400 | 928 |
| K16 | 588 | 984 |
| K17 | 492 | 656 |
| K18 | 404 | 804 |
| K19 | 396 | 264 |
| K20 | 508 | 532 |
| N37 | 172 | 180 |
| L32 | 368 | 768 |
| K21 | 608 | 1772 |
| K22 | 628 | 1008 |
| K23 | 108 | 144 |
| K24 | 380 | 324 |
| K25 | 180 | 0 |
| K26 | 200 | 300 |
| Average | 357 | 613 |

TABLE 5

Number of plantable somatic seedling for mass harvesting and hand harvesting of somatic embryos from 20 different cell lines of loblolly pine.

| | Number of Plantable Somatic Seedlings/ Gram Embryogenic Tissue | |
|---|---|---|
| Cell Line | Hand Harvesting (HH) | Mass Harvesting (MH) |
| K12 | 8 | 168 |
| K13 | 92 | 108 |
| L31 | 212 | 568 |
| M34 | 44 | 328 |
| K14 | 324 | 236 |
| Q38 | 120 | 368 |
| K15 | 288 | 440 |
| K16 | 256 | 296 |
| K17 | 120 | 56 |
| K18 | 88 | 20 |
| K19 | 264 | 188 |
| K20 | 280 | 212 |
| N37 | 104 | 56 |
| L32 | 244 | 516 |
| K21 | 436 | 660 |
| K22 | 452 | 552 |
| K23 | 0 | 64 |
| K24 | 196 | 112 |
| K25 | 56 | 0 |
| K26 | 96 | 8 |
| Average | 184 | 248 |

TABLE 6

Effect of MH on PEG Block Removal of Loblolly Pine Somatic Embryos

| | % Germination | |
|---|---|---|
| Cell line | Hand Harvesting (HH) | Mass Harvesting (MH) |
| R40 | 86 | 85 |
| S45 | 53 | 45 |
| S46 | 71 | 84 |
| S47 | 44 | 51 |
| Average | 63 | 66 |

TABLE 7

Table 7. Effect of MH on PEG removal from mature loblolly pine somatic embryos.

| | % Germination | |
|---|---|---|
| Cell line | Hand Harvesting (HH) → without COLD, with HRH | Mass Harvesting (MH) → without COLD, with HRH |
| U70 | 1.62 | 77.50 |
| U71 | 0.00 | 60.00 |
| U72 | 0.00 | 53.52 |
| U73 | 0.00 | 53.23 |
| Average | 0.63 | 61.06 |

TABLE 8

Table 8. Effect of casein level during initiation (INIT) and maintenance (MAINT) on growth of loblolly pine somatic embryogenic cultures. Average weights within family followed by same letter are not significantly different according to multiple range test. Logit probability is a measure of the likelihood for each family that difference in percentage of lines ≧1 gram compared to the control is due to chance alone.

| Family | INIT casein (g/l) | MAINT casein (g/l) | Avg. weight (grams) | Number lines tested | % lines ≧1 g | Logit prob. |
|---|---|---|---|---|---|---|
| I | 0.5 | 0.5 | 1.81 b | 68 | 65 | control |
| | 0.5 | 1.0 | 1.98 ab | 69 | 65 | 0.95 |
| | 1.0 | 0.5 | 2.36 ab | 72 | 68 | 0.68 |
| | 1.0 | 1.0 | 2.80 a | 72 | 69 | 0.55 |
| | 1.5 | 0.5 | 2.34 ab | 68 | 68 | 0.72 |
| | 1.5 | 1.5 | 2.68 a | 69 | 70 | 0.55 |
| | 2.0 | 0.5 | 2.18 ab | 75 | 65 | 0.94 |
| | 2.0 | 2.0 | 2.54 ab | 75 | 61 | 0.68 |
| | 2.5 | 0.5 | 2.30 ab | 56 | 73 | 0.31 |
| | 2.5 | 2.5 | 2.53 ab | 56 | 66 | 0.87 |
| H | 0.5 | 0.5 | 1.37 c | 48 | 46 | control |
| | 0.5 | 1.0 | 1.65 c | 48 | 48 | 0.84 |
| | 1.0 | 0.5 | 1.48 c | 53 | 51 | 0.61 |
| | 1.0 | 1.0 | 1.99 abc | 53 | 57 | 0.28 |
| | 1.5 | 0.5 | 1.97 abc | 64 | 64 | 0.06 |
| | 1.5 | 1.5 | 2.40 ab | 66 | 67 | 0.03 |
| | 2.0 | 0.5 | 1.89 bc | 69 | 70 | 0.01 |
| | 2.0 | 2.0 | 2.64 a | 69 | 78 | <0.001 |
| | 2.5 | 0.5 | 1.53 c | 55 | 51 | 0.61 |
| | 2.5 | 2.5 | 2.01 abc | 55 | 64 | 0.07 |

TABLE 9

Table 9. Effect of various Pre-Germination Treatments on Germination of Loblolly Pine Somatic Embryos.

| | Number of germinants per gram of embryogenic tissue | | | | |
|---|---|---|---|---|---|
| Cell line | TRT 1 | TRT 2 | TRT 3 | TRT 4 | TRT 5 |
| S48 | 1560 | 1476 | 1256 | 1088 | 1176 |
| M35 | 264 | 252 | 212 | 256 | 108 |
| Q39 | 808 | 548 | 312 | 396 | 256 |
| V74 | 540 | 296 | 168 | 328 | 380 |
| S49 | 496 | 352 | 288 | 280 | 212 |
| V75 | 260 | 240 | 116 | 172 | 96 |
| M36 | 392 | 524 | 412 | 536 | 624 |
| L33 | 389.3 | 248 | 688 | 292 | 300 |
| V76 | 372 | 276 | 384 | 248 | 188 |
| Average | 564.5 | 468 | 426.2 | 399.5 | 371.1 |

TABLE 10

Table 10. Effect of conditioning at room temperature on embryo germination.

| Treatment | % Germination | % Conversion |
|---|---|---|
| Trt 1 (CS → RT) | 72.5 | 37.5 |
| Trt 2 (RT → CS) | 47.5 | 20.0 |

CS - 2 weeks in cold storage
RT - 2 weeks @ room temperature

TABLE 11

Table 11. Effect of alternative pre-germination treatments on the germination of loblolly pine somatic embryos of 6 different cell lines.

| | Number of germinants per gram of tissue | | |
|---|---|---|---|
| Cell line | Trt 1 (MH→ standard method) | Trt 2 (MH→CS→RT) | Trt 3 (MH→CS) |
| S50 | 888 | 652 | 656 |
| S51 | 756 | 532 | 452 |
| S52 | 444 | 608 | 600 |
| S53 | 352 | 380 | 568 |
| S54 | 796 | 848 | 776 |
| S55 | 668 | 848 | 636 |
| Average | 651 | 645 | 615 |

TABLE 12

Table 12. Summary germination and in vitro conversion (Plantables) of loblolly pine somatic embryos from eight cell lines on two cold storage treatments for 4, 6 and 8 weeks cold storage (4° C.).

| Cold storage (CS) time | Cell line | Conditioned on Gelled (2M21) Medium: | | | | Conditioned on Liquid (2M21) Medium: | | | |
|---|---|---|---|---|---|---|---|---|---|
| | | % G | Germinants (G)/gram tissue | % P | Plantables (P)/gram tissue | % G | Germinants (G)/gram tissue | % P | Plantables (P)/gram tissue |
| 4 wks | R41 | 12 | 112 | 0 | 0 | 3 | 32 | 0 | 0 |
| | S56 | 19 | 240 | 43 | 80 | 0 | 0 | 0 | 0 |
| | S57 | 36 | 472 | 66 | 312 | 38 | 512 | 81 | 416 |
| | S58 | 47 | 376 | 68 | 256 | 15 | 112 | 64 | 72 |
| | S59 | 33 | 600 | 61 | 368 | 25 | 360 | 51 | 184 |
| | S60 | 37 | 440 | 27 | 104 | 35 | 312 | 10 | 32 |
| | S61 | 26 | 232 | 21 | 48 | 12 | 128 | 31 | 40 |
| | S62 | 23 | 344 | 28 | 96 | 18 | 160 | 45 | 72 |
| | Avg: | 29 | 352 | 39 | 158 | 18 | 202 | 35 | 102 |
| 6 wks | R41 | 8 | 64 | 0 | 0 | 6 | 40 | 60 | 24 |
| | S56 | 31 | 328 | 20 | 64 | 18 | 248 | 57 | 128 |
| | S57 | 27 | 400 | 66 | 264 | 27 | 320 | 48 | 152 |
| | S58 | 39 | 336 | 52 | 176 | 30 | 296 | 62 | 184 |
| | S59 | 42 | 912 | 40 | 448 | 31 | 632 | 43 | 200 |
| | S60 | 39 | 256 | 14 | 40 | 23 | 176 | 18 | 32 |
| | S61 | 29 | 152 | 5 | 16 | 24 | 216 | 7 | 16 |
| | S62 | 21 | 288 | 3 | 8 | 6 | 96 | 75 | 72 |
| | Avg: | 29 | 342 | 25 | 127 | 21 | 253 | 46 | 101 |
| 8 wks | R41 | 17 | 144 | 28 | 40 | 0 | 0 | 0 | 0 |
| | S56 | 43 | 376 | 47 | 176 | 28 | 392 | 45 | 176 |
| | S57 | 27 | 320 | 37 | 88 | 26 | 472 | 62 | 344 |
| | S58 | 50 | 512 | 50 | 304 | 55 | 536 | 63 | 232 |
| | S59 | 33 | 664 | 37 | 272 | 29 | 488 | 41 | 392 |
| | S60 | 39 | 416 | 17 | 72 | 23 | 264 | 6 | 16 |
| | S61 | 46 | 368 | 35 | 128 | 33 | 280 | 29 | 80 |
| | S62 | 13 | 176 | 24 | 40 | 29 | 488 | 26 | 120 |
| | Avg: | 33 | 372 | 34 | 140 | 28 | 365 | 34 | 170 |

TABLE 13

Table 13. Effect of extended cold storage (16 wk on S2M21 medium) on embryo germination.

| Treatment | Cell Line | Average Embryos | Average Germinants | % Germination | Germinants/ Gram of tissue |
|---|---|---|---|---|---|
| Control (4 wk CS) | S63 | 110 | 51 | 46 | 1224 |
| | S64 | 57 | 12 | 21 | 288 |
| | R42 | 46 | 20 | 42 | 472 |
| | S65 | 67 | 18 | 27 | 440 |
| | S66 | 61 | 8 | 13 | 184 |
| | Average | 68 | 22 | 30 | 522 |
| 16 wk CS | S63 | 103 | 46 | 44 | 1096 |
| | S64 | 48 | 15 | 31 | 352 |
| | R42 | 41 | 18 | 43 | 424 |
| | S65 | 80 | 29 | 36 | 696 |
| | S66 | 67 | 18 | 27 | 432 |
| | Average | 68 | 25 | 36 | 600 |

TABLE 14

Table 14. Effect of extended cold storage (16 wk on L2M21 medium) on embryo germination.

| Treatment | Cell Line | Average Embryos | Average Germinants | % Germination | Germinants/ Gram of tissue |
|---|---|---|---|---|---|
| Control (4 wk CS) | S67 | 132 | 63 | 48 | 1512 |
| | S68 | 118 | 46 | 39 | 1104 |
| | R43 | 38 | 0 | 0 | 0 |
| | R44 | 62 | 25 | 40 | 592 |
| | T69 | 160 | 62 | 39 | 1496 |
| | Average | 102 | 39 | 33 | 941 |

TABLE 14-continued

Table 14. Effect of extended cold storage (16 wk on L2M21 medium) on embryo germination.

| Treatment | Cell Line | Average Embryos | Average Germinants | % Germination | Germinants/ Gram of tissue |
|---|---|---|---|---|---|
| 16 wk CS | S67 | 109 | 60 | 55 | 1448 |
|  | S68 | 124 | 55 | 44 | 1320 |
|  | R43 | 22 | 0 | 0 | 0 |
|  | R44 | 51 | 19 | 37 | 456 |
|  | T69 | 181 | 61 | 34 | 1472 |
|  | Average | 97 | 39 | 34 | 939 |

TABLE 15

Table 15. Description of conditioning treatments tested. Treatment no. 1 is the standard control.

| Trt no. | Cold conditioning substrate[a] | Vol. (ml) liquid medium[b] | Time (wks) in cold (4° C.)[c] | Time (wks) in HRH (23° C.)[d] | Total time (wks)[e] conditioning |
|---|---|---|---|---|---|
| 1 | Gelled 2M21 | — | 4 | 3 | 7 |
| 2 | Gelled 2M21 | — | 8 | 3 | 11 |
| 3 | Gelled 2M21 | — | 12 | 3 | 15 |
| 4 | Gelled 2M21 | — | 16 | 3 | 19 |
| 5 | 2 filter papers + liquid 2M21 | 2 | 8 | — | 8 |
| 6 | 2 filter papers + liquid 2M21 | 2 | 12 | — | 12 |
| 7 | 2 filter papers + liquid 2M21 | 2 | 16 | — | 16 |
| 8 | 2 filter papers + liquid 2M21 | 1 | 8 | — | 8 |
| 9 | 2 filter papers + liquid 2M21 | 1 | 12 | — | 12 |
| 10 | 2 filter papers + liquid 2M21 | 1 | 16 | — | 16 |

[a]Substrate is what rafts with embryos were placed on during cold conditioning. The conditioning plates in treatments 5 to 10 were wrapped with filter tape to allow slow moisture loss from the plate during cold conditioning. Conditioning plates in treatments 1 to 4 were wrapped with Nescofilm ™ during cold conditioning.
[b]Volume of liquid medium applied to filter paper substrate during cold conditioning.
[c]Embryos were cold conditioned first.
[d]HRH conditioning (in pipette boxes) at 23 C. followed the cold conditioning.
[e]Total time, cold + HRH (if applied), in conditioning.

TABLE 16

Table 16. Summary of germination and conversion (plantable) data listed by conditioning treatment. See table 15 for description of each conditioning treatment.

| | Conditioning treatment no. | | | | | | | | | |
|---|---|---|---|---|---|---|---|---|---|---|
| | 1 | 2 | 3 | 4 | 5 | 6 | 7 | 8 | 9 | 10 |
| Average % germination | 38 | 33 | 14 | 18 | 23 | 26 | 35 | 47 | 35 | 35 |
| Std dev % germination | 8 | 3 | 2 | 1 | 17 | 12 | 6 | 3 | 6 | 10 |
| Average % plantable | 34 | 15 | 37 | [a]— | 18 | 26 | 46 | 46 | 45 | 41 |
| Std dev % plantable | 13 | 2 | 12 | — | 8 | 7 | 3 | 8 | 5 | 4 |
| Average % embryos plantable | 12 | 5 | 5 | — | 5 | 7 | 16 | 22 | 16 | 14 |
| Std dev % embryos plantable | 3 | 1 | 2 | — | 5 | 5 | 3 | 6 | 4 | 5 |

[a]Plates and data missing.

TABLE 17

Table 17. Effect of 10 different embryo conditioning treatments on moisture loss from conditioning plates (columns A to D) and moisture content of embryos after conditioning (columns E to H). See Table 15 for description of treatments. The somatic embryos were from 5 pooled cell lines.

| Trt no. | A time (wks) in cold | B liquid (g) added to filter paper | C post cond. (g) water loss | D % water loss (of liquid added to filter) | Plate | E fresh wt. embryos (g) | F water content embryos (g) | G % moist. embryos (fr. wt. basis) | H Avg. ± st. dev. % moist. |
|---|---|---|---|---|---|---|---|---|---|
| 1 | 4 | — | nd | — | 1 | 0.046 | 0.035 | 76 | 77 ± 2 |
| (standard method, control) | | | | | 2 | 0.056 | 0.044 | 79 | |
| | | | | | 3 | 0.057 | 0.044 | 77 | |
| 2 | 8 | — | nd | — | 1 | 0.059 | 0.045 | 76 | 77 ± 1 |
| | | | | | 2 | 0.058 | 0.045 | 78 | |
| | | | | | 3 | 0.055 | 0.043 | 78 | |
| 3 | 12 | — | nd | — | 1 | 0.058 | 0.034 | 58 | 63 ± 5 |
| | | | | | 2 | 0.054 | 0.034 | 63 | |
| | | | | | 3 | 0.051 | 0.034 | 68 | |
| 4 | 16 | — | nd | — | 1 | 0.045 | 0.030 | 67 | 73 ± 8 |
| | | | | | 2 | 0.042 | 0.034 | 83 | |
| | | | | | 3 | 0.049 | 0.035 | 71 | |
| 5 | 8 | 2 | 0.8 | 40 | 1 | 0.039 | 0.032 | 81 | 82 ± 1 |
| | | | | | 2 | 0.044 | 0.036 | 83 | |
| | | | | | 3 | 0.041 | 0.033 | 81 | |
| 6 | 12 | 2 | 1.36 | 68 | 1 | 0.055 | 0.047 | 85 | 85 ± 1 |
| | | | | | 2 | 0.038 | 0.032 | 86 | |
| | | | | | 3 | 0.049 | 0.041 | 84 | |
| 7 | 16 | 2 | 1.62 | 81 | 1 | 0.046 | 0.039 | 85 | 87 ± 3 |
| | | | | | 2 | 0.049 | 0.044 | 90 | |
| | | | | | 3 | 0.047 | 0.039 | 84 | |
| 8 | 8 | 1 | 0.81 | 81 | 1 | 0.037 | 0.030 | 80 | 79 ± 1 |
| | | | | | 2 | 0.030 | 0.024 | 79 | |
| | | | | | 3 | 0.028 | 0.022 | 78 | |
| 9 | 12 | 1 | 1.07 | 107 | 1 | 0.012 | 0.005 | 43 | 44 ± 1 |
| | | | | | 2 | 0.011 | 0.005 | 45 | |
| | | | | | 3 | 0.013 | 0.006 | 44 | |
| 10 | 16 | 1 | 1.17 | 117 | 1 | 0.009 | 0.002 | 18 | 21 ± 5 |
| | | | | | 2 | 0.010 | 0.003 | 27 | |
| | | | | | 3 | 0.011 | 0.002 | 18 | | nd = not determined

TABLE 18

Table 18. Complete data set on in vitro germination and conversion ("plantables") with pine somatic embryos that received different conditioning treatments. See Table 15 for description of each treatment.

| Trt no. | Plate | No. embryos/ plate | total No. germs | % germ | No. plantables | % plantables (of germ) |
|---|---|---|---|---|---|---|
| 1 | 1 | 186 | 55 | 30 | 28 | 51 |
| | 2 | 175 | 60 | 34 | 25 | 42 |
| | 3 | 134 | 63 | 47 | 14 | 22 |
| | 4 | 157 | 58 | 37 | 16 | 28 |
| 2 | 1 | 199 | 64 | 32 | 9 | 14 |
| | 2 | 138 | 40 | 29 | 6 | 15 |
| | 3 | 200 | 72 | 36 | 12 | 17 |
| | 4 | 172 | 47 | 27 | 9 | 19 |
| 3 | 1 | 220 | 22 | 10 | 7 | 32 |
| | 2 | 263 | 38 | 14 | 15 | 39 |
| | 3 | 226 | 29 | 13 | 19 | 66 |
| | 4 | 193 | 16 | 8 | 7 | 44 |
| 4 | 1 | 119 | 17 | 14 | [a]— | — |
| | 2 | 109 | 15 | 14 | — | — |
| | 3 | 98 | 13 | 13 | — | — |
| | 4 | 134 | 15 | 11 | — | — |
| 5 | 1 | 172 | 75 | 44 | 20 | 27 |
| | 2 | 129 | 4 | 3 | 1 | 25 |
| | 3 | 168 | 37 | 22 | 11 | 30 |
| | 4 | 101 | 5 | 5 | 2 | 40 |
| 6 | 1 | 193 | 72 | 37 | 28 | 39 |
| | 2 | 178 | 14 | 8 | 5 | 36 |
| | 3 | 219 | 42 | 19 | 14 | 33 |
| | 4 | 216 | 58 | 27 | 13 | 22 |

TABLE 18-continued

Table 18. Complete data set on in vitro germination and conversion ("plantables") with pine somatic embryos that received different conditioning treatments. See Table 15 for description of each treatment.

| Trt no. | Plate | No. embryos/ plate | total No. germs | % germ | No. plantables | % plantables (of germ) |
|---|---|---|---|---|---|---|
| 7 | 1 | 201 | 75 | 37 | 38 | 51 |
|   | 2 | 235 | 60 | 26 | 31 | 52 |
|   | 3 | 238 | 69 | 29 | 40 | 58 |
|   | 4 | 214 | 82 | 38 | 41 | 50 |
| 8 | 1 | 128 | 54 | 42 | 29 | 54 |
|   | 2 | 207 | 87 | 42 | 37 | 43 |
|   | 3 | 238 | 119 | 50 | 75 | 63 |
|   | 4 | 246 | 107 | 43 | 52 | 49 |
| 9 | 1 | 151 | 31 | 21 | 18 | 58 |
|   | 2 | 211 | 70 | 33 | 39 | 56 |
|   | 3 | 193 | 63 | 33 | 29 | 46 |
|   | 4 | 260 | 97 | 37 | 54 | 56 |
| 10 | 1 | 150 | 53 | 35 | 29 | 55 |
|   | 2 | 157 | 42 | 27 | 21 | 50 |
|   | 3 | 212 | 88 | 42 | 42 | 48 |
|   | 4 | 221 | 37 | 17 | 19 | 51 |

$^a$Plates and data missing.

TABLE 19

Table 19. Comparison of tissue production at different time points in liquid culture. The unit used is production increase in fold in four weeks. If a value in each box is less than 5, it indicates that either the tissue or medium is not suitable for the culture to grow in liquid.

| Cell Line | Treatment | Wk-4 | Wk-8 | Wk-12 | Wk-16 | Wk-20 | Wk-24 | Mean |
|---|---|---|---|---|---|---|---|---|
| J5 | # 1 (DCR 0.5 g/l CH) | 4 | 1 | 1 | 1 | 1 | 1 | 2 |
| J5 | # 2 (DCR 1 g/l CH) | 10 | 2 | 2 | 2 | 2 | 3 | 4 |
| J5 | # 3 (MI3 + 0.5 AC, 1 CH) | 35 | 10 | 38 | 50 | 40 | 25 | 33 |
| J5 | # 4 (MI3 + 0.5AC 2 CH) | 52 | 20 | 78 | 71 | 74 | 63 | 60 |
| J2 | # 1 (DCR 0.5 g/l CH) | 8 | 5 | 44 | 52 | 74 | 46 | 38 |
| J2 | # 2 (DCR 1 g/l CH) | 20 | 11 | 22 | 26 | 44 | 60 | 31 |
| J2 | # 3 (MI3 + 0.5 AC 1 CH) | 66 | 76 | 80 | 75 | 81 | 60 | 73 |
| J2 | # 4 (MI3 + 0.5 AC 2 CH) | 65 | 67 | 61 | 46 | 58 | 39 | 56 |
| J3 | # 1 (DCR 0.5 g/l CH) | 8 | 1 | 1 | 1 | 1 | 1 | 2 |
| J3 | # 2 (DCR 1 g/l CH) | 10 | 3 | 12 | 58 | 67 | 48 | 33 |
| J3 | # 3 (MI3 + 0.5 AC 1 CH) | 27 | 2 | 7 | 40 | 81 | 80 | 40 |
| J3 | # 4 (MI3 + 0.5AC 2 CH) | 54 | 45 | 68 | 63 | 75 | 47 | 59 |
| J6 | # 1 (DCR 0.5 g/l CH) | 10 | 1 | 1 | 7 | 13 | 9 | 7 |
| J6 | # 2 (DCR 1 g/l CH) | 15 | 2 | 18 | 61 | 64 | 57 | 36 |
| J6 | # 3 (MI3 + 0.5 AC 1 CH) | 69 | 46 | 92 | 77 | 55 | 38 | 63 |
| J6 | # 4 (MI3 + 0.5AC 2 CH) | 100 | 82 | 84 | 78 | 91 | 86 | 87 |
| J1 | # 1 (DCR 0.5 g/l CH) | 26 | 5 | 18 | 43 | 37 | 38 | 28 |
| J1 | # 2 (DCR 1 g/l CH) | 41 | 12 | 19 | 28 | 31 | 25 | 26 |
| J1 | # 3 (MI3 + 0.5 AC 1 CH) | 110 | 30 | 20 | 50 | 56 | 80 | 58 |
| J1 | # 4 (MI3 + 0.5AC 2 CH) | 106 | 95 | 89 | 96 | 109 | 94 | 98 |

TABLE 20

Table 20. Comparison of the average number of somatic embryos obtained per embryo development plate from five cell lines that were maintained for 4 to 24 weeks on Mi3 and DCR liquid media containing different levels of casein.

| Cell Line | Treatment | 4 Weeks | 8 Weeks | 12 Weeks | 16 Weeks | 20 Weeks | 24 Weeks | Treatment Mean |
|---|---|---|---|---|---|---|---|---|
| J1 | 1 | 19 AB | 39 AB | 11 AB* | 42 AB** | 128 AB** | 49 AB* | 48 |
| J1 | 2 | 61 AB | 54 AB | 14 AB* | 34 AB | 12 AB | 29 AB | 34 |
| J1 | 3 | 58 AB | 19 AB | 8 AB | 29 AB | 2 AB | 27 AB* | 24 |
| J1 | 4 | 295 AB | 233 AB | 184 AB | 227 AB | 65 AB | 163 AB* | 195 |
| J3 | 1 |  |  |  | 0 AB |  |  | 0 |
| J3 | 2 |  |  | 5 AB | 3 AB | 1 AB | 12 AB* | 5 |
| J3 | 3 | 1 | 9 B | 9 AB* | 3 AB | 1 AB | 1 AB | 4 |
| J3 | 4 | 45 AB | 69 AB | 23 AB | 7 AB | 1 AB | 1 AB | 24 |
| J5 | 1 |  |  |  | 0 AB |  |  | 0 |
| J5 | 2 | 5 B |  | 2 B | 2 AB |  | 14 AB* | 6 |
| J5 | 3 | 10 B | 6 AB | 0 AB | 0 AB | 0 AB | 0 AB | 3 |
| J5 | 4 | 14 AB | 9 AB | 8 AB | 12 AB | 5 AB | 36 AB* | 14 |
| J6 | 1 | 1 AB |  |  | 15 AB | 8 AB* | 3 AB | 7 |
| J6 | 2 | 11 B | 37 B | 3 AB | 2 AB | 0 AB | 0 AB | 9 |
| J6 | 3 | 47 AB | 35 AB | 8 AB | 6 AB* | 1 AB | 5 AB | 17 |
| J6 | 4 | 59 AB | 27 AB | 24 AB | 31 AB | 87 AB | 30 AB | 43 |
| J2 | 1 | 11 AB | 10 AB* | 13 AB | 0 AB | 0 AB | 0 AB | 6 |

TABLE 20-continued

Table 20. Comparison of the average number of somatic embryos obtained per embryo development plate from five cell lines that were maintained for 4 to 24 weeks on Mi3 and DCR liquid media containing different levels of casein.

| Cell Line | Treatment | 4 Weeks | 8 Weeks | 12 Weeks | 16 Weeks | 20 Weeks | 24 Weeks | Treatment Mean |
|---|---|---|---|---|---|---|---|---|
| J2 | 2 | 26 AB | 47 AB | 14 AB | 8 AB* | 2 AB | 1 AB | 16 |
| J2 | 3 | 59 AB | 28 AB | 14 AB | 7 AB* | 4 AB | 10 AB | 20 |
| J2 | 4 | 120 AB | 63 AB* | 19 AB | 10 AB* | 69 AB* | 9 AB | 48 |

A and B are flask designations.
*= significant and
**= highly significant difference.
Empty cells indicate plating was not done due to poor tissue growth. Treatments 1, 2, 3 and 4 as in Table 19.

TABLE 21

Table 21. Effect of tissue bulk up medium treatment on conversion of somatic embryos to plants.

| Cell line | Tissue bulk up medium treatment | Total number germinated embryos | Total number converted embryos | % germinated embryos converted |
|---|---|---|---|---|
| J1 | #1 (Liquid DCR + 0.5 g/l casein) | 60 | 18 | 30 |
| J1 | #2 (Liquid DCR + 1.0 g/l casein) | 60 | 15 | 25 |
| J1 | #3 (Liquid Mi3 + 1.0 g/l casein) | 60 | 14 | 23 |
| J1 | #4 (Liquid Mi3 + 2.0 g/l casein) | 60 | 12 | 20 |
| J2 | #1 (Liquid DCR + 0.5 g/l casein) | 33 | 9 | 27 |
| J2 | #2 (Liquid DCR + 1.0 g/l casein) | 60 | 16 | 27 |
| J2 | #3 (Liquid Mi3 + 1.0 g/l casein) | 60 | 32 | 53 |
| J2 | #4 (Liquid Mi3 + 2.0 g/l casein) | 60 | 29 | 48 |
| Pooled | #1 (Liquid DCR + 0.5 g/l casein) | 93 | 27 | 29 |
| Pooled | #2 (Liquid DCR + 1.0 g/l casein) | 120 | 31 | 26 |
| Pooled | #3 (Liquid Mi3 + 1.0 g/l casein) | 120 | 46 | 38 |
| Pooled | #4 (Liquid Mi3 + 2.0 g/l casein) | 120 | 41 | 34 |

TABLE 22

Table 22. Effect of two maintenance medium on percent success of lines grown to at least 1 gram tissue weight.

| Medium | Number of Initiated Cell Lines | Number of Cell Lines Grown to 1 Gram | Percent Success |
|---|---|---|---|
| DCR | 1325 | 525 | 40% |
| Mi3 with 0.5 g/l casein | 1322 | 673 | 51% |

TABLE 23

Table 23. Comparison of success at growing embryogenic lines from five different families of loblolly pine to at least 3 grams on medium with 0.5 versus 2.0 g/l casein.

| Medium | Family | Number of Initiated Cell Lines | Number of Cell Lines Grown to 3 grams | Percent Success |
|---|---|---|---|---|
| Mi3 with 0.5 g/l casein | 1 | 657 | 297 | 45% |
| Mi3 with 0.5 g/l casein | 2 | 77 | 11 | 14% |
| Mi3 with 0.5 g/l casein | 3 | 58 | 10 | 17% |
| Mi3 with 0.5 g/l casein | 4 | 60 | 25 | 42% |
| Mi3 with 0.5 g/l casein | All | 852 | 343 | 40% |
| Mi3 with 2.0 g/l casein | 1 | 659 | 330 | 50% |
| Mi3 with 2.0 g/l casein | 2 | 59 | 23 | 39% |
| Mi3 with 2.0 g/l casein | 3 | 37 | 10 | 27% |
| Mi3 with 2.0 g/l casein | 4 | 59 | 27 | 46% |
| Mi3 with 2.0 g/l casein | All | 814 | 390 | 48% |

TABLE 24

Table 24. Media effects on embryo production.

| Cell Line | Above Score 13PEG | Above Score 7PEG | Embryos/200 mg 13PEG | Embryos/200 mg 7PEG |
|---|---|---|---|---|
| 1 | Yes | Yes | 5.2 | 7.4 |
| 2 | Yes | No | 13.8 | 0.0 |
| 3 | Yes | Yes | 7.6 | 2.8 |
| 4 | Yes | Yes | 2.0 | 10.4 |
| 5 | No | No | 0.0 | 0.8 |
| 6 | Yes | Yes | 9.4 | 26.8 |
| 7 | Yes | Yes | 7.8 | 18.2 |
| 8 | Yes | Yes | 20.6 | 16.2 |
| 9 | No | Yes | 0.0 | 2.2 |
| 10 | Yes | Yes | 2.6 | 49.4 |
| 11 | Yes | Yes | 9.6 | 3.6 |
| 12 | Yes | Yes | 5.6 | 14.2 |
| 13 | Yes | Yes | 14.4 | 16.6 |
| 14 | No | Yes | 1.6 | 2.0 |
| 15 | Yes | Yes | 16.2 | 15.0 |
| 16 | Yes | No | 4.6 | 0.2 |
| 17 | Yes | Yes | 8.6 | 27.2 |
| 18 | No | No | 0.0 | 1.2 |
| 19 | No | No | 0.2 | 0.0 |
| 20 | No | Yes | 0.2 | 2.7 |
| 21 | Yes | Yes | 5.8 | 8.4 |
| 22 | Yes | Yes | 3.4 | 12.4 |
| 23 | No | Yes | 1.6 | 7.8 |
| 24 | Yes | Yes | 20.4 | 8.2 |
| 25 | Yes | Yes | 20.0 | 13.2 |
| 26 | Yes | No | 5.2 | 1.2 |

Yes = Cell line made at least 10 embryos per gram of tissue
No = Cell line made less than 10 embryos per gram of tissue

TABLE 25

Table 25. Effect of liquid maintenance medium treatments on growth average SCV at four weeks) from five J cell lines (pooled).

| | Mean SCV from five lines | | | |
|---|---|---|---|---|
| Suspension age (month) | #1 Liquid DCR 0.5 g/l Casein | #2 Liquid DCR 1.0 g/l Casein | #3 Liquid Mi3 1.0 g/l Casein | #4 Liquid Mi3 2.0 g/l Casein |
| 1 | 52 | 60 | 83 | 88 |
| 2 | 53 | 63 | 89 | 111 |
| 3 | 65 | 78 | 100 | 118 |
| 4 | 74 | 89 | 112 | 116 |
| 5 | 52 | 92 | 112 | 120 |
| 6 | 54 | 94 | 106 | 113 |
| Average: | 59 | 80 | 100 | 111 |

TABLE 26

Table 26. Effect of four tissue bulk up treatments on tissue production, embryo production and potential embryo production of five cell lines (pooled). Data represents increase in fold compared to the control treatment #1.

| | Fold increase compared to control (Trt #1) | | | |
|---|---|---|---|---|
| Production parameter | #1 Liquid DCR 0.5 g/l Casein | #2 Liquid DCR 1.0 g/l Casein | #3 Liquid Mi3 1.0 g/l Casein | #4 Liquid Mi3 2.0 g/l Casein |
| Tissue | 1 | 1.7 | 3.5 | 4.7 |
| Embryo | 1 | 1.2 | 1.2 | 5.4 |
| Potential Embryo | 1 | 2.0 | 4.0 | 25.0 |

TABLE 27

Table 27: Summary of the effect of casein level on post-cryo recovery growth (fresh weight of tissue in grams) of H and I loblolly pine embryogenic cell lines.

| Family | Treatment Mi3 medium with: | Average 4-week Tissue wt | Average Potential 6-week Tissue wt |
|---|---|---|---|
| H | 0.5 g/l casein | 0.59 | 7.13 |
| | 2.0 g/l casein | 1.34 | 16.65 |
| I | 0.5 g/l casein | 0.37 | 1.13 |
| | 2.0 g/l casein | 0.63 | 4.69 |

TABLE 28

Table 28. Effect of casein level on the frequency of recovery of loblolly pine embryogenic cell lines from cryogenic storage.

| Family | Treatment Mi3 medium with: | No. lines tested | No. lines recovered | % lines recovered |
|---|---|---|---|---|
| H | 0.5 g/l casein | 10 | 6 | 60 |
| | 2.0 g/l casein | 10 | 9 | 90 |
| I | 0.5 g/l casein | 12 | 7 | 58 |
| | 2.0 g/l casein | 12 | 12 | 100 |

TABLE 29

Table 29: Comparison of tissue production, number of somatic embryos per gram of tissue and embryo production potential from five cell lines of family J maintained on post-cryo maintenance with and without brassinolide. The same letter between treatments of each cell line indicates a non-significant difference. Bold numbers indicate best treatment.

| Cell line | Post-Cryo Maintenance Treatment | Average tissue weight (g) at 6 weeks | Number Embryos per g | Embryo production potential |
|---|---|---|---|---|
| J7 | #1 (Mi3) | 6.8 | 330 a | 2244 |
| | #2 (Mi3 + Brassinolide) | 9.8 | 190 a | 1862 |
| J4 | #1 (Mi3) | 0 | NR[x] | NT[y] |
| | #2 (Mi3 + Brassinolide) | 1.0 | 170 | 170 |
| J8 | #1 (Mi3) | 14.1 | 50 b | 705 |
| | #2 (Mi3 + Brassinolide) | 17.2 | 90 b | 1548 |
| J1 | #1 (Mi3) | 9.2 | 960 b | 8832 |
| | #2 (Mi3 + Brassinolide) | 10.8 | 1330 a | 14364 |
| J9 | #1 (Mi3) | 5.4 | 300 a | 1620 |
| | #2 (Mi3 + Brassinolide) | 5.8 | 355 a | 2059 |

[x]NR = No recovery, this genotypes failed to grow on medium without brassinolide.
[y]NT = Not tested due to no tissue recovered.

TABLE 30

Table 30. Comparison of tissue production, number of somatic embryos per gram of tissue and embryo production potential from five cell lines of family K maintained on post-cryo maintenance with and without brassinolide. The same letter between treatments of each cell line indicates a non-significant difference. Bold numbers indicate best treatment.

| Cell line | Post-Cryo Maintenance Treatment | Average tissue weight (g) at 6 weeks | Number Embryos per g | Embryo production potential |
|---|---|---|---|---|
| K11 | #1 (MI3) | 2.2 | 178 a | 381 |
| | #2 (Mi3 + Brassinolide) | 6.9 | 61 b | 420 |
| K27 | #1 (MI3) | 4.1 | 975 a | 3988 |
| | #2 (Mi3 + Brassinolide) | 8.8 | 56 b | 496 |
| K28 | #1 (MI3) | 5.4 | 34 a | 182 |
| | #2 (Mi3 + Brassinolide) | 13.2 | 29 a | 378 |
| K29 | #1 (MI3) | 0.8 | 168 a | 131 |
| | #2 (Mi3 + Brassinolide) | 1.4 | 71 b | 99 |
| K30 | #1 (MI3) | 9.6 | 158 a | 1518 |
| | #2 (Mi3 + Brassinolide) | 11.6 | 610 b | 7064 |

TABLE 31

Table 31. Family by media treatment interaction obtained by a battery screening approach using four different initiation and maintenance media on 7 different genetic families. The percentage of starting seed that established embryogenic cultures is shown for each medium treatment.

| Trt. No. | Initiation (WV5-based medium) | Maintenance (Mi3-based medium)[b] | % Starting seed (family A to G) that established SE cultures | | | | | | |
|---|---|---|---|---|---|---|---|---|---|
| | | | A | B | C | D | E | F | G |
| 1 | Control[a] | Control[b] | 0 | 10 | 1 | 10 | 2 | 14 | 5 |
| 2 | 2.0 Casein | 2.0 Casein | 0 | 8 | 3 | 22* | 7* | 20 | 7 |
| 3 | 15 Maltose | Control | 1 | 10 | 5 | 13 | 4 | 15 | 13* |
| 4 | 2.0 Casein & 15 Maltose | 2.0 Casein | 1 | 10 | 11* | 16 | 6 | 26* | 13* |

[a] Control WV5 initiaiton medium contains 30 g/l maltose and 0.5 g/l casein
[b] Control Mi3 maintenance medium contains 30 g/l sucrose and 0.5 g/l casein
* Statistically different than control (logit probability test).

TABLE 32

Table 32. Effect of polyethylene glycol (PEG) level and type on somatic embryo production, germination and plant establishment among 7 loblolly pine somatic embryogenic cell lines.

| Cell line | Trt no. | PEG level and type in embryo development medium | Avg. number embryos per plate | % embryos germinate | Number plants per plate |
|---|---|---|---|---|---|
| A1 | 1 | 7% Fluka 4000 | 76 | 57 | 22 |
| | 2 | 13% Fluka 4000 | 120 | 20 | 9 |
| | 3 | 7% Acros 8000 | 42 | 46 | 5 |
| | 4 | 13% Acros 8000 | 85 | 39 | 14 |
| B1 | 1 | 7% Fluka 4000 | 34 | 69 | 17 |
| | 2 | 13% Fluka 4000 | 74 | 66 | 23 |
| | 3 | 7% Acros 8000 | 37 | 66 | 7 |
| | 4 | 13% Acros 8000 | 67 | 71 | 8 |
| C1 | 1 | 7% Fluka 4000 | 33 | 41 | 7 |
| | 2 | 13% Fluka 4000 | 67 | 64 | 22 |
| | 3 | 7% Acros 8000 | 20 | 13 | 0 |
| | 4 | 13% Acros 8000 | 68 | 60 | 6 |
| D1 | 1 | 7% Fluka 4000 | 36 | 34 | 5 |
| | 2 | 13% Fluka 4000 | 62 | 23 | 4 |
| | 3 | 7% Acros 8000 | 36 | 31 | 6 |
| | 4 | 13% Acros 8000 | 85 | 61 | 9 |
| E1 | 1 | 7% Fluka 4000 | 67 | 88 | 20 |
| | 2 | 13% Fluka 4000 | 121 | 82 | 25 |
| | 3 | 7% Acros 8000 | 106 | 86 | 31 |
| | 4 | 13% Acros 8000 | 162 | 84 | 14 |
| F1 | 1 | 7% Fluka 4000 | 62 | 86 | 7 |
| | 2 | 13% Fluka 4000 | 13 | 25 | 1 |
| | 3 | 7% Acros 8000 | 43 | 83 | 11 |
| | 4 | 13% Acros 8000 | 40 | 62 | 4 |
| G1 | 1 | 7% Fluka 4000 | 28 | 45 | 5 |
| | 2 | 13% Fluka 4000 | 51 | 68 | 14 |
| | 3 | 7% Acros 8000 | 29 | 59 | 4 |
| | 4 | 13% Acros 8000 | 44 | 48 | 6 |

TABLE 33

Table 33. Germination of loblolly pine somatic embryos of one family J cell line after exposure to two conditioning methods.

| Embryo Conditioning Method[a] | Number embryos tested[b] | % Germination Avg. ± St. Dev.[c] |
|---|---|---|
| 1. Control | 478 | 42 ± 11 |
| 2. New method | 499 | 41 ± 6 |

[a] 1. Control: Substrate is gelled medium, 28 d at 7° C., followed by 21 d in sealed vessel, over water at 24° C. (HRH)
2. New method: Same as Control during 28 d at 7° C., followed by 21 d in sealed vessel over filter paper at 24° C.
[b] 5 replications/method, 60 to 178 embryos/rep
[c] Average ± standard deviation germination percentage among 5 reps/method

TABLE 34

Table 34. Germination of loblolly pine somatic embryos after exposure to two conditioning methods.

| Embryo Conditioning Method[a] | Number embryos tested[b] | % Germination Avg. ± St. Dev.[c] |
|---|---|---|
| 1. Control | 3486 | 66 ± 22 |
| 2. New method | 7542 | 69 ± 22 |

[a] Same methods used as in table 33
[b] Embryos from 68 genotypes tested in method 1, and from 65 different genotypes in method 2
[c] Average ± standard deviation germination percentage among different genotypes within each method

What is claimed is:

1. A medium for growing an embryonic tissue of a coniferous tree, comprising casein hydrolysate in a concentration from 2000 to about 3000 mg/l and activated carbon in an amount from 500 to 5000 mg/liter.

2. The medium of claim 1, wherein the concentration of casein hydrolysate is from 2000 mg/l to 2500 mg/l.

3. The medium of claim 1, further comprising myo-inositol, sucrose, and glutamine.

4. The medium of claim 3, wherein the medium further comprises 2 to 30 g/l maltose, 3 mg/l 2,4-D, 0.5 mg/l BAP, 10 mg/l ABA, and 2 mg/l glycine; and either 3 g/l phytagel or 1.5 to 2 g/l gelrite.

5. The medium of claim 4, further comprising brassinolide in an amount from 0.01 μM to 0.20 μM.

6. The medium of claim 1, wherein the medium is liquid medium or gel medium.

7. A method of producing germination ready somatic embryos, comprising:
(A) culturing proliferative somatic embryo tissue in the medium of claim 1;
(B) transferring the cultured tissue onto polyethylene glycol-containing maturation medium to produce embryos;
(C) harvesting the embryos that are produced from step (B); and
(D) placing the embryos in a high relative humidity environment for a period of time; wherein after the period of time, the embryos are germination ready somatic embryos.

8. The method of claim 7, wherein the medium on which the proliferative somatic embryo tissue is cultured is liquid medium or gel medium.

9. The method of claim 8, wherein the medium on which the proliferative somatic embryo tissue is cultured is liquid medium.

10. The method of claim 7, wherein the step of harvesting the embryos further comprises rinsing the embryos with liquid to remove any polyethylene glycol adhered to the embryo surface.

11. The method of claim 10, wherein the liquid is water.

12. The method of claim 7, wherein the period of time in which the embryos are placed in a high relative humidity environment is for either (a) about 1-5 weeks, or (b) 1-12 weeks at +4°degree. C.

13. The method of claim 7, further comprising the step of placing the harvested embryos on second maturation/conditioning medium for a second period of time prior to placement in the high relative humidity environment.

14. The method of claim 8, wherein the liquid medium further comprises 0.01-1.00 μM of brassinolide.

15. The method of claim 13, wherein the second period of time in which the harvested embryos are placed on the second medium is from 1 day to about 8 weeks.

16. The method of claim 7, wherein the high relative humidity environment is a sealed container.

17. The method of claim 16, wherein the sealed container is a Petri dish.

18. The method of claim 7, wherein the amount of polyethylene glycol in the maturation medium is from about 7% to about 13%.

19. The method of claim 7, wherein the maturation medium comprises abscisic acid, glutamine, and maltose.

20. The method of claim 19, wherein the maturation medium comprises the components listed in Table 1 for 2M21 in the specified amounts (mg/liter).

21. The method of claim 7, wherein the somatic embryo tissue is selected from the group consisting of Loblolly pine somatic embryo tissue, Pitch pine somatic embryo tissue, and Radiata pine somatic embryo tissue.

* * * * *